(12) United States Patent
Block et al.

(10) Patent No.: US 11,802,272 B2
(45) Date of Patent: Oct. 31, 2023

(54) ENRICH AND AMPLIFY HIGHLY POTENT HUMAN MESENCHYMAL STEM CELLS FROM ELDERLY CELL POPULATIONS

(71) Applicant: THE BOARD OF REGENTS OF THE UNIVERSITY OF TEXAS SYSTEM, Austin, TX (US)

(72) Inventors: Travis Block, San Antonio, TX (US); Milos Marinkovic, San Antonio, TX (US); Xiao-dong Chen, San Antonio, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 1165 days.

(21) Appl. No.: 15/773,520

(22) PCT Filed: Nov. 4, 2016

(86) PCT No.: PCT/US2016/060624
§ 371 (c)(1),
(2) Date: May 3, 2018

(87) PCT Pub. No.: WO2017/079621
PCT Pub. Date: May 11, 2017

(65) Prior Publication Data
US 2018/0320140 A1 Nov. 8, 2018

Related U.S. Application Data

(60) Provisional application No. 62/250,664, filed on Nov. 4, 2015.

(51) Int. Cl.
*C12N 5/0775* (2010.01)
*A61K 35/28* (2015.01)

(52) U.S. Cl.
CPC ............ *C12N 5/0663* (2013.01); *A61K 35/28* (2013.01); *C12N 2533/90* (2013.01)

(58) Field of Classification Search
CPC ... C12N 5/0663; C12N 2533/90; A61K 35/28
See application file for complete search history.

(56) References Cited

U.S. PATENT DOCUMENTS

| | | | |
|---|---|---|---|
| 7,807,458 B2 * | 10/2010 | Schiller | G01N 33/5044 435/325 |
| 8,084,023 B2 | 12/2011 | Chen et al. | |
| 8,388,947 B2 | 3/2013 | Chen et al. | |
| 8,961,955 B2 | 2/2015 | Chen et al. | |
| 2014/0154219 A1 | 6/2014 | Ratajczak et al. | |

FOREIGN PATENT DOCUMENTS

| WO | WO 2007/067280 | 6/2007 |
|---|---|---|
| WO | WO 2010/039241 | 4/2010 |
| WO | WO 2010/114572 | 10/2010 |
| WO | WO 2012/033763 | 3/2012 |
| WO | WO 2016/070057 | 5/2016 |

OTHER PUBLICATIONS

Hall et al. (2013. "Identification and Isolation of Small CD44-Negative Mesenchymal Stem/Progenitor Cells from Human Bone Marrow Using Elutriation and Polychromatic Flow Cytometry", Stem Cells Translational Medicine, 2(8):567-578) (Year: 2013).*
Lynch and Pei, Age associated communication between cells and matrix: impact on stem cell-based tissue regeneration strategies Organogenesis, Sep. 2014, 10(3): 289-298 (Year: 2014).*
Griffin et al. Anti-donor immune responses elicited by allogeneic mesenchymal stem cells: what have we learned so far?, Immunology and Cell Biology, 2013, 91: 40-51 (Year: 2013).*
Nejadnik et al. Autologous Bone Marrow-Derived Mesenchymal Stem Cells Versus Autologous Chondrocyte Implantation, American Journal of Sports Medicine, 2010, 38(6): 1110-1116 (Year: 2010).*
Athanasiou et al., "Sterilization, toxicity, biocompatibility and clinical applications of polylactic acid/polyglycolic acid copolymers," *Biomaterials*, 1996; 17(2): 93-102.
Bonab et al., "Aging of Mesenchymal Stem Cell in Vitro," *BMC Cell Biol.* 2006; 7:14, pp. 1-7.
Campisi et al., "Cellular senescence: A link between cancer and age-related degenerative disease?" *Semin Cancer Biol.*, 2011; 21(6): 354-59.
Cancedda et al., "Tissue engineering and cell therapy of cartilage and bone," *Matrix Biol.*, 2003; 22(1): 81-91.
Chan et al., "Formation of post-confluence structure in human parotid gland acinar cells on PLGA through regulation of E-cadherin" *Biomaterials*, 2012; 33(2): 464-72.
Chen et al., "Extracellular Matrix Made by Bone Marrow Cells Facilitates Expansion of Marrow-Derived Mesenchymal Progenitor Cells and Prevents Their Differentiation Into Osteoblasts" *J. Bone Miner. Res.*, 2007; 22:1943-1956.
Chen et al., "Extracellular matrix provides an optimal niche for the maintenance and propagation of mesenchymal stem cells," *Birth Defects Res C Embryo Today*, 2010; 90(1): 45-54.
Chen et al., "Proliferation and Phenotypic Preservation of Rat Parotid Acinar Cells," *Tissue Eng*, 2005; 11(3-4): 526-34.
Cho et al., "A new mechanism for the aging of hematopoietic stem cells: aging changes the clonal composition of the stem cell compartment but not individual stem cells," *Blood*, 2008; 111(12): 5553-61.
Coppe et al., "Senescence-Associate Secretory Phenotypes Reveal Cell-Nonautonomous Functions of Oncogenic RAS and the p53 Tumor Suppressor," *PLoS Biol.*, 2008; 6(12): 2853-68.

(Continued)

*Primary Examiner* — James D Schultz
*Assistant Examiner* — Alexandra F Connors
(74) *Attorney, Agent, or Firm* — Norton Rose Fulbright US LLP

(57) ABSTRACT

Methods of, treatments using, and devices for restoring the regenerative capability for mesenchymal stem cells and isolating and expanding a small subpopulation of less defective mesenchymal stem cells from the bone marrow stromal cells of people with decreased quality and/or quantity of mesenchymal stem cells, such as elderly people.

14 Claims, 32 Drawing Sheets

(56) References Cited

OTHER PUBLICATIONS

Costa et al., "Biophysical signals controlling cell fate decisions: How do stem cells really feel?" *Int. J. Biochem Cell Biol.*, 2012; 44(12): 2233-7.
Freund et al., "Inflammatory networks during cellular senescence: causes and consequences" *Trends Mol Med.*, 2010; 16(5): 238-46.
Gang et al., "SSEA-4 identifies mesenchymal stem cells from bone marrow," *Blood*, 2007; 109(4): 1743-51.
International Preliminary Report on Patentability issued in PCT Application No. PCT/US2016/060624, dated May 8, 2018.
International Search Report and Written Opinion issued in PCT Application No. PCT/US2016/060624, dated Apr. 5, 2017.
Kagami et al., "Restoring the function of salivary glands" *Oral Dis.*, 2008; 14(1): 15-24.
Kawanabe et al., "Isolation and characterization of SSEA-4-positive subpopulation of human deciduous dental pulp cells," *Clin. Oral Investig.* 2015; 19(2): 363-71.
Lai et al., "Reconstitution of Marrow-Derived Extracellular Matrix Ex Vivo: A Robust Culture System for Expanding Large-Scale Highly Functional Human Mesenchymal Stem Cells," *Stem Cells Dev.* 2010; 19(7):1095-1107.
Leal-Egana & Scheibel, "Silk-based materials for biomedical applications," *Biotechnol Appl. Biochem.*, 2010; 55(3): 155-67.
Maria et al., "Matrigel Improves Functional Properties of Primary Human Salivary Gland Cells," *Tissue Eng. Part A.*, 2011; 17(9-10): 1229-38.
Nagaoka et al., "Application of Recombinant Fusion Proteins for Tissue Engineering," *Ann Biomed Eng.*, 2010; 38(3): 683-93.
Pipino et al., "Molecular and Phenotypic Characterization of Human Amniotic Fluid-Derived Cells: A Morphological andProteomic Approach," *Stem Cells Dev.*, 2015; 24(12): 1415-28.
Ratajczak et al., "Very Small Embryonic Like (VSEL) Stem Cells—Characterization, Developmental Origin and Biological Significance," *Exp Hematol.* 2008; 36(6): 742-751.
Ratajczak et al., "Very small embryonic like (VSEL) stem cells in adult organs and their potential role in rejuvenation of tissues and longevity," *Exp Gerontol.*, 2008; 43(11): 1009-1017.
Sun et al., "Rescuing replication and osteogenesis of aged mesenchymal stem cells by exposure to a young extracellular matrix," *FASEB J.*, 2011; 25(5): 1474-85.
Szade et al., "Comment on: The Proper Criteria for Identification and Sorting of Very Small Embryonic-Like Stem Cells, and Some Nomenclature Issues," *Stem Cells And Development*, 2014; 23(7): 714-716.
Wagner et al., "Replicative Senescence of Mesenchymal Stem Cells: A Continuous and Organized Process" *PLoS ONE*, 2008; 3(5): e2213.
Zanetti et al., "Suspension-Expansion of Bone Marrow Results in Small Mesenchymal Stem Cells Exhibiting Increased Transpulmonary Passage Following Intravenous Administration," *Tissue Engineering Part C, Methods*, 2015; 21(7): 683-692.
Zhou et al., "Age-related intrinsic changes in human bone-marrow-derived mesenchymal stem cells and their differentiation to osteoblasts," *Aging Cell*, 2008; 7(3): 335-343.
Baker et al. "Characterization of bone marrow-derived mesenchymal stem cells in aging," *Bone*, 2015; 70: 37-47.
Block et al. "Restoring the quantity and quality of elderly human mesenchymal stem cells for autologous cell-based therapies," *Stem Cell Research & Therapy*, 2017; 8(1): 13 pages.
Ge et al. "The size of mesenchymal stem cells is a significant cause of vascular obstructions and stroke," *Stem Cell Rev. and Rep*, 2014; 10(1): 295-303.
Igura et al. "Identification of small juvenile stem cells in aged bone marrow and their therapeutic potential for repair of the ischemic heart," *American Journal of Physiology—Heart and Circulatory Physiology*, 2013; 305(9): H1354-H1362.
Supplementary European Search Report issued in Application No. 16863074.7, dated May 10, 2019.
D'Ippolito et al., "Marrow-isolated adult multilineage inducible (MIAMI) cells, a unique population of postnatal young and old human cells with extensive expansion and differentiation potential", *J Cell Sci.*, 117(Pt 14):2971-2981, 2004.
Ratajczak et al., "Very Small Embryonic-Like Stem Cells (VSELs)", *Circ Res.*, 124(2):208-210, 2019.

\* cited by examiner

ENRICH AND AMPLIFY HIGHLY POTENT HUMAN MESENCHYMAL STEM CELLS FROM ELDERLY CELL POPULATIONS

CROSS-REFERENCE TO RELATED APPLICATIONS

This application is a national phase application under 35 U.S.C. § 371 of International Application No. PCT/US2016/060624, filed Nov. 4, 2016 which claims the benefit of priority to U.S. Provisional Application No. 62/250,664 filed Nov. 4, 2015, the contents of each are incorporated into the present application by reference.

STATEMENT REGARDING FEDERALLY SPONSORED RESEARCH OR DEVELOPMENT

This invention was made with United States government support under the Merit Review Award Program, Grant No. 1-01 BX002145-01, awarded by the U.S. Department of Veterans Affairs. The government has certain rights in the invention.

BACKGROUND OF THE INVENTION

1. Field of the Invention

The present invention relates generally to the fields of cell biology and medicine. More particularly, it concerns methods of, treatments using, and devices for restoring the regenerative capability for mesenchymal stem cells and isolating and expanding a subpopulation of less defective mesenchymal stem cells from the bone marrow stromal cells of people with decreased quantity and/or quality of bone marrow-derived mesenchymal stem, such as elderly people.

2. Description of Related Art

As modern medicine has eliminated many causes of early life mortality, human life expectancy has increased rapidly. Because of this, most people now live long enough to experience disability resulting from age-related degenerative disease at a much higher rate than ever before. This represents a major global health concern as the world's population continues to grow older. Mesenchymal stem cell (MSC) based therapies have great potential for treating these diseases. However, the quantity and quality of mesenchymal stem cells declines with age and limits the effectiveness and potential of stem cell therapies for this aging population.

Bone marrow-derived mesenchymal stem cells (BM-MSCs) are capable of self-renewal and differentiation into multiple cell lineages. Because of these capabilities, BM-MSCs play an important role in continuous maintenance and repair of most tissue types. In general, the quantity and quality of MSCs decrease with aging, which, in turn, is associated with the progressive failure of function of tissues and organs. BM-MSC based therapies have been shown great potential for treatment of many age-related degenerative diseases. Due to biosafety concerns and FDA regulations, a patient's own (autologous) stem cells are considered preferable for cell-based therapies. Also, differences in age and disease severity of the patients, age and health of the donor providing the BM-MSCs, and methods used to isolate and expand the BM-MSCs would likely affect treatment outcomes. However, the quantity and quality of BM-MSCs decrease with aging, limiting the therapeutic potential of a patient's own stem cells. Currently, many stem cell banking companies request that clients donate early, because elderly stem cells lose their potency. Thus, in order for these therapies to be successful for many patients, a strategy must be developed for rescuing the regenerative capacity of aging stem cell populations.

It has been suggested as possible to isolate some hematopoietic stem cells from aging individuals that are identical to young cells, even though the potency is severely diminished at the population level. (Cho, et al., 2008). The inventors have previously demonstrated the ability to rescue the regenerative potential of aged murine stem cells by exposing them to a tissue-specific matrix. (Chen, 2010). However, the same has not been demonstrated in human MSCs.

Extracellular matrix (ECM) is an important component of the cellular niche in tissues, supplying critical biochemical and physical signals to initiate or sustain cellular functions (Chen, et al., 2007; Lai, et al., 2010). A tissue-specific ECM microenvironment may be essential in vivo and in vitro to provide chemical and physical cues to direct/govern multipotent stem cells for tissue regeneration and repair (Chen, 2010; Costa, et al., 2012). With advances in tissue engineering, the various scaffold biomaterials have been developed to mimic ECMs for tissue regeneration or repair (Nagaoka, et al., 2010). Among them, the materials that have been used to support the proliferation and differentiation of progenitor cells include chitosan, polyglycolic acid (PGA), poly-(1)-lactic acid (PLLA), poly (lactic-co-glycolic acid) (PLAG), and poly(ethylene glycol)-terephthalate (PEFT/poly (butylene terephthalate (PBT) (Kagami, et al., 2008; Chan, et al., 2012; Chen, et al., 2005). However, these polymeric scaffolds can induce inflammation resulting from the acidity of their degradation products (Athanasiou, et al., 1996; Cancedda, et al., 2003).

Another potential scaffold material, Matrigel, contains basement membrane proteins secreted by EHS mouse sarcoma cells and has been used to grow primary epithelial cells in culture (Maria, et al., 2011). Although varying levels of success have been achieved with this product, it is not consistent with the long term goal to revitalize bone marrow stromal cells.

Natural scaffold materials, especially silk, are desirable due to their wide ranges of elasticity (allowing tissue-specific scaffold formation), pore sizes (allowing tissue specific nutrition and oxygen access), low bacterial adherence, biodegradability, and low toxicity and immunogenicity (Leal-Egana & Scheibel, 2010). Recently, it has been reported that native extracellular matrix (ECM), generated by bone marrow (BM) cells, enhanced the attachment and proliferation of human and mouse bone marrow-derived mesenchymal stem cells (BM-MSCs) (Chen, et al., 2007; Lai, et al., 2010).

However, there remains a need for methods, compositions, and devices useful for isolating and/or creating MSCs capable of cellular regeneration from a subject with decreased quantity and quality of MSCs, such as elderly subjects. Additionally, there remains a need for methods for obtaining these MSCs and administering them to subjects in need of stem cell therapies who may have age-related degenerative diseases

SUMMARY OF THE INVENTION

Advantageously, the inventors have developed a novel approach that allows the isolation and expansion of a clinically valuable subpopulation of mesenchymal stem cells (MSCs) from the bone marrow stromal cells of people with decreased quantity and/or quality of bone marrow-derived mesenchymal stem cells, such as elderly people. Further, the inventors have disclosed cell culture systems and compositions comprising the aforementioned MSCs. In addition, the inventors have developed methods of obtaining these MSCs and methods of administering them to subjects in need of stem cell therapies who may have age-related degenerative diseases and conditions. Still further, the inventors have developed a novel approach to restore the regenerative capability of bone marrow stromal cells. The methods, compositions, and techniques described herein can also apply to MSCs derived from sources other than bone marrow, e.g. adipose tissue, umbilical cord blood, etc.

The phenotype of MSC cells from elderly and young donors are different, but there is overlap. The inventors disclose herein that small size bone marrow derived mesenchymal stem cells (BM-MSCs) are more likely to express markers of early stage stem cells, and large cells are more likely than small cells to express aging markers such as the levels of reactive oxygen species (ROS). Herein the inventors describe a small population of cells found in BM-MSCs isolated from older donors that are similar in size to the size of the BM-MSCs from young donors. The inventors disclose that the cells of small size from older donors may be more similar to young cells in several respects, including proliferation, differentiation, protein expression, and ROS profile. The inventors also disclose that the environmental conditions of the cells in older subjects may suppress proliferation capacities of the cells in older subjects.

The inventors here disclose that to improve the performance of BM-MSCs isolated from an older donor, it is desirable to isolate cells that are small in size and also express SSEA-4 (SSEA+). This population more closely resembles cells from young donors in several properties that include an increased rate of proliferation, increased adenosine triphosphate (ATP) content per cell, higher telomerase levels, and a greater concentration of stem cells.

The inventors further disclose that culturing the cells on ECM, especially ECM derived from BM-MSCs, exaggerate the differences between the small cells that are SSEA-4 positive. The inventors also disclose that small cells that are SSEA-4 negative also appear to recover significantly when cultured on ECM, especially ECM derived from BM-MSCs. Thus, both SSEA-4 positive and SSEA-4 negative populations are potentially valuable for clinical applications.

In one aspect of the invention, disclosed herein is a method of administering small size bone marrow-derived mesenchymal stem cells (BM-MSCs) to a subject, the method comprising:
(a) harvesting a first set of BM-MSCs from a first donor,
(b) sorting the BM-MSCs from step (a) by size and optionally SSEA-4 expression,
(c) isolating the small size BM-MSCs,
(d) plating the small size BM-MSCs for culturing,
(e) expanding the small size BM-MSCs in culture,
(f) optionally storing the small size BM-MSCs from step (e), and
(g) administering the small size BM-MSCs from step (e) and/or (f) to the subject.

In some embodiments, the subject is the same as the first donor whereby the small size BM-MSCs are autologous. In other embodiments, the small size BM-MSCs have a median diameter of less than 30 microns when measured in suspension. In some embodiments, the small size BM-MSCs expressed SSEA-4 (SSEA-4+) at the time of isolation. In various embodiments, the subject is 50 years of age or older, 65 years of age or older, or 70 years of age or older. In some embodiments, the small BM-MSCs are cultured on TCP or on extracellular matrix (ECM) derived from a second set of BM-MSCs obtained from a second donor. In some embodiments, the second donor is 25 years of age or younger. In other embodiments, the subject has decreased quantity and/or quality of BM-MSCs, and/or is in need of stem cell therapy. In still other embodiments, the subject has an age-related degenerative disease, and/or has a disease or condition that compromises the quantity or quality of BM-MSCs, and/or has or will receive treatments that compromise the quantity or quality of BM-MSCs.

In another aspect of the invention, disclosed herein is a cell culture system comprising culture media and isolated small size BM-MSCs isolated from a first set of BM-MSCs obtained from a first donor, wherein the isolated small size BM-MSCs expressed SSEA-4 (SSEA-4+) at the time of isolation, and wherein the first donor was 65 years of age or older at the time the first set of BM-MSCs were donated. In some embodiments, the cell culture system does not comprise BM-MSCs that were not small in size at the time of isolation. In some embodiments, the cell culture system does not comprise BM-MSCs that did not express SSEA-4 at the time of isolation. In some embodiments, the isolated small size BM-MSCs have a median diameter of less than 30 microns when measured in suspension. In other embodiments, the cell culture system further comprises an extracellular matrix (ECM) derived from a second set of BM-MSCs. In still other embodiments, the second set of BM-MSCs were obtained from a second donor 25 years of age or younger. In various embodiments, the first donor had decreased quantity and/or quality of BM-MSCs, and/or had an age-related degenerative disease, and/or had a disease or condition that compromises the quantity or quality of BM-MSCs at the time the first set of BM-MSCs were donated.

In another aspect of the invention, disclosed herein is a composition comprising isolated small size BM-MSCs isolated from a first set of BM-MSCs obtained from a first donor, wherein the isolated small size BM-MSCs expressed SSEA-4 (SSEA-4+) at the time of isolation, and wherein the first donor was 65 years of age or older at the time the first set of BM-MSCs were donated. In some embodiments, the composition does not comprise BM-MSCs that were not small in size at the time of isolation. In some embodiments, the composition does not comprise BM-MSCs that did not express SSEA-4 at the time of isolation. In some embodiments, the isolated small size BM-MSCs have a median diameter of less than 30 microns when measured in suspension. In other embodiments, the composition further comprises a carrier. In other embodiments, the isolated small size BM-MSCs were cultured on an ECM derived from a second set of BM-MSCs. In still other embodiments, the second set of BM-MSCs were obtained from a second donor 25 years of age or younger. In various embodiments, the first donor had decreased quantity and/or quality of BM-MSCs, and/or had an age-related degenerative disease, and/or had a disease or condition that compromises the quantity or quality of BM-MSCs at the time the first set of BM-MSCs were donated.

In another aspect of the inventions, disclosed herein is a method of obtaining small size BM-MSCs suitable for administration to a subject, the method comprising:
(a) harvesting a first set of BM-MSCs from a first donor,
(b) sorting the BM-MSCs from step (a) by size and optionally SSEA-4 expression,
(c) isolating the small size BM-MSCs,
(d) plating the small size BM-MSCs for culturing,
(e) expanding the small size BM-MSCs in culture, and (f) optionally storing the small size BM-MSCs from step (e).

In some embodiments, the small size BM-MSCs have a median diameter of less than 30 microns when measured in suspension. In some embodiments, steps (b) and (c) are conducted using a flow cytometer. In other embodiments, the small size BM-MSCs expressed SSEA-4 (SSEA-4 +) at the time of isolation. In various embodiments, the first donor is 50 years of age or older, or the first donor is 65 years of age or older, or the first donor is 70 years of age or older. In some embodiments, the small BM-MSCs are cultured on TCP or on extracellular matrix (ECM) derived from a second set of BM-MSCs obtained from a second donor. In some embodiments, the second donor is 25 years of age or younger. In still other embodiments, the first donor has decreased quantity and/or quality of BM-MSCs, and/or is in need of stem cell therapy. In various embodiments, the first donor has an age-related degenerative disease, and/or has a disease or condition that compromises the quantity or quality of BM-MSCs, and/or has or will receive treatments that compromise the quantity or quality of BM-MSCs.

Tissues produced in vitro yet retaining physiological features of in vivo tissues provide a particularly useful tool for monitoring the effects of proposed therapies or molecules on the physiological functions of the tissues. Accordingly, there is disclosed a method of testing the biological activity of a substance, the method comprising:

(a) obtaining any of the cell culture systems as described herein,
(b) adding the substance to the cell culture system; and
(c) measuring a parameter of the cell culture system and/or the cell to determine the effect of adding the substance to the cell culture system.

In some embodiments, the substance is a candidate therapeutic to treat a disease and/or condition. In some instances, the disease and/or condition is caused by or compromises the quantity or quality of BM-MSCs. In some instances, the disease and/or condition is an age related disease or the aging process itself. In some instances, the condition is reduced regenerative capacity of aging stem cell populations, or a side effect of a medication or radiotherapy. In still other embodiments, the substance is a cellular growth factor or cellular differentiation factor. Adding the substance to the cell culture system can comprise adding the substance to the culture medium. The culture medium can be exchanged for a culture medium comprising a particular substance or combination of substances to monitor the effects of the culture medium change on the physiological functions of the cells. Measuring a parameter of the cell culture system can include, for example, observing growth rates or morphological features of cells. Any biologically relevant parameter can be measured and monitored to determine the biological effect of exposing the cells to a substance or of changing any conditions of growth. Changes in the parameter being measured or monitored can be attributed to the presence of the substance or the change in growth conditions if a corresponding control does not show the same change.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

For this application, a number value with one or more decimal places can be rounded to the nearest whole number using standard rounding guidelines, i.e. round up if the number being rounded is 5, 6, 7, 8, or 9; and round down if the number being rounded is 0, 1, 2, 3, or 4. For example, 3.7 can be rounded to 4.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the terms "comprising," "having," "including," or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification.

Throughout this application, the MSCs and BM-MSCs include any progeny cells produced thereof. The term "progeny cell" is used to indicate a cell that is derived from another cell, such as a parent cell. The progeny cell may retain the same characteristics as the parent cell or may have different characteristics, such as a progeny cell that has differentiated.

Throughout this application, "decreased quantity and/or quality" of bone marrow-derived mesenchymal stem cells is used to indicate that the number of stem cells is decreased and/or stem cell function is diminished along one or more dimensions relative to those of a young, healthy subject population's. Non-limiting examples are shown herein of properties of stemness (i.e. SSEA-4, self-renewal, differentiation capacity) and properties of aging (senescence, reactive oxygen species, annexin-5). In a non-limiting example, aging can cause a decreased quantity and/or quality of bone marrow-derived mesenchymal stem cells.

Throughout this application, the term "aging" is used to indicated the sum of processes, by which stem cell populations decrease in quantity and/or quality.

Throughout this application, the term "young" refers to humans (male or female) age 25 years and under, and also refers to the cells obtained from them.

Throughout this application, the term "elderly", "old", or "older" refers to humans (male or female) age 65 years and older, and also refers to the cells obtained from them. However, there are examples in the literature that demonstrate a decline in MSC functions happening as early as 50 years of age (Zhou et al., 2008).

Throughout this application, the term "subject", "patient", or "donor" refers to a male or female human.

Throughout this application, "isolation" of and "isolated" bone marrow-derived mesenchymal stem cells indicates that the cells have been removed from an organism and/or other bone marrow-derived mesenchymal stem cells with different characteristics. In a non-limiting example, bone marrow-derived mesenchymal stem cells may be isolated from a human. In another non-limiting example, bone marrow-derived mesenchymal stem cells that are small in size and/or express SSEA-4 may be isolated from bone marrow-derived mesenchymal stem cells that are not small in size and/or do not express SSEA-4 or express SSEA-4 to a lesser extent than the separated cells.

Throughout this application, the terms "small" and "small size" when used in reference to BM-MSCs cell size means that the "small size" BM-MSCs have a smaller diameter when suspended in solution ("suspended diameter") than the average suspended diameter of the set of BM-MSCs obtained from a donor at a given time. In various embodiments, the small size BM-MSCs are isolated from the set of BM-MSCs obtained from a donor. In various embodiments, the terms "small" and "small size" when used in reference to BM-MSCs cell size means BM-MSCs having a median cell diameter of less than 33 microns, or less than 30 microns, or less than 25 microns, or less than 20 microns, or less than 19 microns when measured in suspension.

Throughout this application, the terms "large" or "large size" when used in reference to BM-MSCs cell size means "large size" BM-MSCs have a larger diameter when suspended in solution ("suspended diameter") than the average suspended diameter of the set of BM-MSCs obtained from a donor at a given time. In various embodiments, the terms "large" and "large size" when used in reference to BM-MSCs cell size means BM-MSCs having a median diameter of greater than 35 microns, or 33 microns and greater when measured in suspension.

Throughout this application, cells that express SSEA-4, that are "SSEA-4 positive," SSEA-4+, or are "positive for SSEA-4 expression", or any variation of these terms, indicates that the cells express SSEA-4 or express SSEA-4 to an extent that is measurable in cells when compared to a negative control. In various embodiments, the SSEA-4 expressing BM-MSCs are isolated from the set of BM-MSCs obtained from a donor.

Throughout this application, cells that do not express SSEA-4, that are "SSEA-4 negative," SSEA-4–, or are negative for SSEA-4 expression, or any variation of these terms, indicates that the cells do not express SSEA-4 or express SSEA-4 to an extent that is not measurable in cells when compared to a negative control. In various embodiments, the SSEA-4 non-expressing BM-MSCs are isolated from the set of BM-MSCs obtained from a donor.

Also, disclosed in the context of the present invention are the following embodiments 1 to 37:

Embodiment 1 is a method of administering small size bone marrow-derived mesenchymal stem cells (BM-MSCs) to a subject, the method comprising:
(a) harvesting a first set of BM-MSCs from a first donor,
(b) sorting the BM-MSCs from step (a) by size and optionally SSEA-4 expression,
(c) isolating the small size BM-MSCs,
(d) plating the small size BM-MSCs for culturing,
(e) expanding the small size BM-MSCs in culture,
(f) optionally storing the small size BM-MSCs from step (e), and
(g) administering the small size BM-MSCs from step (e) and/or (f) to the subject.

Embodiment 2 is the method of embodiment 1, wherein the subject is the same as the first donor.

Embodiment 3 is the method of embodiments 1 or 2, wherein the small size BM-MSCs have a median diameter of less than 30 microns when measured in suspension.

Embodiment 4 is the method of any one of embodiments 1 to 3, wherein the small size BM-MSCs expressed SSEA-4 (SSEA-4 +) at the time of isolation.

Embodiment 5 is the method of any one of embodiments 1 to 4, wherein the subject is 50 years of age or older.

Embodiment 6 is the method of any one of embodiments 1 to 4, wherein the subject is 65 years of age or older.

Embodiment 7 is the method of any one of embodiments 1 to 4, wherein the subject is 70 years of age or older.

Embodiment 8 is the method of any one of embodiments 1 to 7, wherein the small BM-MSCs are cultured on TCP or on extracellular matrix (ECM) derived from a second set of BM-MSCs obtained from a second donor.

Embodiment 9 is the method of embodiment 8, wherein the second donor is 25 years of age or younger.

Embodiment 10 is the method of any one of embodiments 1 to 8, wherein the subject has decreased quantity and/or quality of BM-MSCs, and/or is in need of stem cell therapy.

Embodiment 11 is the method of any of embodiments 1 to 10, wherein the subject has an age-related degenerative disease, and/or has a disease or condition that compromises the quantity or quality of BM-MSCs, and/or has or will receive treatments that compromise the quantity or quality of BM-MSCs.

Embodiment 12 is a cell culture system comprising culture media and isolated small size BM-MSCs isolated from a first set of BM-MSCs obtained from a first donor, wherein the isolated small size BM-MSCs expressed SSEA-4 (SSEA-4+) at the time of isolation, wherein the cell culture system does not comprise BM-MSCs that were not small in size at the time of isolation or BM-MSCs that did not express SSEA-4 at the time of isolation, and wherein the first donor was 65 years of age or older at the time the first set of BM-MSCs were donated.

Embodiment 13 is the cell culture system of embodiment 12, wherein the isolated small size BM-MSCs have a median diameter of less than 30 microns when measured in suspension.

Embodiment 14 is the cell culture system of embodiment 12 or 13, wherein the cell culture system further comprises an extracellular matrix (ECM) derived from a second set of BM-MSCs.

Embodiment 15 is the cell culture system of embodiment 14, wherein the second set of BM-MSCs were obtained from a second donor 25 years of age or younger.

Embodiment 16 is the cell culture system of any one of embodiments 12 to 15, wherein the first donor had decreased quantity and/or quality of BM-MSCs, and/or had an age-related degenerative disease, and/or had a disease or condition that compromises the quantity or quality of BM-MSCs at the time the first set of BM-MSCs were donated.

Embodiment 17 is a composition comprising isolated small size BM-MSCs isolated from a first set of BM-MSCs obtained from a first donor, wherein the isolated small size BM-MSCs expressed SSEA-4 (SSEA-4+) at the time of isolation, wherein the composition does not comprise BM-MSCs that were not small in size at the time of isolation or BM-MSCs that did not express SSEA-4 at the time of isolation, and wherein the first donor was 65 years of age or older at the time the first set of BM-MSCs were donated.

Embodiment 18 is the composition of embodiment 17, wherein the isolated small size BM-MSCs have a median diameter of less than 30 microns when measured in suspension.

Embodiment 19 is the composition of embodiment 17 or 18, wherein the composition further comprises a carrier.

Embodiment 20 is the composition of any of embodiments 17 to 19, wherein the isolated small size BM-MSCs were cultured on a ECM derived from a second set of BM-MSCs.

Embodiment 21 is the composition of embodiment 20, wherein the second set of BM-MSCs were obtained from a second donor 25 years of age or younger.

Embodiment 22 is the composition of any one of embodiments 17 to 21, wherein the first donor had decreased quantity and/or quality of BM-MSCs, and/or had an age-related degenerative disease, and/or had a disease or condition that compromises the quantity or quality of BM-MSCs at the time the first set of BM-MSCs were donated.

Embodiment 23 is a method of obtaining small size BM-MSCs suitable for administration to a subject, the method comprising:
  (a) harvesting a first set of BM-MSCs from a first donor,
  (b) sorting the BM-MSCs from step (a) by size and optionally SSEA-4 expression,
  (c) isolating the small size BM-MSCs,
  (d) plating the small size BM-MSCs for culturing,
  (e) expanding the small size BM-MSCs in culture, and
  (f) optionally storing the small size BM-MSCs from step (e).

Embodiment 24 is the method of embodiment 23, wherein the small size BM-MSCs have a median diameter of less than 30 microns when measured in suspension.

Embodiment 25 is the method of embodiment 23 or 24, wherein steps (b) and (c) are conducted using a flow cytometer.

Embodiment 26 is the method of any one of embodiments 23 to 25, wherein the small size BM-MSCs expressed SSEA-4 (SSEA-4 +) at the time of isolation.

Embodiment 27 is the method of any one of embodiments 23 to 26, wherein the first donor is 50 years of age or older.

Embodiment 28 is the method of any one of embodiments 23 to 26, wherein the first donor is 65 years of age or older.

Embodiment 29 is the method of any one of embodiments 23 to 26, wherein the first donor is 70 years of age or older.

Embodiment 30 is the method of any one of embodiments 23 to 29, wherein the small BM-MSCs are cultured on TCP or on extracellular matrix (ECM) derived from a second set of BM-MSCs obtained from a second donor.

Embodiment 31 is the method of embodiment 30, wherein the second donor is 25 years of age or younger.

Embodiment 32 is the method of any one of embodiments 23 to 30, wherein the first donor has decreased quantity and/or quality of BM-MSCs, and/or is in need of stem cell therapy.

Embodiment 33 is the method of any one of embodiments 23 to 32, wherein the first donor has an age-related degenerative disease, and/or has a disease or condition that compromises the quantity or quality of BM-MSCs, and/or has or will receive treatments that compromise the quantity or quality of BM-MSCs.

Embodiment 34 is a method of testing the biological activity of a substance, the method comprising:
  (a) obtaining the cell culture system of any one of embodiments 12 to 16,
  (b) adding the substance to the cell culture system; and
  (c) measuring a parameter of the cell culture system and/or the cell to determine the effect of adding the substance to the cell culture system.

Embodiment 35 is the method of embodiment 34, wherein the substance is a candidate therapeutic to treat a disease and/or condition.

Embodiment 36 is the method of embodiment 35, wherein the disease and/or condition is caused by or compromises the quantity or quality of BM-MSCs.

Embodiment 37 is the method of any of embodiments 34 to 36, wherein the substance is a cellular growth factor or cellular differentiation factor.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The inventors of the present application have developed novel approaches that allow the isolation and expansion of a subpopulation of less defective mesenchymal stem cells (MSCs) from the bone marrow stromal cells of people with decreased quantity and/or quality of bone marrow-derived mesenchymal stem cells (BM-MSCs), such as elderly people, and thus have discovered a strategy for rescuing the regenerative capacity of aging stem cell populations. Further, the inventors have disclosed cell culture systems, techniques and compositions of the aforementioned MSCs, which can be very effective to rescue human stem cells from a donor with decrease quantity and/or quality of human stem cells. In addition, the inventors have developed methods of obtaining these MSCs and methods of administering them to subjects in need of stem cell therapies who may have age-related degenerative diseases and conditions. Still further, the inventors have developed a novel approach to restore the regenerative capability of bone marrow stromal cells.

Figure 1:
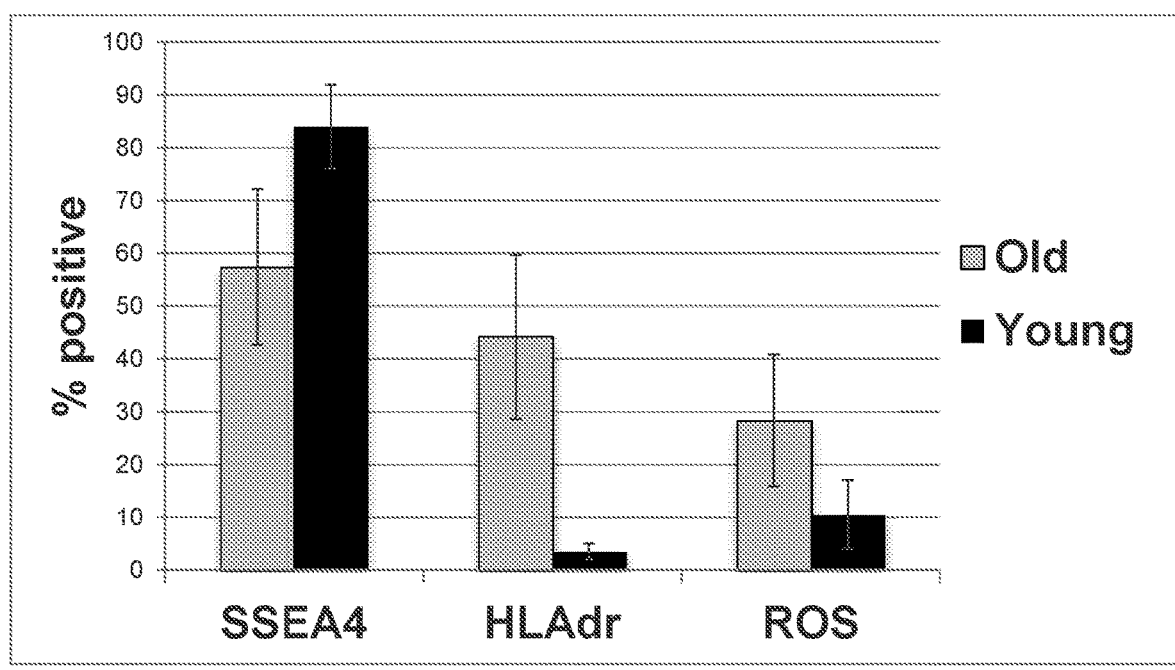
FIG. 1—MSCs from old and young donors express unique phenotypes. Differences in the percentage of cells positive for stage-specific embryonic antigen 4 (SSEA-4), human major histocompatibility complex (MEW) class II HLAdr, and reactive oxygen species (ROS) is shown between BM-MSCs from old donors (left columns) and young donors (right columns).
Figure 2:
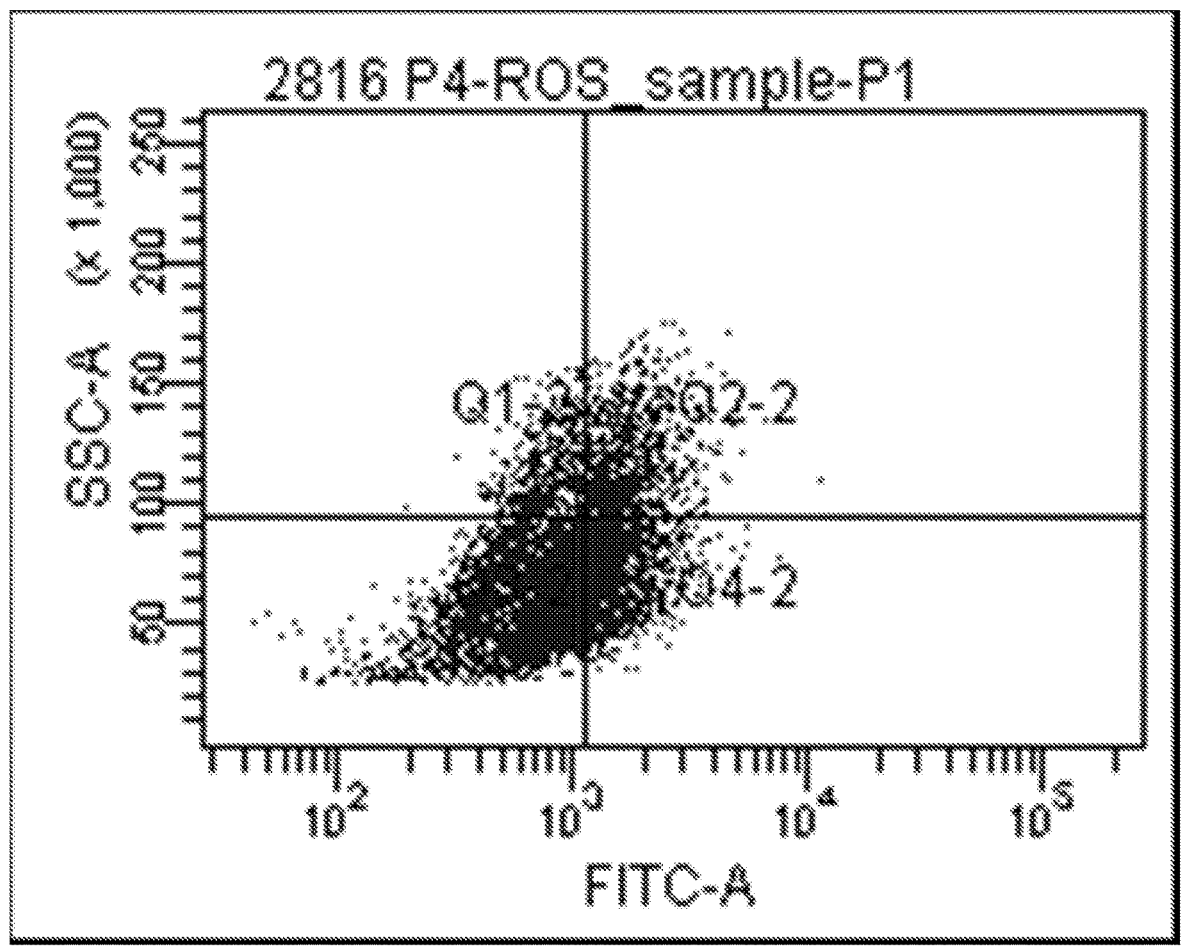
FIG. 2—Large MSCs are more likely to express aging markers. Scatter plot of BM-MSC cells sorted by size (Large and Small) and presence of ROS (Positive) or absence of ROS (Negative). Large MSCs are significantly more likely to express aging markers. UL-Quad indicates the upper left quadrant (Q1), UR-Quad indicates the upper right quadrant (Q2-2), LL-Quad indicates the lower left quadrant, LR-Quad indicates the lower right quadrant.
Figure 6:
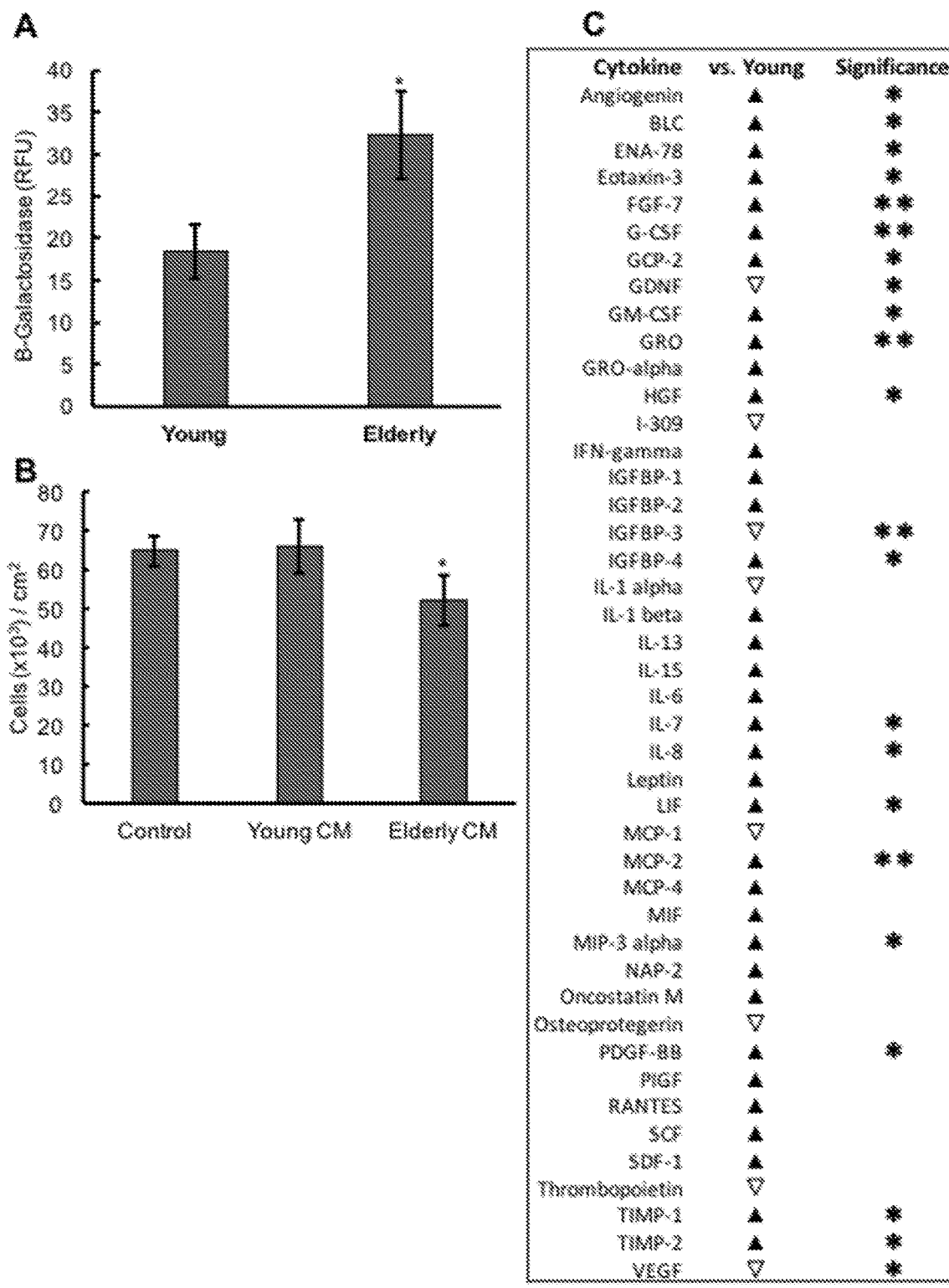
FIG. 6A-6C—Elderly MSCs are capable of inhibiting function of healthy cells through expression of the senescence associated secretory phenotype. (A) Elderly MSC populations have a substantially higher frequency of senescent cells relative to young MSC populations. (B) Conditioned media collected from elderly BM-MSCs contains factors that slow proliferation of young MSCs relative to controls. (C) Elderly MSCs secrete a cytokine profile indicative of the senescence associated secretory phenotype. The chart summarizes the cytokine expression of 44 SASP associated cytokines measured in elderly BM-MSCs relative to young BM-MSCs. *P<0.05, vs. young BM-MSCs. **P<0.01, vs. young BM-MSCs.
Figure 8:
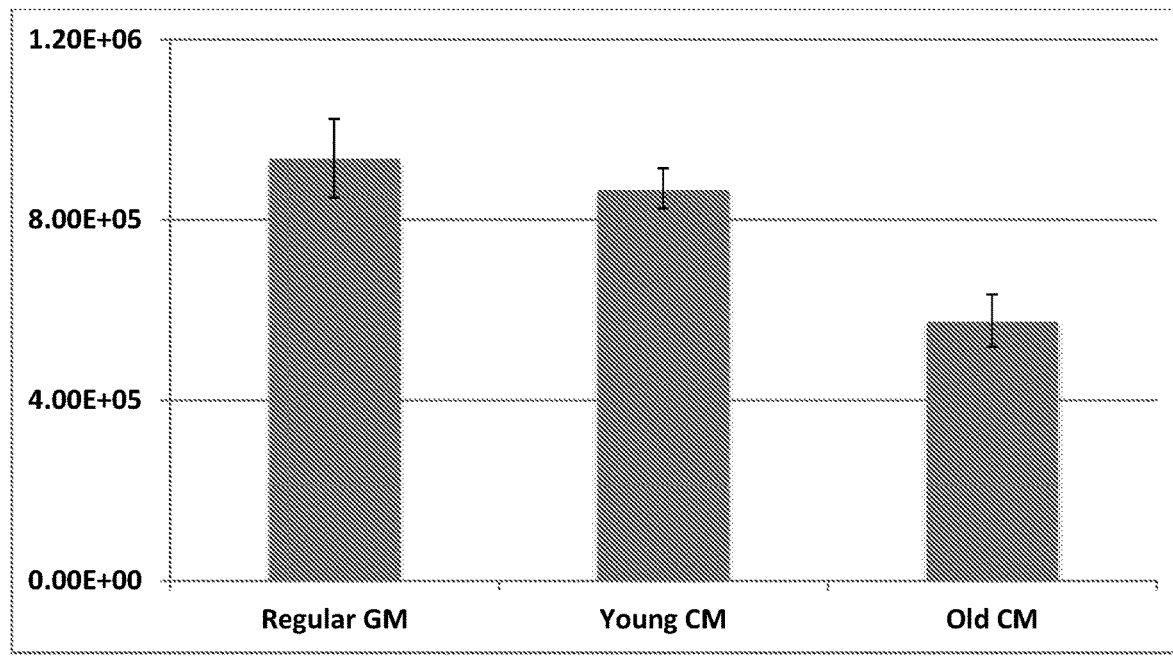
FIG. 8—Cell proliferation was determined for BM-MSCs from young donors grown in growth media (Regular GM as Control), growth media conditioned with secretions from young donor BM-MSCs (Young CM), and growth media conditioned with secretions from elderly donor BM-MSCs (Old CM). Elderly conditioned media inhibits proliferation of young MSCs. The proliferation rate of BM-MSCs from young donors was inhibited as determined by cell count after a set period of time when cultured in Old CM, while culturing in Young CM showed little to no difference.
Figure 16:
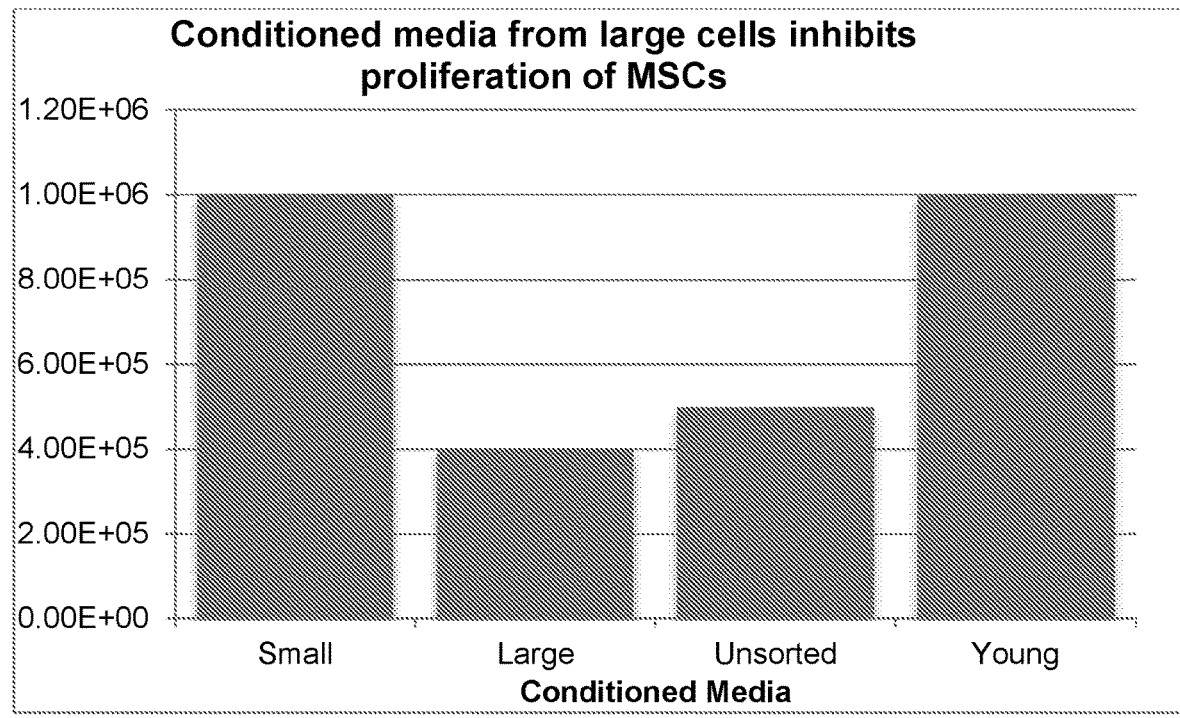
FIG. 16—Large cell size conditioned media inhibits proliferation of young MSCs. Cell proliferation was determined for MSCs from young donors grown in growth media conditioned with secretions from small size cells (Small), secretions from large size cells (Large), conditioned with secretions from cells unsorted by size (Unsorted), and growth media conditioned with secretions from young donor MSCs (young CM). The proliferation rate of MSCs from young donors was inhibited as determined by cell count after a set period of time when cultured in Large and Unsorted conditioned media, while culturing in Small and Young conditioned media showed little to no difference.

The phenotype of MSC cells from old and young donors are different, but there is overlap. See FIG. 1 and FIG. 4. The present inventors disclose herein that small BM-MSCs are more likely to express markers of early stage stem cells and large cells are more likely than small cells to express aging markers. See FIG. 2 for cells sorted based on size and the levels of ROS. Herein the inventors describe a small population of cells found in BM-MSCs isolated from older donors that are similar in size to the size of the BM-MSCs from young donors. See FIG. 3. The inventors disclose that the MSCs of small size from older donors may be more similar to young cells in several respects, including proliferation, differentiation, protein expression, and ROS profile. The inventors also disclose that the environmental conditions of the cells in older subjects may suppress proliferation capacities of the cells in older subjects. See FIGS. 6B, 8 and 16.

Figure 21A:
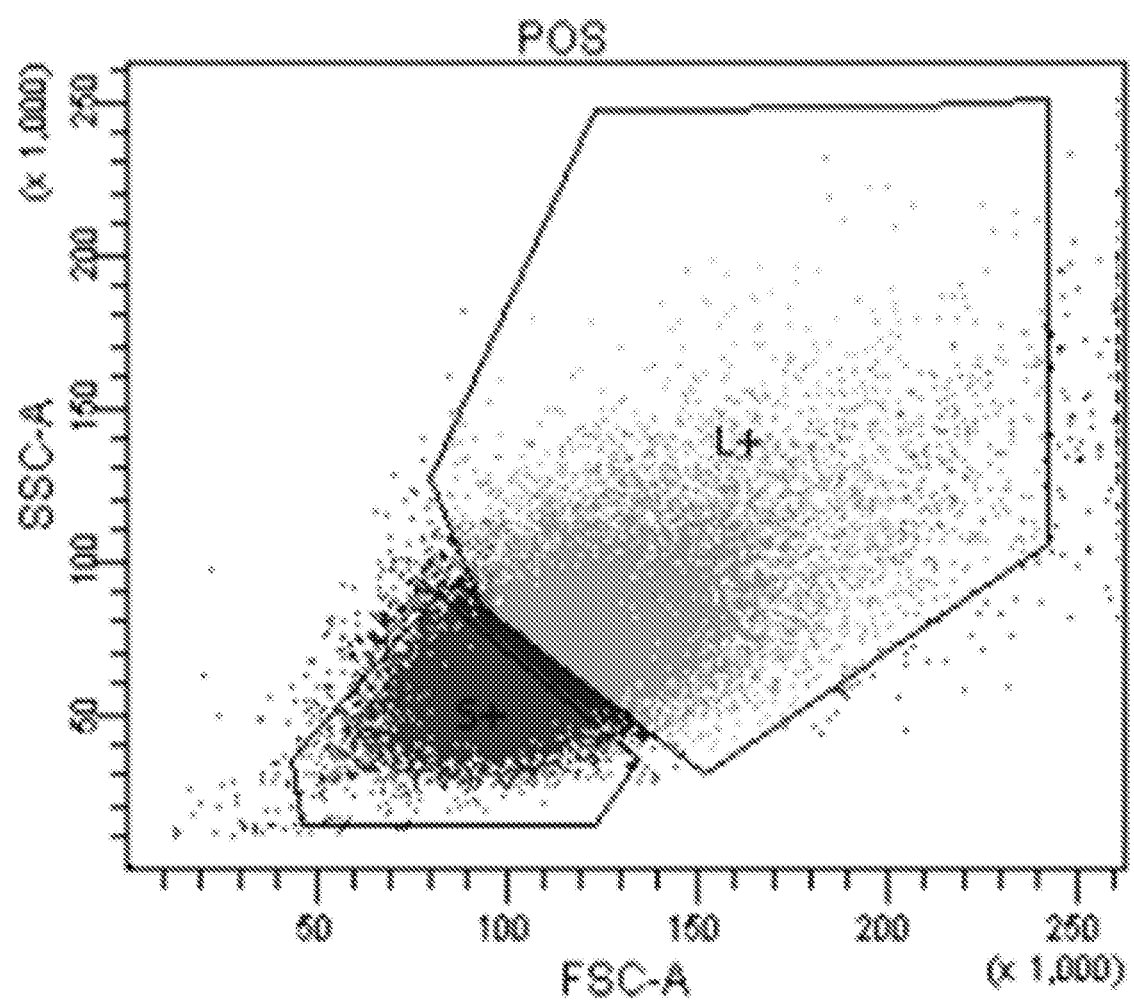
FIG. 21A-21C—Example gating strategy to obtain small cells that are SSEA-4 positive FIG. 22—Light microscopy micrographs of BM-MSCs subpopulations from a 71-year old male donor cultured on TCP and ECM derived from BM-MSCs from young donors (young ECM) for 7 days. Small cells positive for SSEA-4 showed an increase in cell proliferation under both conditions. Further, cells cultured on young ECM showed improvements in cell proliferation in comparison to cells cultured on TCP.
Figure 21B:
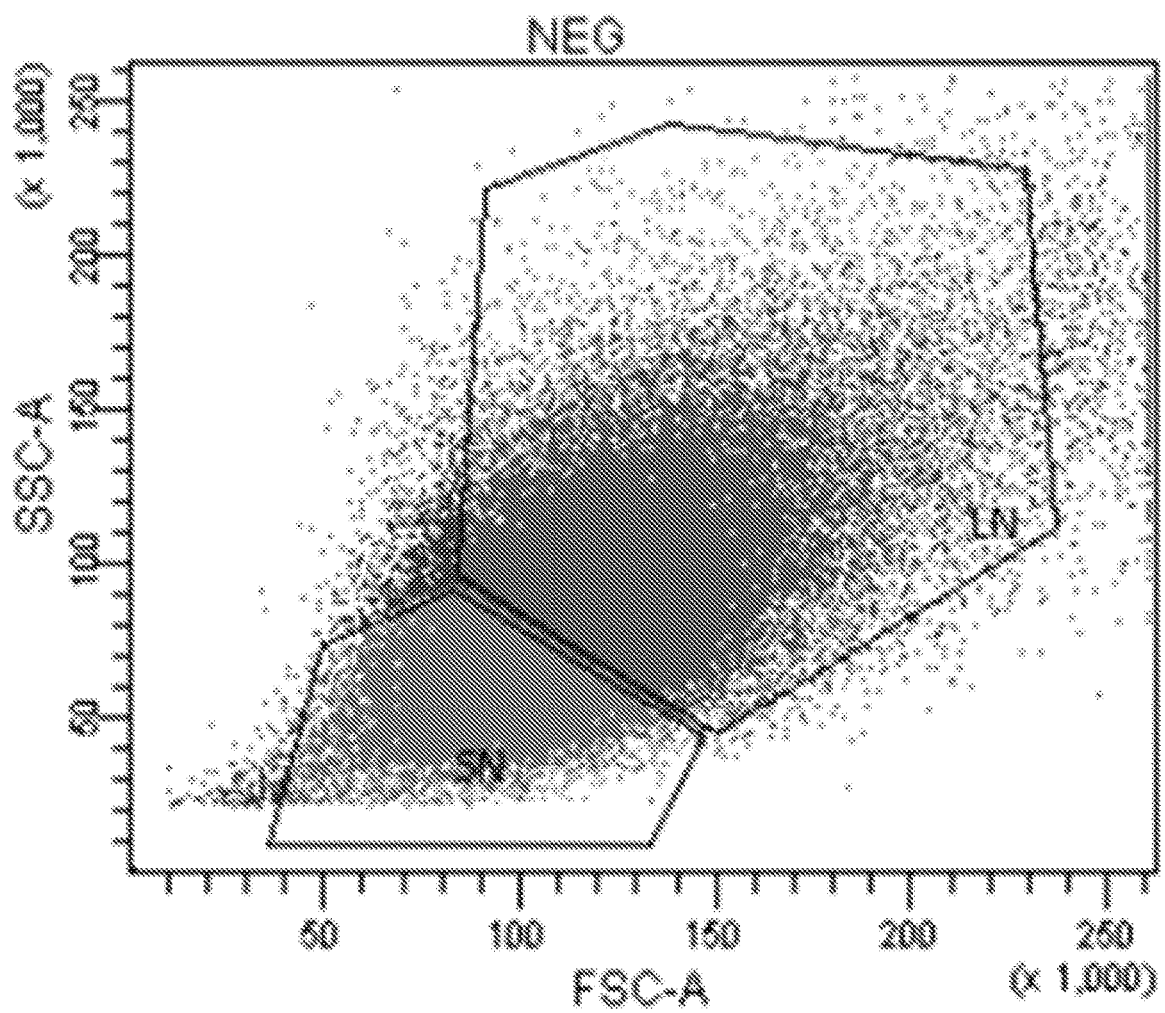
Figure 21C:
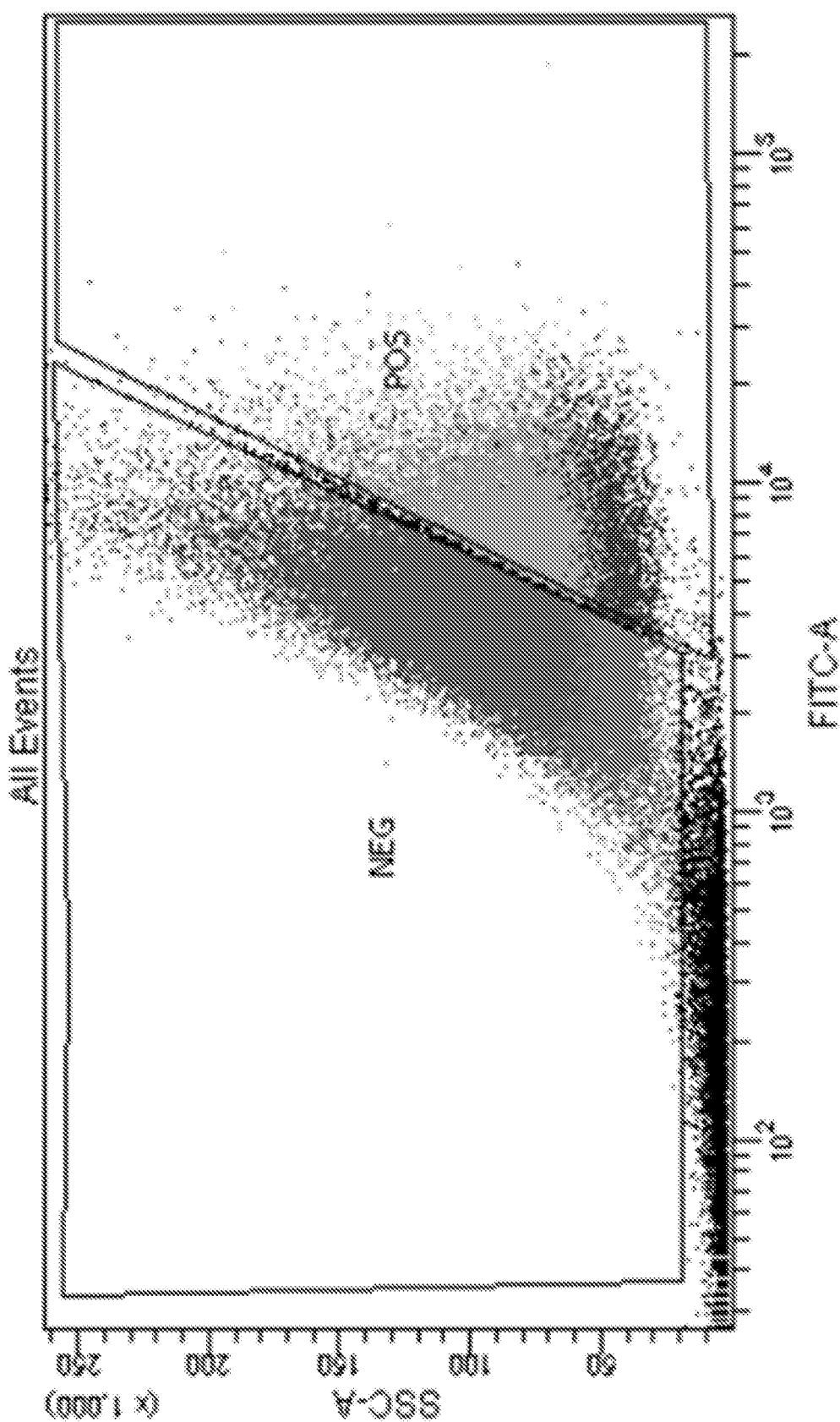

The inventors here disclose that to improve the performance of MSC cells isolated from a donor, it is desirable to isolate cells that are small in size and also express SSEA-4. See FIG. 21 for an embodiment of a gating strategy to obtain small cells that are SSEA-4 positive. This population more closely resembles cells from young donors in several properties that include an increased number of cells with higher ATP content, increased ATP content per cell, higher telomerase levels, lower β-Galactosidase expression, and a greater concentration of stem cells. See FIGS. 10, 11, 13 through 15.

The inventors further disclose that culturing the cells on ECM derived from BM-MSCs from young donors (young ECM) exaggerate the differences between the small cells that are SSEA-4 positive. See FIGS. 17 through 19 and 22 through 32.

The inventors also disclose that small cells that are SSEA-4 negative also appear to recover significantly when cultured on young ECM. This population is also valuable for clinical applications.

In one aspect, the disclosures herein can be used in adult autologous stem cell banking. With the techniques disclosed herein one may be able to find and expand healthy cells from anyone, regardless of age, for stem cell banking and future therapeutic applications. These techniques may be the strategy to rescue the regenerative capacity of aging stem cell populations, or make up part of the solution being used with a robust culture system. Stem cell banks, clinics, and adult patients with conditions that could potentially be treated with stem cells are non-limiting examples of groups that may find the invention useful. As a non-limiting example, using the discoveries disclosed herein, one may select only the best cells from clients for stem cell banking that will enable the banks to offer higher quality services, and/or offer services to individuals they would have previously assumed were too old.

Advantageously, disclosed herein are novel approaches that allow one to isolate and expand a small subpopulation of less defective MSCs from MSCs of low quality and quantity, such as the cells of elderly people. In one embodiment the less defective MSCs express stage-specific embryonic antigen 4 (SSEA-4) and/or are small in size. Further, disclosed herein are novel approaches to restore the regenerative capability of MSCs. This process provides a new paradigm for treating age-related disease. As a non-limiting example, serial administration of rejuvenated autologous BM-MSCs (by pre-exposure to our new culture system) may not only replace old BM-MSCs, but also gradually reverse the aged microenvironment. The ultimate goal is to slow the progression and/or reverse the degenerative effects of age-related degenerative diseases, disease and/or conditions or treatments that compromise the quantity or quality of MSCs or progeny cells thereof, or the aging process itself.

Non-limiting examples of age-related degenerative disease and diseases and/or conditions that compromise the quantity or quality of MSCs include, but are not limited to osteoarthritis and osteoporosis, sarcopenia, atherosclerosis, Parkinson's, Alzheimer's, xerostomia, macular degeneration, nonunion fractures, marrow ablation by chemotherapy or radiotherapy, and/or pneumonia.

Even in young cells, the focus of previous work aimed at isolating stem cells with greater purity has focused on using markers on the cell surface that have proven to be unreliable in most cases. The procedures disclosed herein enable one to isolate a sub-population of adult stem cells not previously recognized to be present. In some embodiments, the method comprises isolating healthy cells from a compromised population, such as a population from an elderly subject.

The studies described herein indicate that a small subpopulation of less defective BM-MSCs from aging bone marrow cells of elderly people can be isolated. Further, the proliferative capacity of BM-MSCs is remarkably improved by the provision of ECM made by BM-MSCs from young donors (young ECM). Based on the experimental data disclosed herein, it is expected that the differentiation capacity and the efficacy for tissue repair and regeneration will be increased in the subpopulation of less defective MSCs and will further be increased by culturing the cells on young ECM.

Cell size can be determined by means known by one of skill in the art. A non-limiting example includes determination of cell size by flow cytometry. In some instances, MSCs may be considered small if the cells have a smaller diameter when suspended in solution ("suspended diameter") than the average suspended diameter of the set of MSCs obtained from a donor at a given time.

In several aspects of the invention, disclosed are methods of obtaining and/or administering small size bone marrow-derived mesenchymal stem cells (BM-MSCs) to a subject, the methods comprising: harvesting a first set of BM-MSCs from a first donor; sorting the BM-MSCs by size and optionally SSEA-4 expression, isolating the small size BM-MSCs, plating the small size BM-MSCs for culture, expanding the small size BM-MSCs in culture, and administering the small size BM-MSCs to the subject. In some embodiments, the BM-MSCs are sorted using a flow cytometer. Optionally the expanded cells can be divided and/or stored in cell banks for future use. In some embodiments, the subject is the same as the first donor, and in these cases, the small size BM-MSCs would be autologous. In other embodiments, the small size BM-MSCs have a median diameter of less than 33 microns, or less than 30 microns, or less than 25 microns, or less than 20 microns, or less than 19 microns when measured in suspension. In some embodiments, the small size BM-MSCs expressed SSEA-4 (SSEA-4 +) at the time of isolation. In various embodiments, the subject is 50 years of age or older, 65 years of age or older, or 70 years of age or older. In some embodiments, the cells are cultured on TCP or on extracellular matrix (ECM) derived from a second set of BM-MSCs obtained from a second donor. In some embodiments, the second donor is 25 years of age or younger (providing "young" ECM). In other embodiments, the subject has decreased quantity and/or quality of BM-MSCs, and/or is in need of stem cell therapy. In still other embodiments, the subject has an age-related degenerative disease, and/or has a disease or condition that compromises the quantity or quality of BM-MSCs, and/or has or will receive treatments that compromise the quantity or quality of BM-MSCs.

In other aspects of the inventions, disclosed are compositions and/or cell culture systems comprising isolated small size BM-MSCs isolated from a first set of BM-MSCs obtained from a first donor, wherein the first donor was 50, 65, or 70 years of age or older at the time the first set of BM-MSCs were donated. In some embodiments, the small size MSCs expressed SSEA-4 (SSEA-4+) at the time of isolation. In some embodiments, the cell culture system does not comprise MSCs that were not small in size at the time of isolation. In some embodiments, the cell culture system does not comprise MSCs that did not express SSEA-4 at the time of isolation. In some embodiments, the isolated small size MSCs have a median diameter of less than 33 microns, or less than 30 microns, or less than 25 microns, or less than 20 microns, or less than 19 microns when measured in suspension. In other embodiments, the isolated small size MSCs were cultured on a ECM derived from a second set of BM-MSCs. In still other embodiments, the second set of BM-MSCs were obtained from a second donor 25 years of age or younger (young ECM). In various embodiments, the first donor had decreased quantity and/or quality of MSCs, and/or had an age-related degenerative disease, and/or had a disease or condition that compromises the quantity or quality of MSCs at the time the first set of MSCs were donated. For cell culture systems, the culture systems comprise a culture media. Suitable culture media are known by one skilled in the art. For compositions, the compositions may further comprise a carrier. Carriers can be aqueous based. The compositions and cell culture systems can comprise adjuvants, e.g., to preserve the composition or maintain the viability of the cells. Compositions and cell culture systems can be stored at cryogenic and/or hypothermic conditions, e.g., in cell banks, and can contain ingredients to aid in preservation at these conditions, e.g., cryoprotectants.

In some non-limiting aspects, the extracellular matrix (ECM) derived from BM-MSCs described herein can be produced by the methods disclosed in U.S. Pat. Nos. 8,084,023, 8,388,947, 8,961,955, and international patent application WO 2016/070057, all of which are herein incorporated by reference. The methods include producing a 3D ECM by culturing bone marrow stromal cells, which can include BM-MSCs, on TCP or carriers such as microcarriers, to produce the ECM, followed by decellularizing (lysing and/or washing/removing) the cells from the ECM. In various embodiments, the ECM comprises type I collagen, type III collagen, fibronectin, decorin, biglycan, perlecan, and laminin. In other embodiments, the ECM comprises type I collagen, type III collagen, fibronectin, decorin, biglycan, perlecan, and laminin, and further comprises at least one of syndecan-1, collagen type V, or collagen type VI. In other embodiments, the ECM comprises collagen alpha-1(XII), collagen alpha-3(VI), EMILIN-1, serpin HI, thrombospondin-1, tenascin precursor (TN) (Human), transforming growth factor-beta-induced protein, and vimentin. In still other embodiments, the ECM comprises collagen alpha-1 (XII), collagen alpha-3(VI), EMILIN-1, serpin HI, thrombospondin-1, tenascin precursor (TN) (Human), transforming growth factor-beta-induced protein, vimentin, type I collagen, type III collagen, fibronectin, decorin, biglycan, perlecan, and laminin. In still other embodiments, the ECM comprises collagen alpha-1(XII), collagen alpha-3(VI), EMILIN-1, serpin HI, thrombospondin-1, tenascin precursor (TN) (Human), transforming growth factor-beta-induced protein, vimentin, type I collagen, type III collagen, fibronectin, decorin, biglycan, perlecan, laminin, and further comprises at least one of syndecan-1, collagen type V, or collagen type VI.

Tissues produced in vitro yet retaining physiological features of in vivo tissues provide a particularly useful tool for monitoring the effects of proposed therapies or molecules on the physiological functions of the tissues. Accordingly, there is disclosed a method of testing the biological activity of a substance comprising obtaining any of the cell culture systems described above; adding the substance to the cell culture system; and measuring a parameter of the cell culture system or cells to determine the effect of adding the substance to the cell culture system. Adding the substance to the cell culture system can comprise adding the substance to the culture medium. The culture medium can be exchanged for a culture medium comprising a particular substance or combination of substances to monitor the effects of the culture medium change on the physiological functions of the cells. Measuring a parameter of the cell culture system can include, for example, observing growth rates or morphological features of cells. Any biologically relevant parameter can be measured and monitored to determine the biological effect of exposing the cells to a substance or of changing any conditions of growth. Changes in the parameter being measured or monitored can be attributed to the presence of the substance or the change in growth conditions if a corresponding control does not show the same change. In some embodiments, the substance being tested is a candidate therapeutic to treat a disease and/or condition, including, for example, age-related disease or the aging process itself. In some embodiments, the condition is reduced regenerative capacity of aging stem cell populations, or a side effect of a medication or radiotherapy. In some embodiments, the disease and/or condition is caused by or compromises the quantity or quality of MSCs. In some embodiments, the substance is a cellular growth factor or cellular differentiation factor.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Herein the inventors disclose that using the disclosed method allows one to isolate and expand a small subpopulation of less defective MSCs from bone marrow stromal cells of low quality and quantity, such as the cells of elderly people. Further, the inventors disclose novel methods to restore the regenerative capability of MSCs.

Example 1

Isolating and Culturing S+ BM-MSCS

Figure 7:
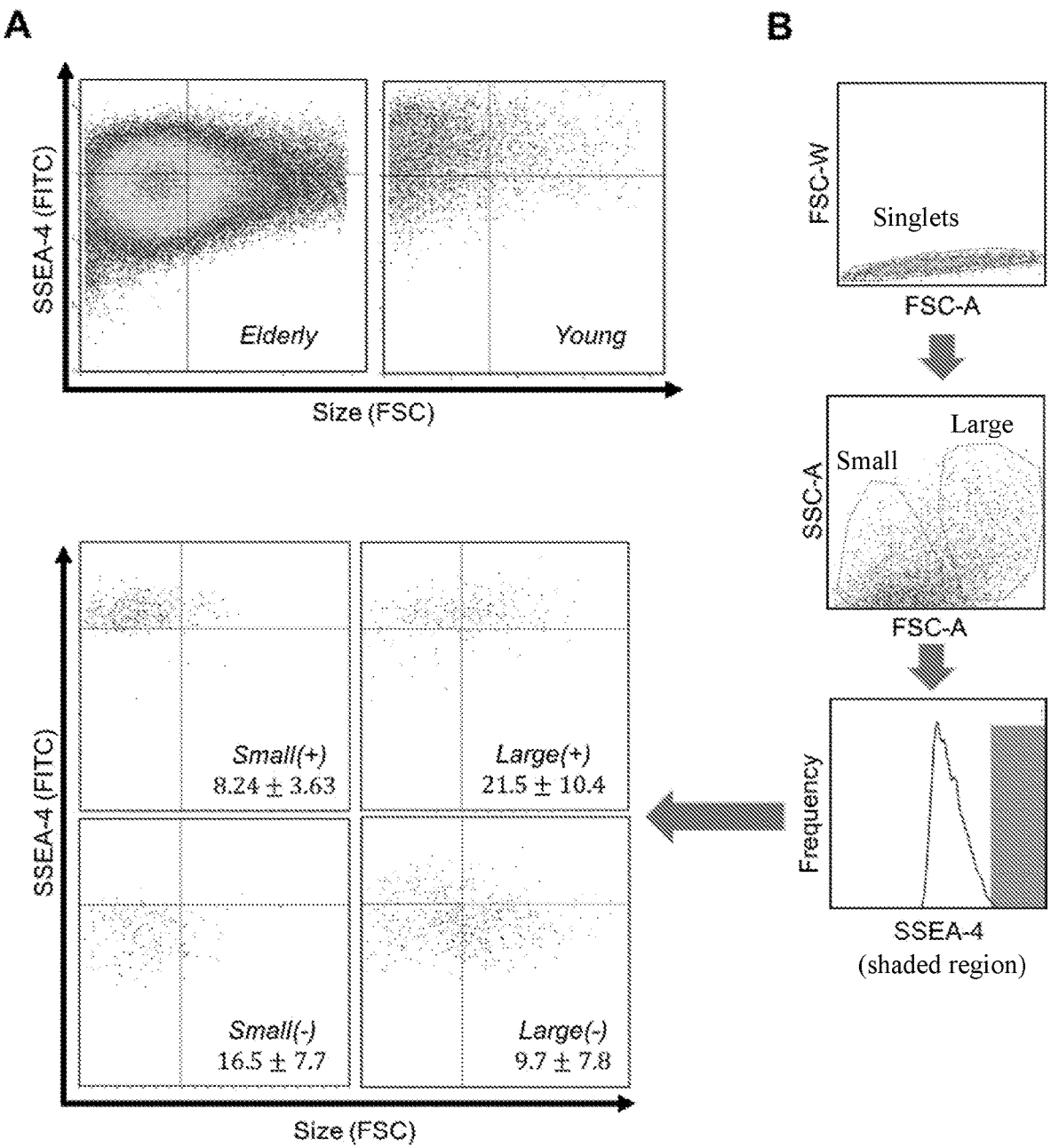
FIG. 7A-7B—Fluorescence activated cell sorting to isolate a youthful sub-population. (A) Flow cytometry reveals that while young BM-MSCs reliably express a small size, SSEA-4 (+) phenotype, elderly BM-MSCs are much more heterogenous along these dimensions. (B) Using FACS analysis enables one to obtain a "youthful" phenotype subpopulation from elderly donors. After doublet discrimination, cells are separated based on size (small vs. large) and SSEA-4 expression (positive vs. negative). Roughly 5-10% of elderly MSCs express the "youthful" (small (+)) phenotype.
Figure 20:
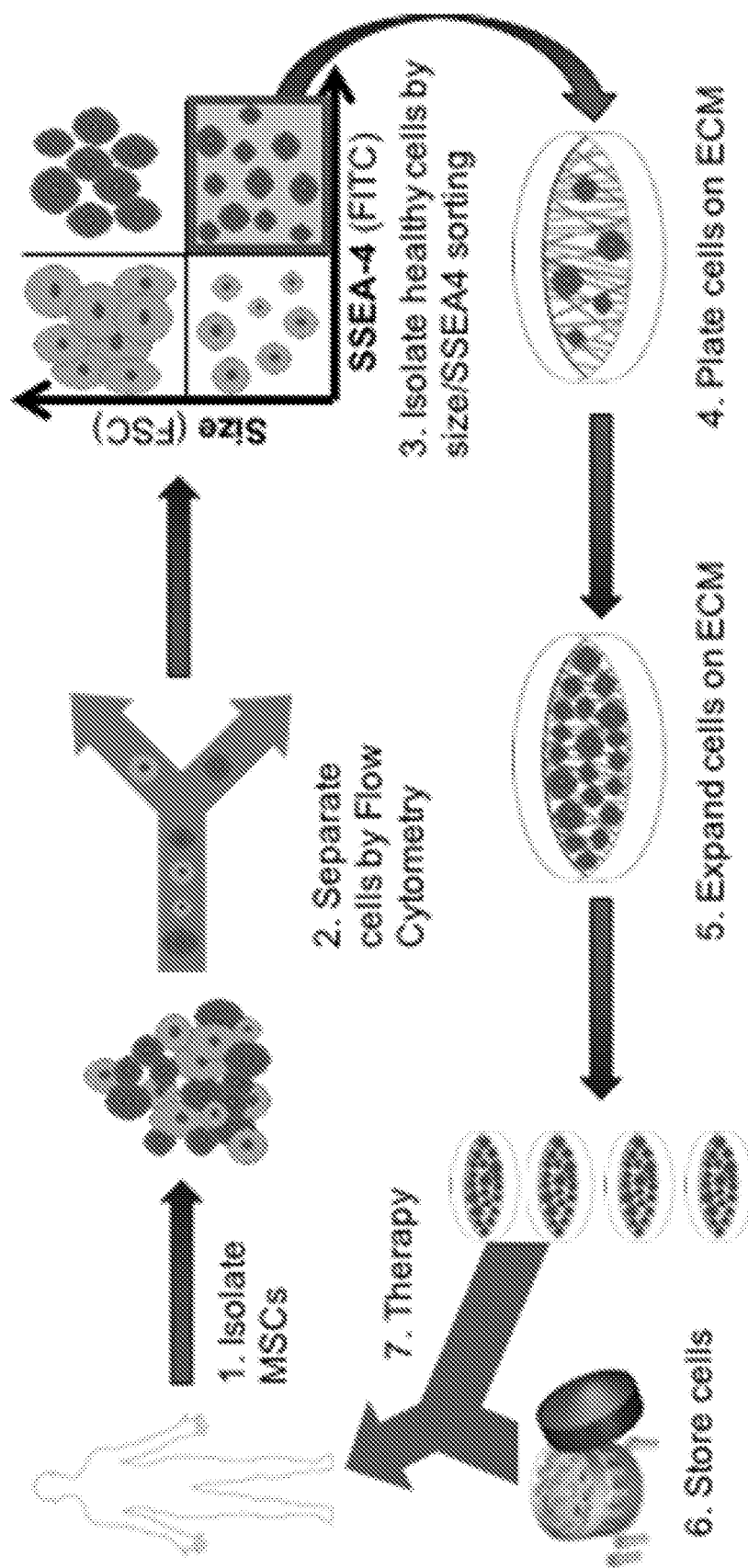
FIG. 20—Mesenchymal stem cells can be harvested from subjects with lower quality and quantity of MSCs. The cells are sorted by flow cytometry based on size and stage-specific embryonic antigen 4 (SSEA-4) expression. Small cells that are SSEA-4 positive (Small+) are plated on ECM made by marrow stromal cells from young donors (young ECM). The cells are then expanded using young ECM, divided, and stored. Using this approach, large numbers of "youthful" MSCs can be obtained from donors with lower quality and quantity of MSCs, such as elderly donors, for autologous MSC-based therapies and autologous MSC banking.

Bone marrow-derived mesenchymal stem cells (BM-MSCs) were harvested from elderly subjects (≥65 years old). The cells were sorted using flow cytometry based on size and SSEA-4 expression. Approximately 5% to 10% of the BM-MSCs harvested were small cells that are SSEA-4 positive (Small+). See FIG. 4 and FIG. 7. The inventors found that the Small+ enriched fraction after cell sorting was enriched in stem cells as determined by a colony forming units (CFU-F) assay compared to other subpopulations. The subpopulations were then plated on either ECM made by marrow stromal cells from young donors (≤23 years old) (young ECM) or TCP. BM-MSCs from young donors were used as a control. The cells were then cultured using the young ECM or TCP and compared based on self-renewal, immunophenotype, and differentiation capacity. After culturing, the cells were divided and stored. FIG. 20 illustrates an embodiment of the general approach explained above.

Briefly, BM-MSCs were seeded onto TCP or young ECM at 3,000 cells/cm$^2$ and cultured for 7 days. FIG. 4A, shows a brightfield microscopy of cells in culture at day 6. Young mesenchymal stem cells (MSCs) appear to have a greater number of cells and display a more spindle-like morphology relative to elderly cells. For elderly cells, there is no substantial difference in the total number of cells, nor the overall appearance for culture on TCP vs. ECM. This is substantiated by the density of cells after 7 days of culture (FIG. 4B). Cell counts demonstrate that young cell proliferate significantly more on ECM relative to TCP ($p=0.015$), whereas small differences observed in the cell density of elderly MSCs were not statistically significant ($p=0.0781$). This is inconsistent with previously reported observations in a mouse model, where proliferation of elderly MSCs increased 2-fold on young ECM.

After 7 days culture, cells were detached and reseeded at clonal density on TCP for colony forming unit-fibroblast (CFU-F), -adipocyte (-AD), and -osteoblast (-OB) assays or used for immunophenotyping by flow cytometry. As demonstrated in FIG. 4C, colony formation and differentiation by elderly BM-MSCs is not substantially impacted by pre-expansion on ECM. Furthermore, colony formation in both groups is less than young BM-MSCs. In contrast, young BM-MSCs pre-expanded on ECM formed larger, denser, and more numerous colonies in each condition. While proliferation and differentiation assays reveal clear differences between the 4 groups, no differences were apparent in the standard surface markers associated with MSCs. Expression of CD73, CD90, and CD105 were similar for either culture condition and for both age groups (not shown). This is consistent with suggestions that expression of MSC markers remain high regardless of age and/or differentiation capacity (Bonab, et al, 2006). The elderly BM-MSCs' replication and osteogenesis were not reliably rescued by culture on young ECM.

Materials and Methods: The materials and methods used in this and the following Examples are briefly described below:

Bone Marrow from Young Donors—Bone marrow from young donors was purchased from LONZA (Walkersville, Md., USA). Bone marrow samples were obtained from healthy, male donors under the age of 23. Fresh, unprocessed samples were shipped overnight on ice and upon receipt, red blood cells were lysed and mononuclear cells seeded onto TCP vessels ($5\times10^5$ cells/cm$^2$) in standard growth media (composition described below). When colonies began to form, media were removed, non-adherent cells washed away gently using PBS, and fresh media added. These cells were expanded for one or two passages (P1, P2) and used in the experiments. Alternatively, for future use, the cells were stored in liquid nitrogen at $2\times10^6$ cells/mL in 20% serum containing media+10% (v/v) dimethyl sulfoxide (DMSO). Cells used in these studies came from 5 different donors.

Bone Marrow from Elderly Donors—Bone marrow cells from elderly donors (age 65 or older) were obtained from consenting patients undergoing a total knee/hip replacement. Cancellous bone from the surgical site was removed and immediately placed into isolation buffer (Hank's Buffered Saline Solution+5% (v/v) fetal bovine serum) at 4° C. Clinical samples were brought back to the lab within 3-4 hours of removal from the patient, cut into small pieces using sharp scissors at 4° C., and then digested for 30 minutes using collagenase type 2 (400 units/mL) dissolved in phosphate buffered saline (PBS) at 37° C. with agitation. At completion, the digest was centrifuged (600×g) for 5 minutes at 4° C. and the supernatant removed. The pellet was then resuspended in isolation buffer and filtered through a 100 micron cell strainer to remove bone fragments. The bone fragments, collected on the cell strainer, were washed until bright white in color. The remaining solution, containing the cells, was centrifuged (600×g) for 5 minutes at 4° C. and the cell pellet resuspended in growth media. Cells were seeded ($5 \times 10^5$ cells/cm$^2$) into TCP vessels in growth media and cultured under standard conditions until colonies began to form. Once colonies appeared, full media were removed, non-adherent cells gently washed away using PBS, and fresh media added. These cells were expanded (P1, P2) and used immediately in experiments or placed in liquid nitrogen for future use. Cells from 13 donors were tested, but only 11 were used. Two donors were not utilized because the phenotypic composition did not permit sorting sufficient numbers of cells into all 4 sub-populations.

Extracellular Matrix—Bone marrow derived extracellular matrix was provided by StemBioSys, Inc. (San Antonio, Tex., USA).

Cell Culture—Bone-marrow MSCs were cultured in a humidified incubator at 37° C. and 5% $CO_2$. Unless indicated otherwise, cells were cultured in "standard growth media" containing α-Minimal Essential Medium (MEM), 15% pre-selected FBS (Atlanta Biologics, Flowery Branch, GA, USA), 2 mM L-glutamine (Life Technologies, Grand Island, N.Y., USA), and 1% (v/v) streptomycin/penicillin (Life Technologies, Grand Island, N.Y., USA). One-half media changes were performed every three days during culture.

Colony forming unit assays—For CFU-fibroblast (CFU-F) assays, cells were seeded onto 6 well plates at 10 and 30 cells/cm$^2$ in standard growth media. When dense colonies formed (typically, culture day 10-14), media were removed, wells washed one time with PBS, and cells fixed at room temperature (100% methanol for 10 minutes). After fixation, cells were washed once with PBS and allowed to dry at room temperature for 10 minutes. Colonies were then stained with methyl violet (MP Biomedicals, Solon, Ohio, USA) for 10 minutes. Staining solution was collected for reuse and residual stain washed away with deionized water until the background appeared clear.

For CFU-Adipocyte (AD) and Osteoblast (OB) assays, cells were seeded onto 6 well plates at 20 and 60 cells/cm$^2$. CFU-AD and CFU-OB cultures were started at the same time as those for CFU-F assays. At the time of staining the CFU-F plates, CFU-AD and -OB plates were switched to their respective induction media. For CFU-AD cultures, media were supplemented with 5 mM 3-isobutyl-L-methylxanthine (IBMX), 1 mM indomethacin, 1 µM dexamethasone, and 10 µg/mL insulin. For CFU-OB cultures, media were supplemented with 100 nM dexamethasone, 10 mM β-glycerophosphate, and 50 µM L-ascorbic acid 2-phosphate. All media supplements for AD and OB induction were purchased from Sigma-Aldrich (St. Louis, Mo., USA).

CFU-AD and -OB plates were stained when colonies were visually observed to contain lipid or mineral, respectively, as observed by light microscopy. This was typically after 10-14 days for adipogenesis or 17-21 days for osteogenesis. CFU-AD cultures were stained by fixing the cells for 1 hour at room temperature with 10% formalin, followed by gentle washing with deionized water before staining with freshly prepared Oil Red O for 1 hour at room temperature. After staining, the solution was removed and the wells washed gently with deionized water until the background was clear. For CFU-OB, cells were fixed at room temperature for 1 hour using 10% formalin, washed with deionized water, and then stained with 1% silver nitrate ($AgNO_3$) overnight at room temperature under ultraviolet light. The next day, the $AgNO_3$ solution was removed and excess silver removed by treating with 5% sodium thiosulfate for 2 minutes. Wells were then washed with deionized water to prevent removal of excess stain.

Fluorescent Activated Cell Sorting—Fluorescein isothiocyanate (FITC) conjugated anti-SSEA-4 and IgG3 isotype control antibodies were purchased from BD Biosciences (San Jose, Calif., USA). The gating strategy for selecting small and large BM-MSC populations was developed over a period of weeks using cells from a variety of young and elderly donors, with young donor cells serving as a control for small cells. The voltage and gating for size, based on forward scatter (FSC), was kept constant for all cell sorts. FITC gating was reassessed each time based on our isotype control. Doublet discrimination was used to remove cell doublets.

Staining was performed on single cell suspensions (10× $10^6$ cells/mL) using antibody at 10 µg/mL and incubation for 1 hour at 4° C. Cells were washed twice with isolation buffer and placed on ice (<3 hrs) until subjected to sterile sorting using the FACSAria Cell Sorter from BD Biosciences (San Jose, Calif., USA). The sorting was run using the FACSDiva software system.

Flow Cytometry—Mouse-anti-human non-conjugated antibodies were purchased from BD Biosciences (San Jose, Calif., USA). Single cell suspensions ($1 \times 10^5$ in 100 µL) were incubated for at least 1 hour at 4° C. with primary antibody (10 µg/mL). Stained cells were washed twice with staining buffer (PBS+5% v/v FBS+0.01% m/v sodium azide) prior to incubation with FITC conjugated goat anti-mouse IgG for 30 minutes at 4° C. The cells were then washed twice with staining buffer and either immediately analyzed or fixed with freshly prepared 1% paraformaldehyde and analyzed within 72 hours. Analysis was performed using a BD Bioscience LSRII flow cytometer. Samples were run using the FACSDiva software system, and data generated were later analyzed and figures created using the FlowJo software package. 10,000 events were analyzed for each sample and the primary outcome was percent positive cells relative to isotype control. The described protocol was modified to include dimethyl sulfoxide with antibody to permeabilize membrane when assaying for annexin-5.

Median Diameter—Following culture, cells were detached and placed into suspension. Suspended cells were spread on a glass slide, underneath a coverslip. Images were taken of brightfield microscopy and analyzed using Olympus CellSens software to analyze the spread morphology for at least 100 cells in each condition. For elderly cells, n=150; for young cells, n=276. Descriptive statistics were calculated using MATLAB technical computing software.

Intracellular Reactive Oxygen Species—Intracellular reactive oxygen species (ROS) were analyzed using the CellROX green flow cytometry assay kit (ThermoFisher Scientific, Bedford, Mass., USA). Three tubes were prepared, each with 5×10$^5$ cells/mL in roughly 100 µL. To a negative control tube, 1 mM N-acetylcysteine (NAC) was added to increase the antioxidant capability of the sample. For a positive control tert-butylhydroperoxide (TBHP; 200 µM) was used to induce oxidative stress. All three tubes were incubated at 37° C. for 1 hour before staining with CellROX ROS detection reagent. Stained samples were immediately analyzed (within 1 hour) using the BD Bioscience LSRII flow cytometer.

Adenosine Triphosphate—Adenosine triphosphate (ATP) levels were measured using the ATP Determination Kit (Molecular Probes, Eugene, Oreg., USA). 25,000 cells from test cultures were measured in triplicate and compared to an ATP standard curve created using an ATP standard supplied with the kit. Luminescence was due to the activity of firefly luciferase and an average ATP concentration for each sample was determined using the standard curve.

Beta-Galactosidase—β-Galactosidase (β-Gal) was measured using a 96-well Cellular Senescence Assay Kit (Cell Biolabs, San Diego, Calif., USA).

Cells in a 96-well plate were incubated with cell lysis buffer at 4° C. for 5 minutes. The whole cell lysate was transferred to a microcentrifuge tube and centrifuged at 2,000×g for 10 minutes. The supernatant of the cell lysate was collected for analysis. 50 µL samples were incubated at 37° C. with 50 µL of freshly prepared assay buffer (supplied with kit) for 3 hours protected from light. After 3 hours, 50 µL of the reaction solution was added to 200 µL of stop solution in a 96 well plate. Fluorescence was measured immediately at 360 nm excitation/465 nm emission.

Telomerase Activity—Telomerase activity was quantified using the TeloTAGGG Telomerase PCR ELISA$^{PLUS}$ kit (Roche Diagnostics, Indianapolis, Ind., USA). The assay kit is a two-step process. In the first step, telomerase adds telomeric repeats to the end of a biotin-labeled primer, and then the primer and elongation products are amplified by PCR. In the next step, the PCR products are hybridized to digoxigenin-(DIG)-labeled detection probes, specific for the telomeric repeats, and then immobilized via the biotin label to a microplate. They are then detected with an antibody conjugated to horseradish peroxidase (HRP). Using absorbance values of the sample, as well as all of the experimental controls, one is able to calculate relative telomerase activities for different samples within a given experiment.

Cell Morphology—Images were taken using an Olympus IX73 Inverted Microscope (Olympus, Shinjuku, Tokyo, Japan) at various stages of cell proliferation. For measurements of cell morphology, images were taken at pre-confluence so that cell morphology would not be substantially influenced by cell-cell contacts. Images were analyzed using the CellSens Dimension software by Olympus. Cells were outlined using the freehand polygon tool; measurements of circularity and area were automatically calculated.

Statistical Analysis—Cell counts, CFUs, β-Galactosidase, ATP, and Telomerase assays were performed in triplicate per independent experiment. Flow cytometry was performed once for each marker in each group in each independent experiment. All types of experiment were repeated at least 3 times using cells from different tissue donors.

The replicate data for each assay were pooled (i.e. proliferation, CFU assays, Telomerase activity, ATP levels, and gene expression) and then analyzed. Mean, standard deviation, and confidence intervals were calculated and groups compared using ANOVA analysis and post-hoc tests when necessary.

Differentiation capacity was calculated as proportions of CFU-AD and -OB to CFU-F, and confidence intervals determined using a modified Wald method.

Flow cytometry data, because of the very large sample size, were assumed to represent the number of cells expressing various markers in the entire population. Results from different donors within groups were averaged and compared using ANOVA as described for the proliferation studies. Fisher's exact test was used to determine whether or not large cells were more likely than small cells to express markers of aging.

Example 2

Distinguishing Morphological Differences and Expression of SSEA-4

Properties of young and elderly BM-MSCs were compared and contrasted to identify properties that can serve as limiting factors in preventing the rescue of elderly MSC populations, and to identify assays that most reliably illuminate differences between young and elderly MSCs so that those properties of young MSCs may be used as a benchmark for measuring the function of other MSCs populations.

The proliferation rate of elderly MSCs is much slower relative to young MSCs. See FIG. 4. Additionally, the morphological phenotype of elderly BM-MSCs appears larger and less spindle-like relative to young MSCs. See FIG. 4. Morphological differences, however, may simply be a result of cell-cell contact due to the degree of confluence of the younger cells. To determine whether these morphological differences are present prior to young BM-MSCs reaching confluence, images were taken after 3 days in culture, when the effects of cell-cell contacts are minimal. Large differences in the morphology of young vs. elderly BM-MSCs were seen qualitatively by brightfield microscopy prior to cells reaching confluence. See FIG. 5A. This difference can be quantified by comparing the ratio of the cells spread area to the ratio of a circle with equivalent perimeter (circularity). Elderly BM-MSCs are >25% more circular (less spindle-like) relative to young MSCs ($p < 0.00001$).

Figure 5:
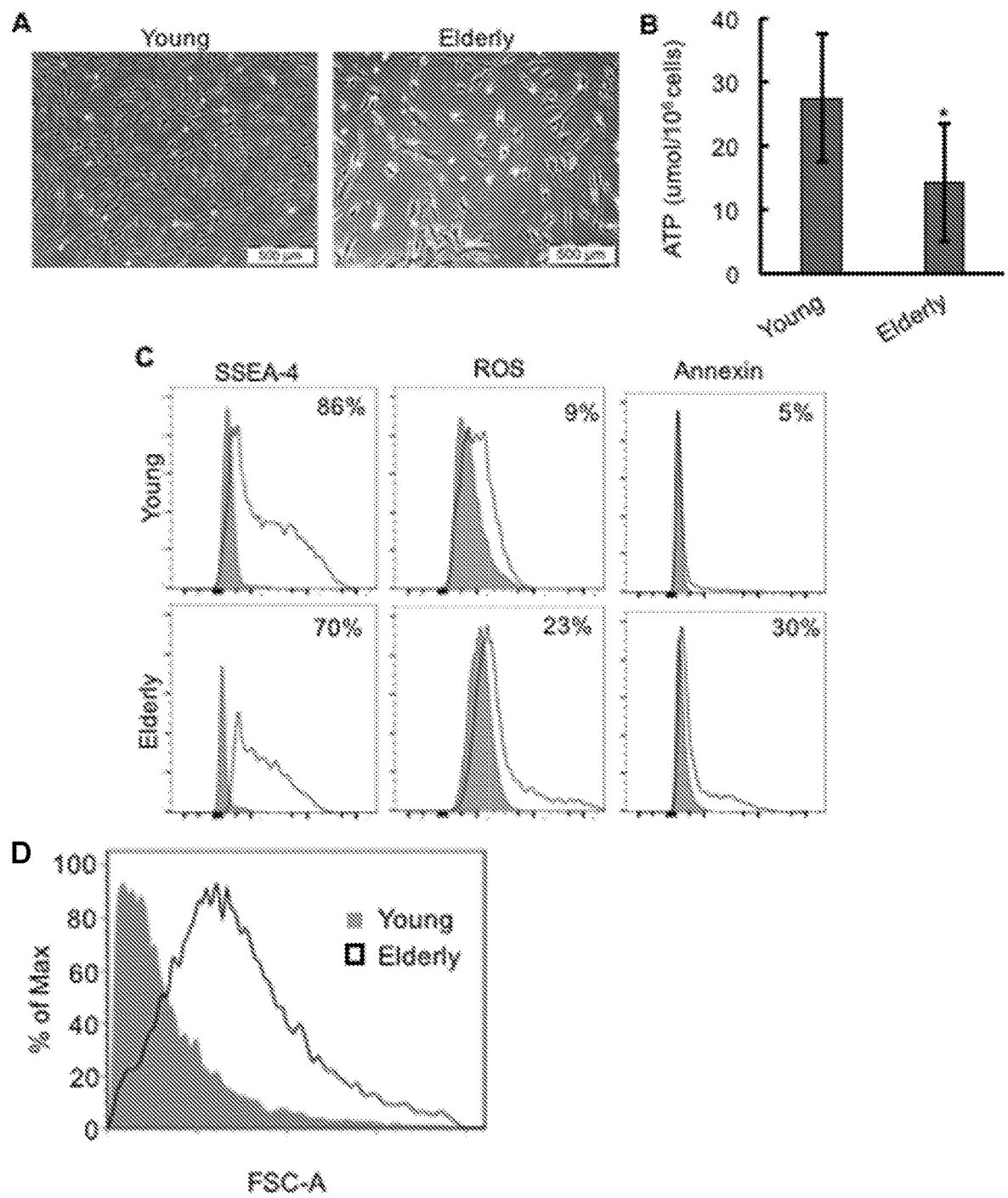
FIG. 5A-5D—Young and elderly MSCs may be distinguished across a variety of parameters. (A) Young and elderly BM-MSCs were imaged in culture by light microscopy prior to reaching confluence. Elderly MSCs have a much larger, rounder, flatter spreading pattern. (B) ATP concentration of young and elderly BM-MSCs was measured. Young MSCs have roughly 2-fold more ATP than elderly MSCs. (C) Young and elderly BM-MSCs were analyzed by flow cytometry after culture. Some fraction of elderly MSCs express high levels of annexin-5 and intracellular ROS. Though elderly MSCs express lower levels of SSEA-4, a substantial fraction do express SSEA-4. In each graph the sample (black line) was compared to a negative control (shaded region) in order to quantify expression. (D) Size of cells in suspension was measured using the forward scatter parameter in flow cytometry. The distribution of cell sizes mirrors that of cell spread area. *P<0.05, vs. young MSCs on the same substrate.

After measuring differences in cell shape during culture, the differences in the metabolic activity of young and elderly BM-MSCs were explored. Elderly BM-MSCs were shown to contain levels of ATP roughly 50% lower that of young BM-MSCs ($p = 0.023$) (FIG. 5B). This is unsurprising and metabolic activity is known to decrease with age. Additionally, as many cellular processes require energy in the form of ATP, it is possible that this reduction is critical to the age-related loss of function observed in MSCs.

As MSCs are known to be a heterogeneous population, and a number of recent studies in hematopoietic cells have described population level aging in cells as a shift in the clonal composition rather than aging of all cells individually. Extensive immunophenotyping was performed to understand the phenotypic composition of elderly BM-MSC populations relative to young. No differences were seen in traditional immunophenotypic markers for BM-MSCs; however, several differences in expression of markers correlated with stemness and aging via flow cytometry (FIG. 5C). Despite diminished metabolic activity, a significant number of elderly BM-MSCs have very high intracellular reactive oxygen species (ROS) content. This suggests that these cells have substantially diminished capacity for eliminating intracellular ROS. While it is unclear whether a causal link exists in this scenario, a similar fraction of cells also express annexin-5, an early apoptotic marker. This suggests that a sizeable portion of elderly MSCs in culture are preparing to undergo apoptosis. Not to be bound by theory, this is one possible explanation for the relatively large portion of elderly BM-MSCs expressing SSEA-4.

SSEA-4 has been used as a marker of potent MSCs, and may be a reliable marker of stemness (Sun, et al., 2011; Gang, et al., 2007; Kawanabe, et al., 2014; Pipino, et al., 2015). However, if this is true, one might expect that in populations of cells with a relatively small fraction of SSEA-4 (+) MSCs, the SSEA-4 phenotype would become the dominant phenotype by proliferating more quickly than other cells. In practice, this is not the case. In elderly MSC populations, SSEA-4 expression tends to decrease during serial passage, and the culture eventually fails. Not to be bound by theory, if a large fraction of MSCs in elderly donors are undergoing apoptosis, it could be that the rapidly dividing cells are also rapidly apoptosing, preventing them from becoming the dominant phenotype of the culture.

Figure 3:
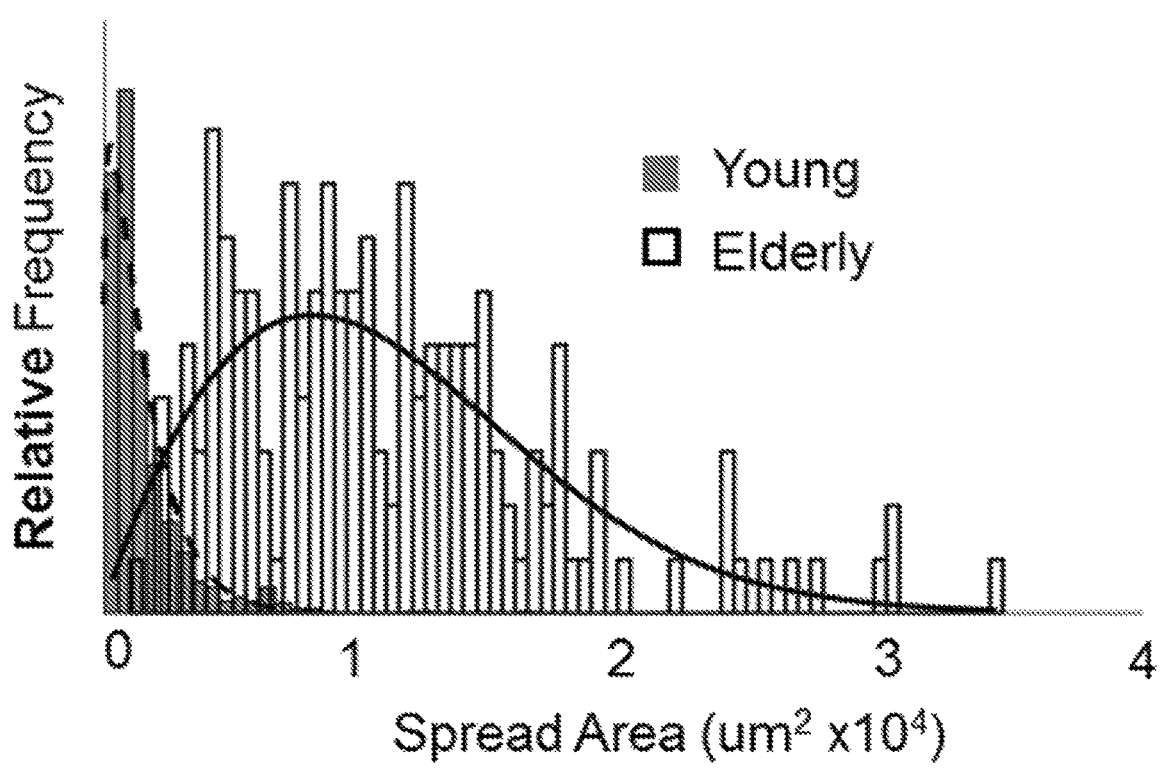
FIG. 3—Cell spread area was measured for cells in culture on TCP. The spread areas of young and elderly BM-MSCs are reported here as a relative frequency of BM-MSCs at different spread areas. Median spread area is substantially larger for elderly MSCs relative to young.
Figure 4:
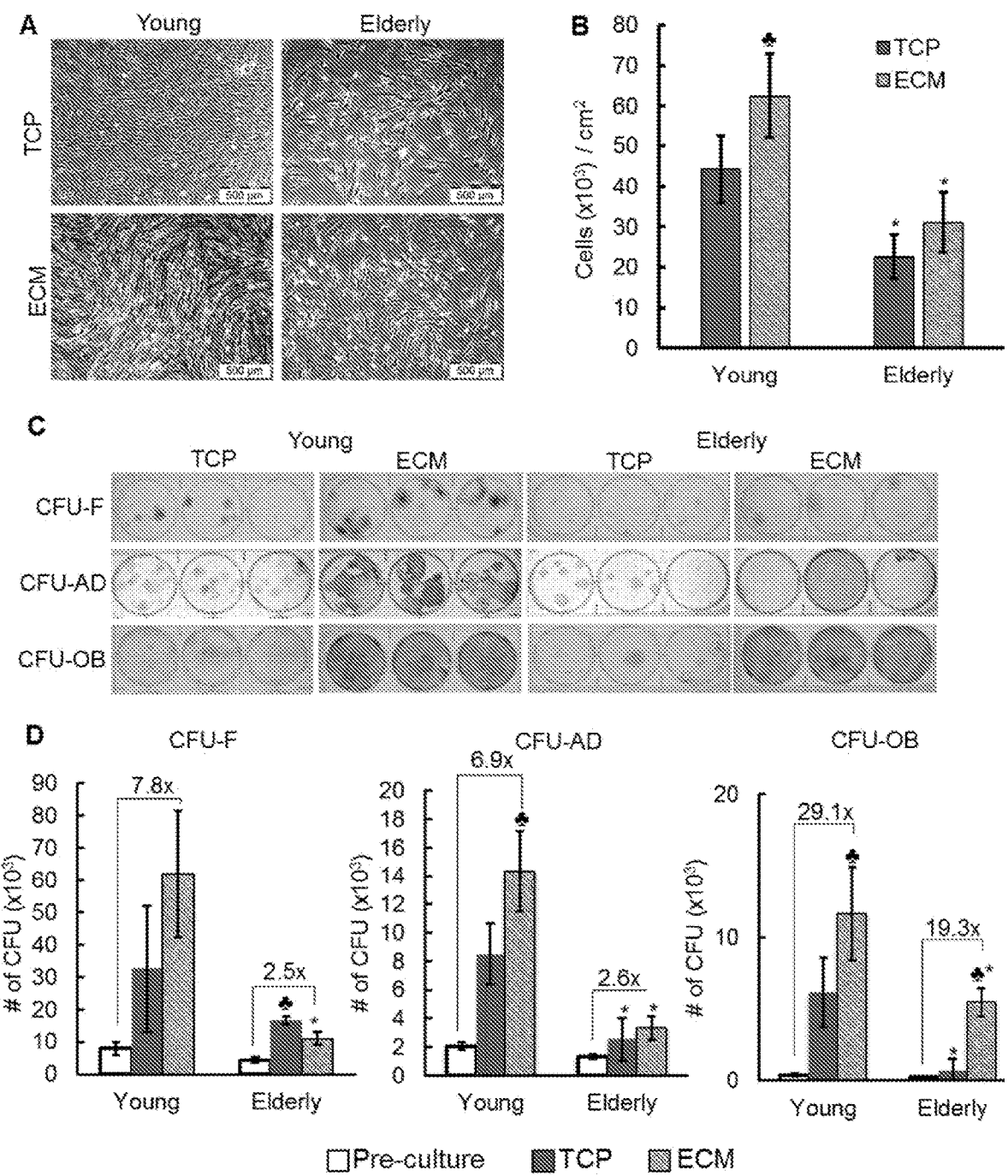
FIG. 4A-4D—Young ECM benefits MSCs from young, but not elderly, donors. (A) Young and elderly BM-MSCs were imaged in culture after 6 days by light microscopy. Young BM-MSCs cultured on ECM appear highly confluent. Elderly BM-MSCs, regardless of substrate remain sparse after 6 days of culture. (B) Cells were detached and counted after 7 days culture in order to determine cell density. (C) After counting, cells were reseeded at clonal density for colony forming unit assays. (D) Total numbers of CFUs were calculated by multiplying average CFU frequency by the total number of cells. *$P<0.05$, vs. young BM-MSCs on the same substrate. ♣ $P<0.05$, vs. the same population of cells cultured on TCP. (n=11)

A second possible explanation is suggested by the morphology of elderly BM-MSCs. In addition to a change in shape, elderly BM-MSCs have much higher median spread area (14,326 $\mu m^2$ vs 2,123 $\mu m^2$) and median diameter (33.10 $\mu m$ vs 18.20 $\mu m$—Table 1). The distribution of cell spread area and cell size (as measured by forward scatter in flow cytometry) of elderly and young BM-MSCs are shown in FIGS. 3 and 5D, respectively. While the median size appears to be substantially larger in elderly MSCs relative to young, there is significant overlap, between the populations, and they appear to occupy a similar range. The BM-MSCs of small size from the elderly donors are similar in size to the size of the BM-MSCs found in young donors. The changes in cell size and shape observed here for the BM-MSCs from elderly donors are characteristic of cells acquiring a senescent phenotype (Zhou, et al., 2008, Wagner, et al., 2008). Over the past decade significant progress has been made in the understanding of the role of senescence in aging. Much of this has centered on identifying pleiotropic mechanisms and showing that senescent cells may harm neighboring cells via paracrine effects through what has been dubbed the senescence associated secretory phenotype (Campisi, et al., 2011; Freund, et al., 2010; Coppé, et al., 2008). Not to be bound by theory, it is possible, that if these larger, flatter, more circular cells have become senescent that they are inhibiting "youthful" neighboring cells via secreted factors.

TABLE 1

|  | Median Diameter ($\mu m$) | Standard Dev. |
|---|---|---|
| Young | 18.20 | 1.50 |
| Elderly | 33.10 | 4.90 |

Example 3

Identification of Increased Secreted Factors From Old BM-MSCS Cells and Their Effects on Cell Proliferation To test whether or not it is plausible that elderly MSC populations contain a subpopulation of "youthful" MSCs that are inhibited by soluble factors secreted by senescent cells, the population of senescent BM-MSCs in elderly populations and young populations was determined.

To compare relative numbers of senescent cells in young and elderly populations, equal numbers of young and elderly BM-MSCs were collected and β-Galactosidase expression was measured. β-Galactosidase expression is a marker of senescence. BM-MSCs from elderly donors have a higher frequency of senescent cells than that of young BM-MSCs. (FIG. 6A) (p=0.017).

Next, young BM-MSCs were treated with conditioned media collected from young or elderly MSCs to determine whether secreted factors from elderly BM-MSCs are capable of inhibiting the function of "youthful" MSCs. Conditioned media from elderly MSCs (Elderly CM) significantly inhibits the proliferation of young BM-MSCs relative to control or conditioned media from young BM-MSCs (FIG. 6B) (p=0.004 or p=0.007, respectively). See also FIG. 8. Not to be bound by theory, this data is sufficient to permit the possibility that elderly MSCs may contain a "youthful" subpopulation that is inhibited by neighboring senescent cells.

To identify specific factors that may be responsible for this effect, conditioned media from elderly and young donors were analyzed using a cytokine microarray to test relative concentrations of 80 cytokines. 44 of the cytokines tested have been identified as part of the senescent associated secretory phenotype. As expected the conditioned media from elderly MSCs contained higher concentrations of most components of the senescence associated secretory phenotype. For 36 out of 44 cytokines (81.8%) were elevated in elderly BM-MSC populations. The difference in 19 out of those 36 cases was statistically significant. This data is summarized in FIG. 6C.

Together, these data suggest that elderly MSCs do contain higher concentrations of senescent cells, that those cells express a senescence associated secretory phenotype similar to those described for other cell types in previous studies and summarized in Freund, et al., 2010 and that these secreted factors are capable of inhibiting the proliferation of "youthful" MSCs.

Example 4

Isolation of Elderly MSC Cell Subpopulation Similar to Young MSCS

Since elderly MSCs appear to suppress proliferation of healthy MSCs, and some elderly MSCs exhibit phenotypic markers indicative of young MSCs, it is believed that sub-population of elderly MSCs that are phenotypically similar to young MSCs may have conserved function, independent of age. Plotting SSEA-4 expression vs. cell size of young and elderly BM-MSCs using flow cytometry, it was observe that young BM-MSCs are relatively homogenous along these dimensions, with the vast majority of cells expressing a small size, SSEA-4 (+) phenotype (small(+)). See FIG. 7A. Elderly BM-MSCs, in contrast, are much more heterogeneous, and can easily be divided into four populations based on size and SSEA-4 expression (FIG. 7A). Elderly BM-MSCs were sorted into 4 populations to determine whether the small(+) sub-population of elderly BM-MSCs has youthful function and whether both these markers do correlate with cell function. See sorting strategy in FIG. 7B. After doublet discrimination, cells were separated into four populations based on expression of SSEA-4 (positive vs. negative), and cell size (small vs. large) as measured by FSC. In order to obtain populations with greater purity, cells with intermediate FSC or FITC intensity were discarded. By sorting, it was determine that only 8.24±3.63% of MSCs from individuals over the age of 65 possess a youthful phenotype when measured along these dimensions.

Example 5

Characterization of Subpopulations of BM-MSCS from Elderly Donors

Figure 9:
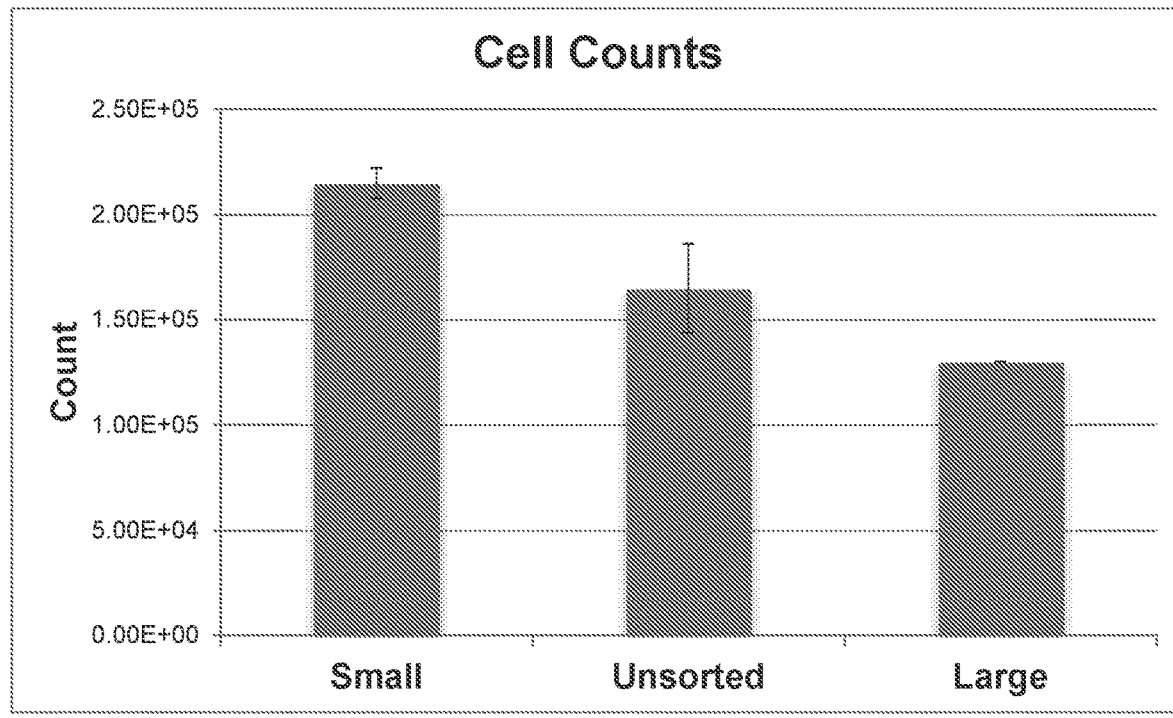
FIG. 9—Self-renewal capacity of small cells from older donors. Cell proliferation was determined for unsorted, small size, and large size BM-MSCs from old donors. Small cells grew 65% more cells than large cells in the same period of time. Small cells also grew faster than cells that were unsorted by size.
Figure 10A:
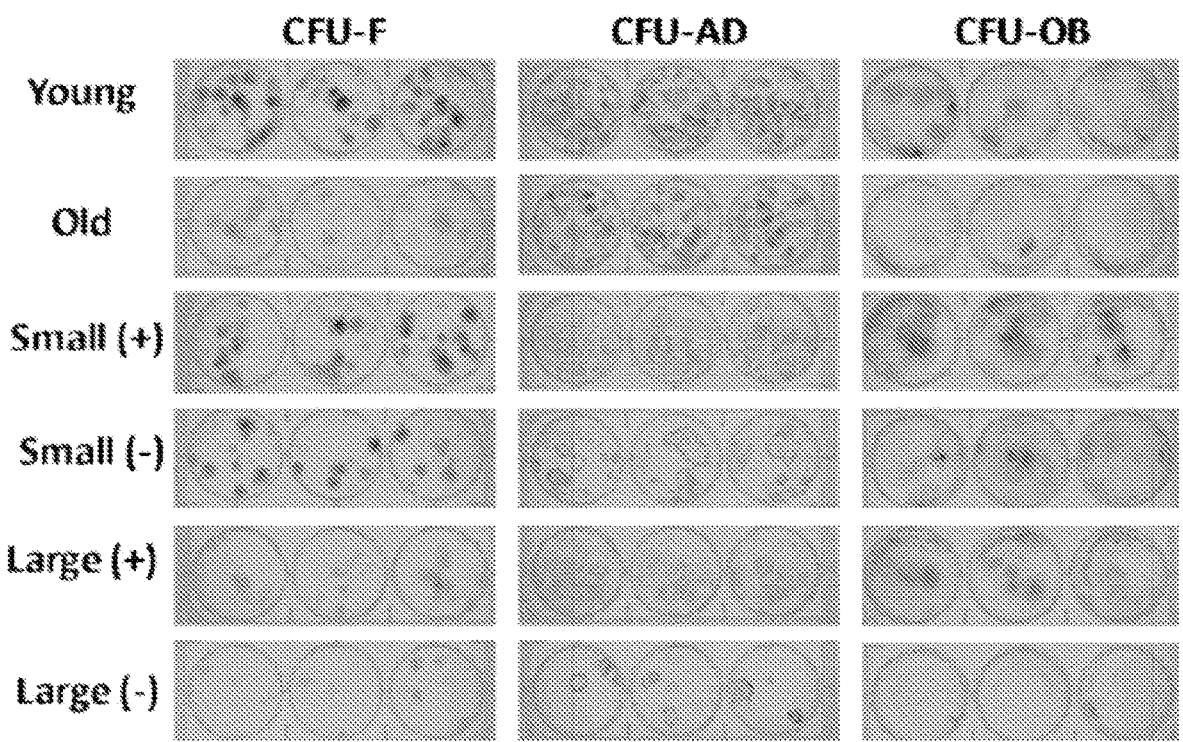
FIG. 10A-10E—Small(+) MSCs exhibit characteristics of more youthful MSCs. (A) Photographs of culture plates of CFU-F, CFU-AD, and CFU-OB assays of young and elderly BM-MSCs cultured on TCP. Immediately following isolation of sub-populations, cells from sub-populations and unsorted populations of young and elderly BM-MSCs were cultured at clonal density for CFU assays. It was observed that small BM-MSCs (especially small+ BM-MSCs) form larger, denser and more numerous colonies with greater differentiation potential than other elderly BM-MSCs. (B) CFU assays were quantified and reported as frequency/100 cells. There are no statistically significant differences between small(+) and young BM-MSCs in any of the CFU assays stained for markers of differentiation into fibroblast (CFU-F), osteoblast (CFU-OB), and adipocytes (CFU-AD). (C) ATP levels were similar to more youthful levels in small BM-MSCs from elderly donors relative to the large-size sub-populations. (D) Small MSCs and small(+) MSCs, in particular, expressed β-Gal levels similar to that of young cells, suggesting that very few senescent cells exist in the small-size subpopulations. (E) Conditioned media was collected in order to analyze the cytokine profile. The heat map summarizes expression of SASP cytokines in young, elderly, and small(+) MSCs. It was shown that small (+) MSCs from older donors do not express SASP. *P<0.05, vs. young MSCs on the same substrate.
Figure 10B:
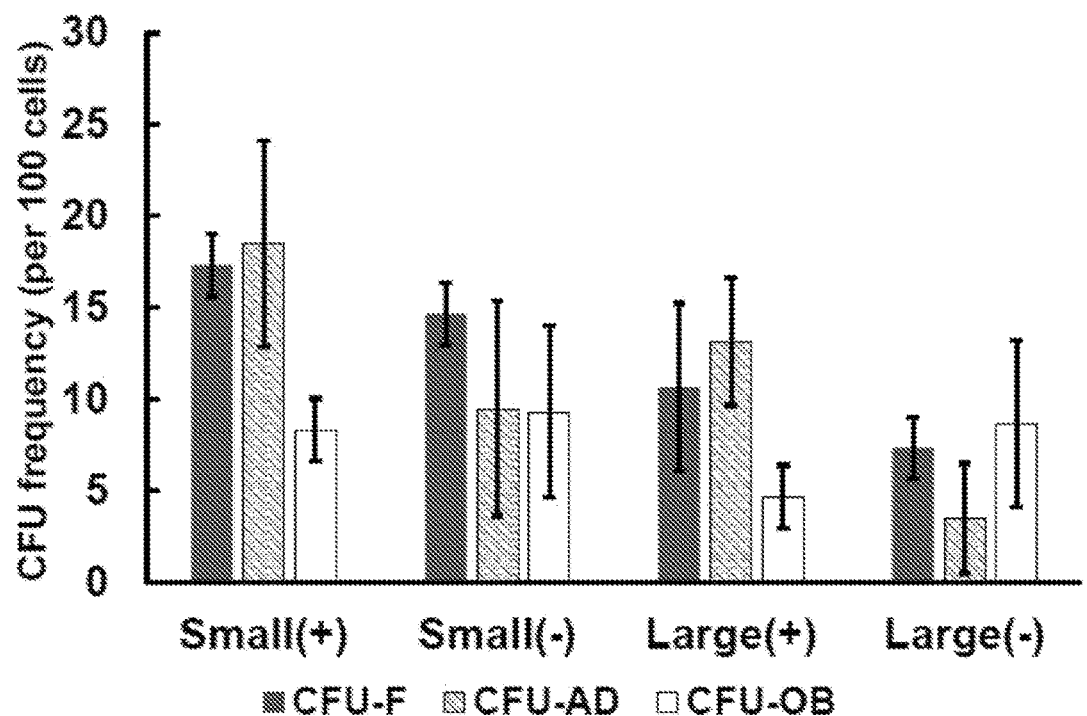
Figure 11:
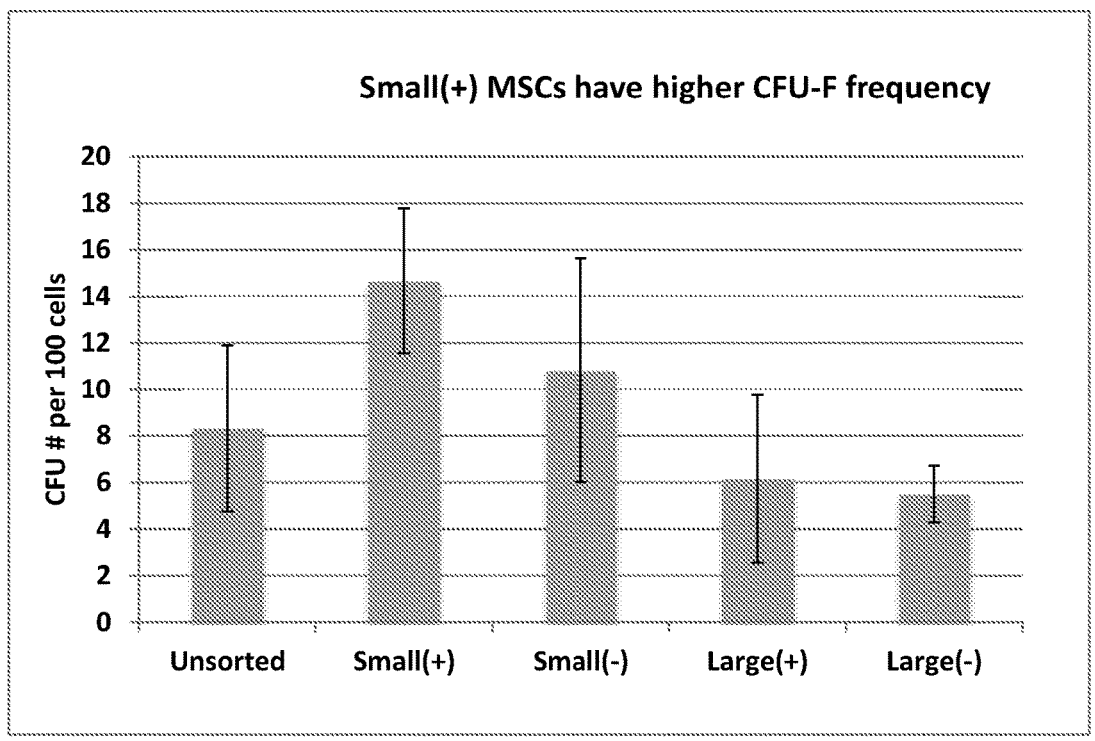
FIG. 11—Stem cell concentration was determined for Unsorted, Large −, Large +, Small −, and Small + populations of BM-MSC cells from elderly donors by measuring the number of colony forming units (CFU-F). Small cells that express SSEA-4 have a much greater concentration of stem cells than the other populations of cells.

The resulting populations were compared to young BM-MSCs as well as the unfractionated BM-MSCs from elderly donors using in vitro assays. By inspection, young cells appear to have the most colonies in each condition, while the small (+) population is substantially increased relative to BM-MSCs isolated to elderly donors (FIG. 10A). This is substantiated by manually counting colonies (FIG. 10B and FIG. 11). In fact, there were no statistically significant differences between small(+) BM-MSCs and young BM-MSCs in colony formation. This suggests that there is likely very little difference, if any, in the number and potency of MSCs in the small(+) elderly subpopulation, relative to young cells. Cell proliferation was also determined for unsorted, small size, and large size BM-MSCs from older donors by cell count. Small cells grew 65% more cells than large cells in the same period of time. Small cells also grew faster than cells that were unsorted by size (FIG. 9).

Figure 12:
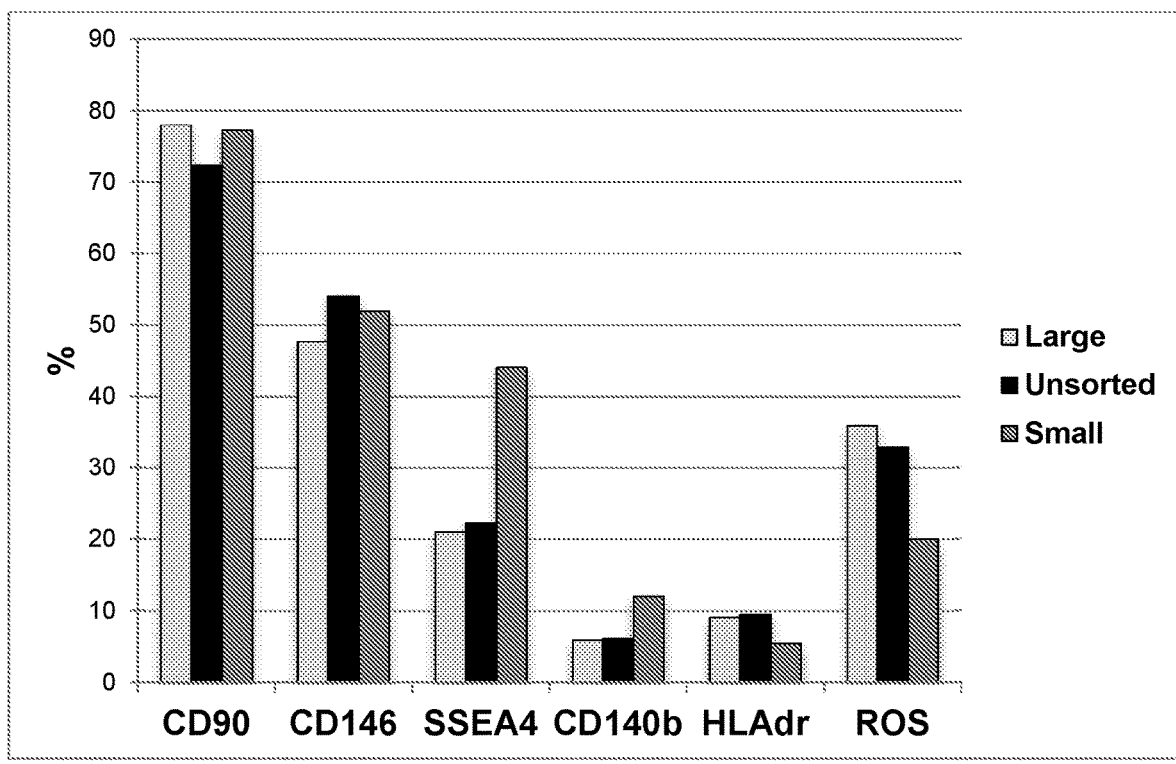
FIG. 12—Expression and ROS phenotype of small size, large size, and unsorted cells from older donors. The percentage of cells expressing several proteins associated with youth and aging and percentage of cells with detectable ROS levels were determined in cells from old donors with small size (Small), large size (Large), and unsorted size (Unsorted). Cells with small size expressed higher SSEA-4 and platelet-derived growth factor PDGF than large cells and lower HLAdr and intracellular ROS.

The percentage of cells expressing several proteins associated with youth and aging and percentage of cells with detectable ROS levels were determined in cells from old donors with small size, large size, and unsorted size. Cells with small size expressed higher SSEA-4 and platelet-derived growth factor PDGF than large cells and lower HLAdr and intracellular ROS. See FIG. 12. This demonstrates that small size cells have a phenotype more similar to young cells, such as higher SSEA-4, lower HLAdr, and lower intracellular reactive oxygen species (ROS).

Figure 10C:
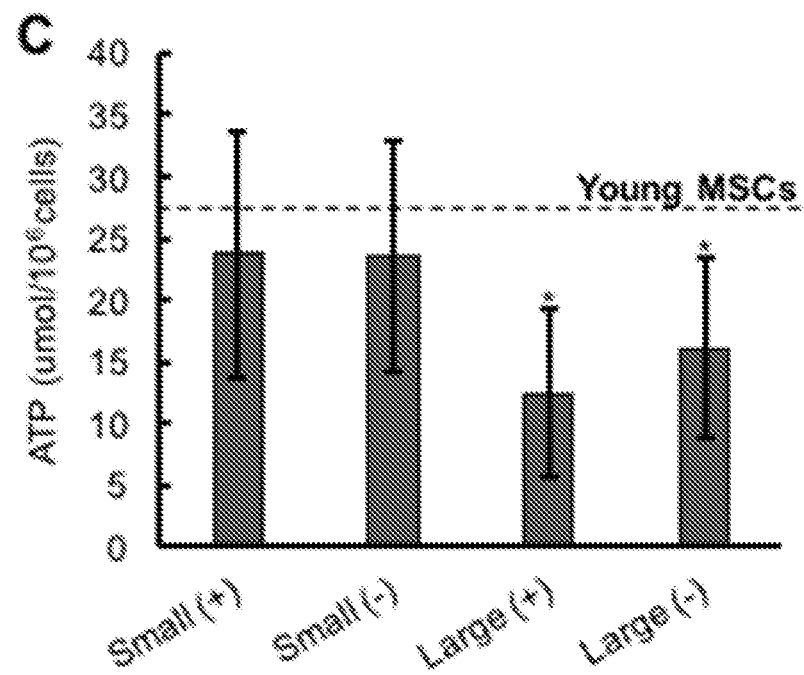
Figure 10D:
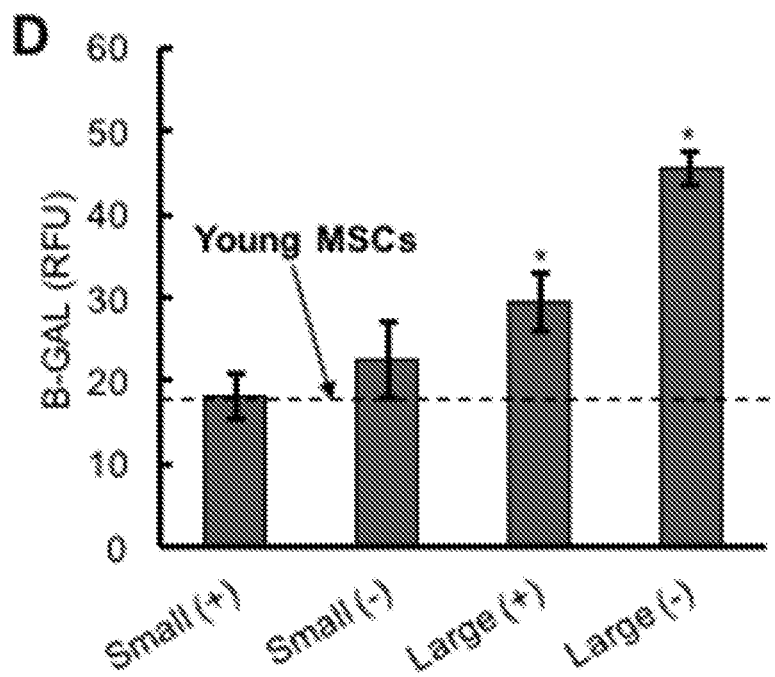
Figure 13:
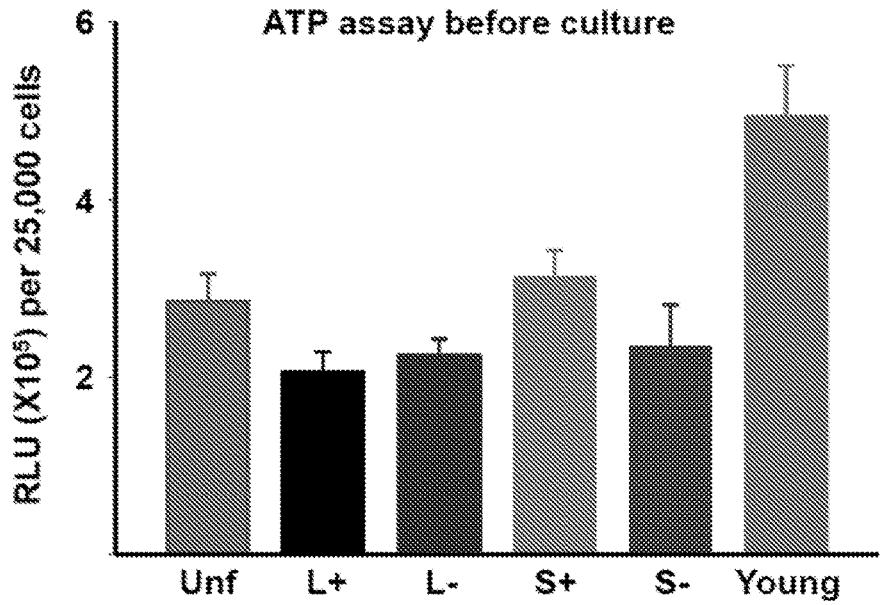
FIG. 13—Cells with higher ATP concentrations within cell subpopulations before culture. Bone marrow stromal cells were harvested from elderly people and young people (Young). The bone marrow stromal cells from elderly people were either not separated (Unf) or separated according to size (L=large, S=small) and presence of SSEA-4 (+=present, −=not present). It was shown that small size and presence of SSEA-4 correlates with an increased number of cells with increased ATP content in comparison to the other groups of cells from bone marrow stromal cells from elderly people.
Figure 14:
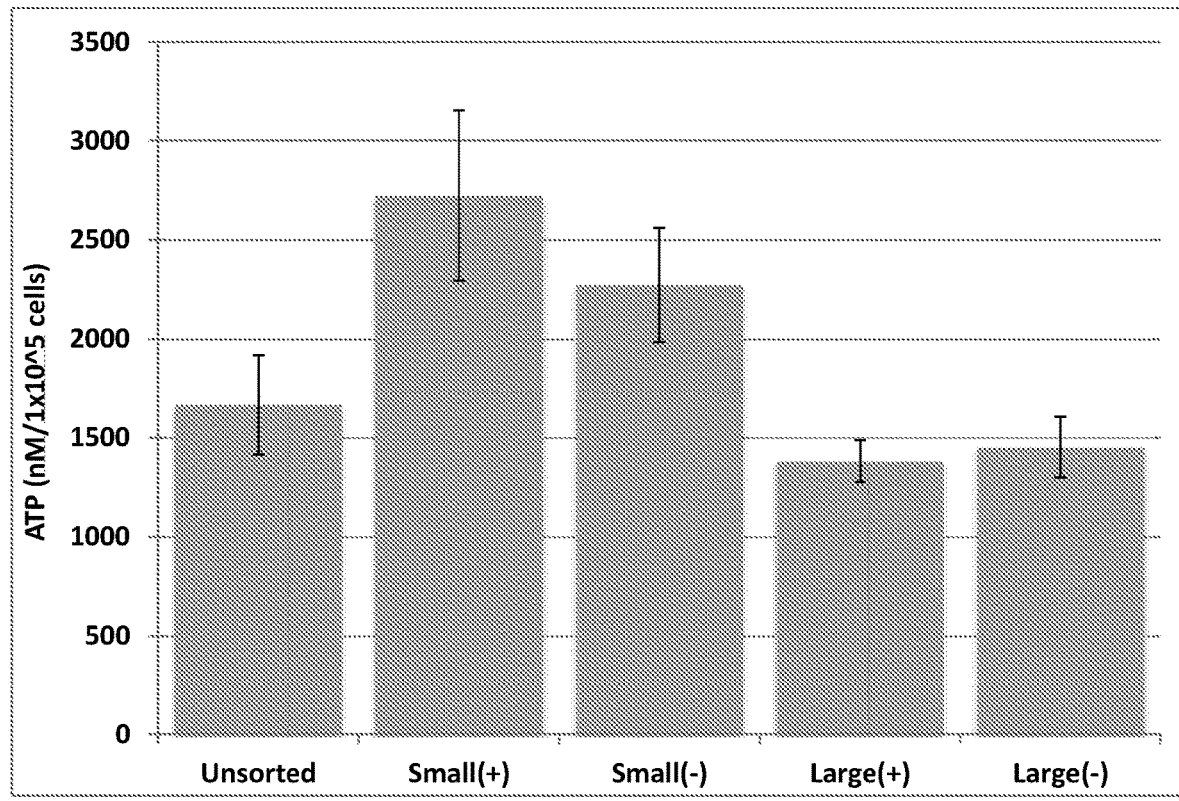
FIG. 14—ATP concentration of cell subpopulations before culture. Bone marrow stromal cells were harvested from elderly people. The bone marrow stromal cells from elderly people were either not separated (Unf) or separated according to size (L=large, S=small) and presence of SSEA-4 (+=present, −=not present). It was shown that small size and presence of SSEA-4 correlates with increased ATP content in comparison to the other groups of cells from bone marrow stromal cells from elderly people.
Figure 15:
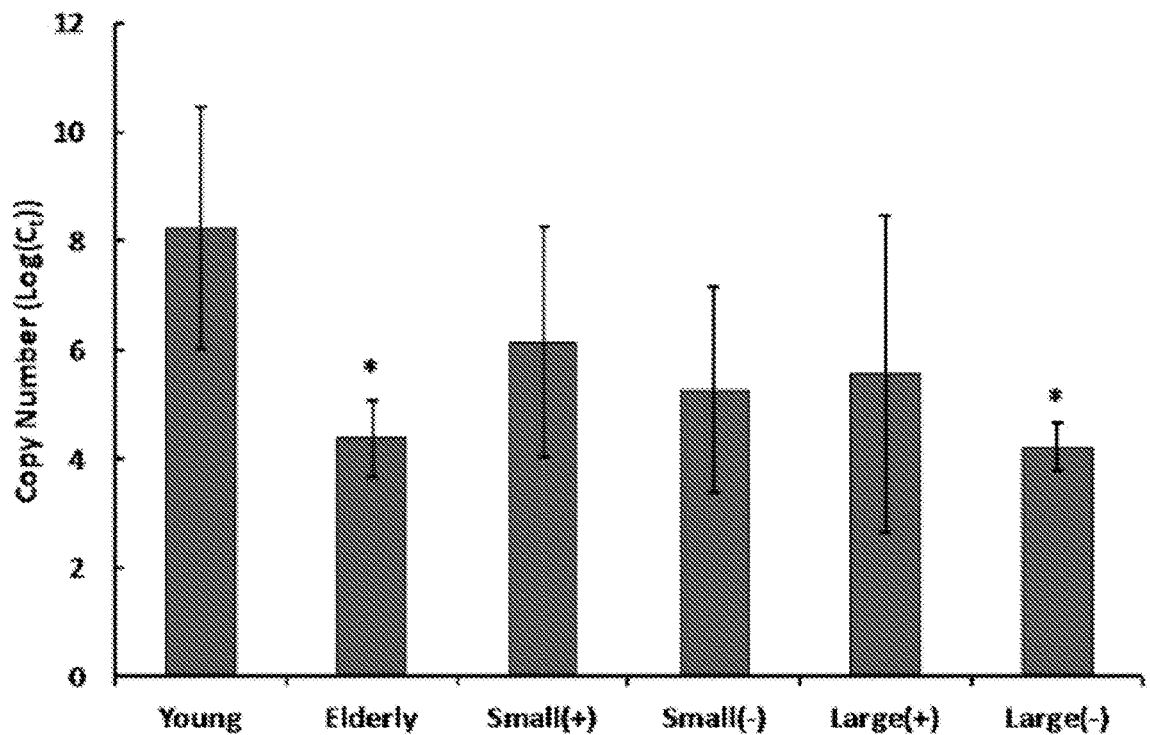
FIG. 15—Graph of Telomerase levels measured for Young and Elderly BM-MSCs; and Large −, Large +, Small −, and Small + populations of BM-MSCs from elderly donors. Telomerase levels are slightly higher for small cells that express SSEA-4.
Figure 30A:
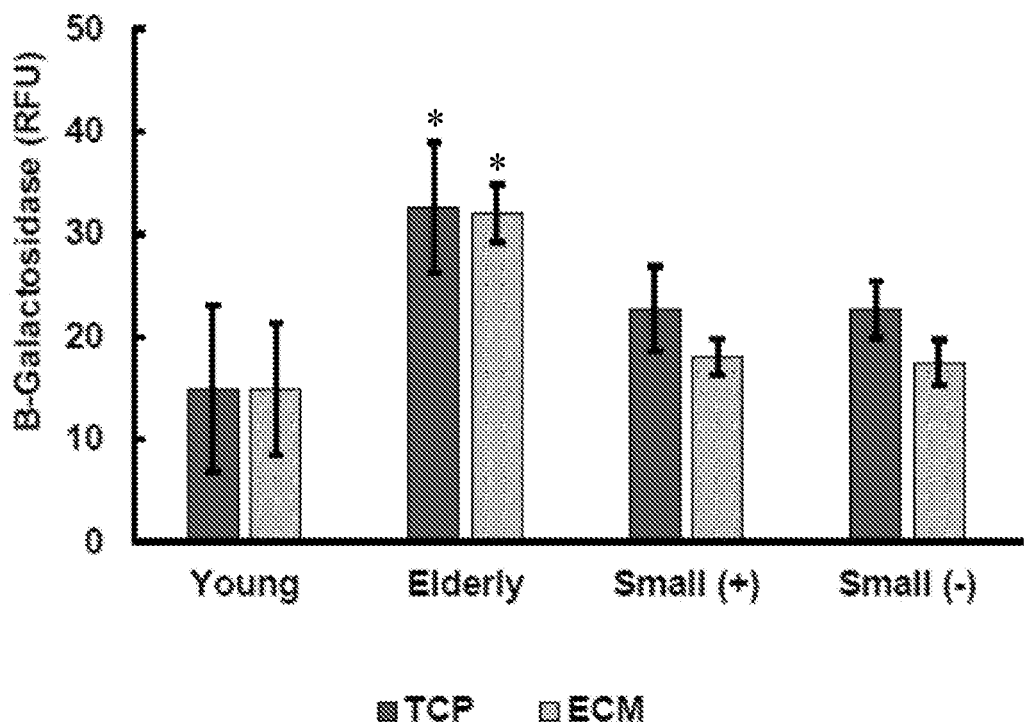
FIG. 30A-30C—Small (+) MSCs expanded on ECM maintain a youthful phenotype. (A) Graph of β-Galactosidase expression of unfractionated (Young; Elderly) and fractionated elderly BM-MSCs. β-galactosidase expression was measured in Young, Elderly, Small +, and Small − populations following culture on TCP or ECM derived from BM-MSCs from young donors (young ECM). Small size sub-populations maintain low levels of senescence during culture. Small cells isolated from elderly donors maintain low expression during culture. (B) Graph of ATP levels of unfractionated (Young, Elderly) and fractionated elderly BM-MSCs following culture on TCP and ECM derived from BM-MSCs from young donors (young ECM). ATP expression was determined following culture of young and elderly BM-MSCs and elderly subpopulations of BM-MSCs (S+, S−) on TCP or young ECM. S+ cells cultured on tissue culture plastic (TCP) have significantly higher ATP concentration. Young ECM increased ATP content in for most groups. (C) SASP cytokine profile of cells on ECM is shown in the heat map. Multiway ANOVA followed by Tukey's Honest Significant Difference procedure reveal a statistically significant increase in SASP cytokine expression in elderly BM-MSCs relative to young or small (+) BM-MSCs. *$P<0.05$, vs. young BM-MSCs on the same substrate. ♣ $P<0.05$, vs. the same population of cells cultured on TCP.
Figure 30B:
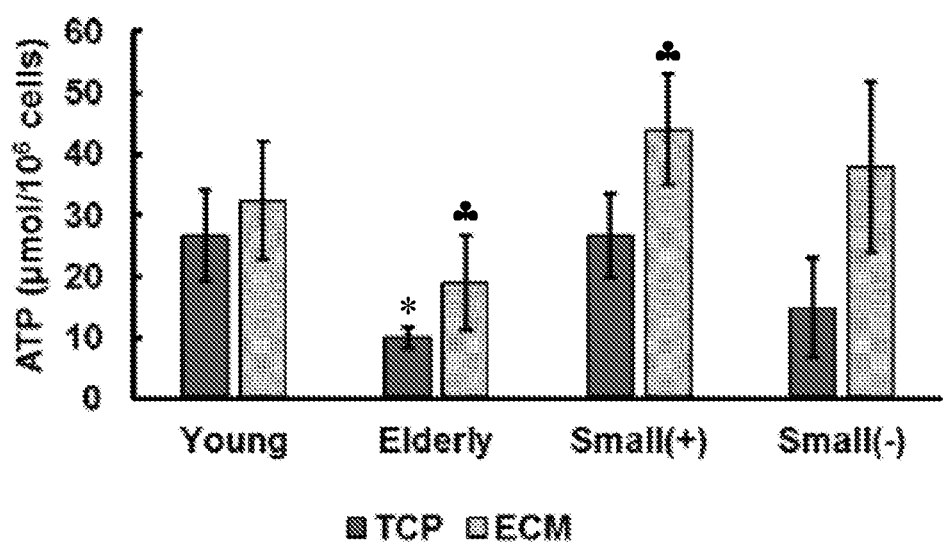

ATP concentration, cell numbers with high levels of ATP, ATP content of cells, telomerase levels, and β-Galactosidase expression for the four sub-populations of BM-MSC cells from old donors were determined. Small BM-MSCs, independent of SSEA-4 expression, exhibit ATP concentration on par with that of young BM-MSCs. Whereas, large BM-MSCs, regardless of SSEA-4 expression, have ATP levels roughly half that of young BM-MSCs (FIG. 10C, FIG. 14, and FIG. 30B). It was found that small size and presence of SSEA-4 correlates with increased number of cells with higher ATP content, higher ATP content per cell, slightly increased telomerase levels in comparison to the other groups of cells from bone marrow stromal cells from elderly people (FIGS. 13 through 15). Fittingly, large BM-MSCs had significantly more senescent cells than small or young BM-MSCs, with large (−) cells exhibiting the highest β-Galactosidase (β-Gal) expression, β-Gal is a marker of senescence and expression is reported as relative fluorescence using a fluorometric assay (FIG. 10D). The dashed line represents the mean β-Galactosidase expression of young BM-MSCs. Small BM-MSCs were statistically equivalent to young BM-MSCs. Not to be bound by theory, the evidence that small(+) cells have a low frequency of senescent cells fits the theory that they may represent a sub-population of elderly MSCs that in normal conditions are suppressed by their senescent neighbors.

Figure 10E:
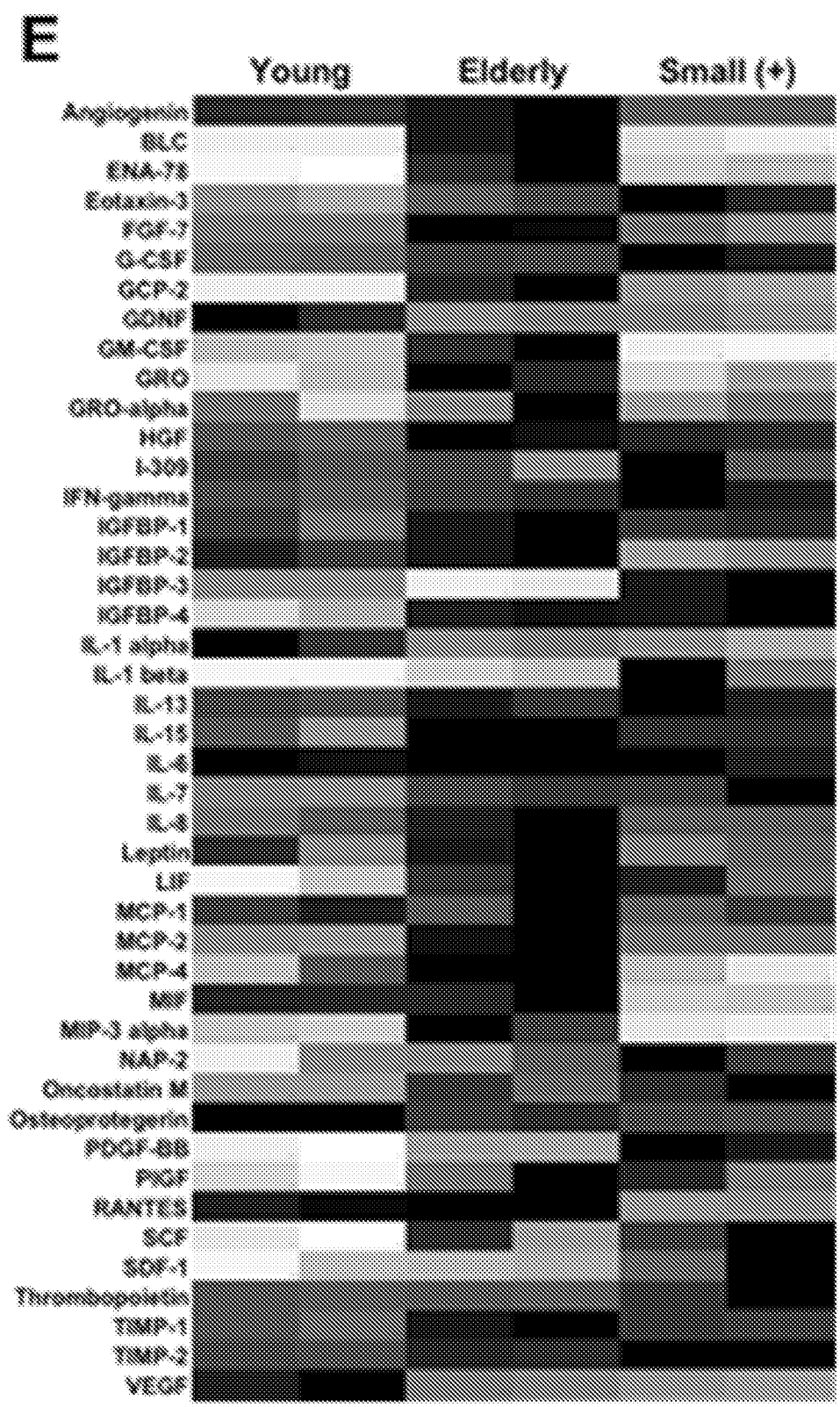

Expression of cytokines that characterize the senescence associated secretory phenotype were tested to determine if small(+) cells are more similar to young MSCs than elderly MSCs. The heat map in FIG. 10E shows expression of the 44 cytokines tested known to be part of the SASP. Multiway ANOVA, followed by Tukey's honest significant difference procedure reveals that elderly BM-MSCs have higher expression of SASP cytokines than either young or small (+) BM-MSCs ($p<0.0001$ or $p=0.039$ respectively). There was not a significant difference in expression of SASP factors between young and small (+) BM-MSCs ($p=0.068$).

Cell proliferation was also determined for BM-MSCs from young donors grown in growth media conditioned with secretions from subpopulations of old donor's BM-MSCs with either small cell size (Small) or large cell size (Large), secretions from old donor's BM-MSCs unsorted by size (Unsorted), and secretions from young donor BM-MSCs (young CM). See FIG. 16. The proliferation rate of BM-MSCs from young donors was inhibited as determined by cell count when cultured in Large and Unsorted conditioned media while culturing in Small and Young conditioned media showed little to no difference. This suggests that the environmental factors that inhibit MSC growth in old donors may be at least partially dependent on harmful factors introduced by the large MSCs.

Example 6

Culturing Stem Cells on TCP and BM-ECM

Figure 17:
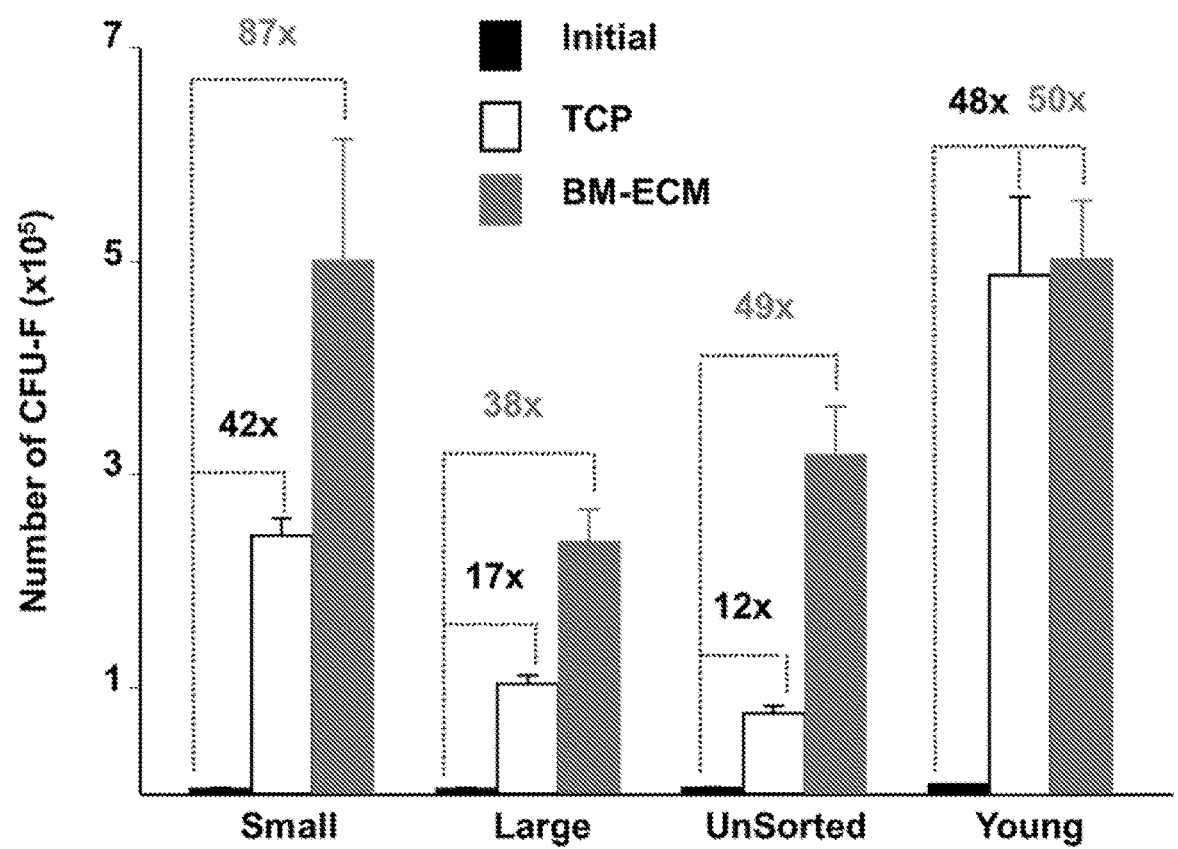
FIG. 17—Rescuing stem cells in BM-MSCs from young donors and small size, large size, and unsorted size BM-MSCs from old donors. The number of stem cells in BM-MSCs from young donors and small size, large size, and unsorted size BM-MSCs from old donors was determined by counting the number of colony forming units before and after culturing on tissue culture plastic (TCP) and bone marrow extracellular matrix (BM-ECM). Culturing small cells from an older donor showed an increase in stem cells rescued in comparison to large and unsorted cells from an old donor. Further, culturing in BM-ECM showed an increase in stem cells in comparison to culturing on TCP.

Results demonstrating that it is possible to isolate a fraction of MSCs from elderly MSC populations with compromised function are promising. However, some cell-based therapies require a high quantity of high quality cells. Even if one were able to obtain a fraction of cells that are very high quality, they may be a small subset of the original population, making it difficult to obtain a sufficient number of cells for clinical relevance. To overcome this, cells may be expanded. This approach, however, comes with its own pitfalls. Traditionally, quality and quantity are competing needs, because as MSCs expand on TCP, they may undergo spontaneous differentiation, resulting in a population with a very different phenotype than those cells initially isolated. To address this issue the sub-populations were expanded on young ECM, which has been shown to allow cells to proliferate while maintaining stemness (Sun, et al., 2011). The number of stem cells in BM-MSCs from young donors and small size, large size, and unsorted size BM-MSCs from old donors was determined by counting the number of colony forming units (CFU) before and after culturing on tissue culture plastic (TCP) and bone marrow extracellular matrix (BM-ECM). Culturing small cells from an older donor showed an increase in stem cells rescued in comparison to large and unsorted cells from an old donor. Further, culturing in BM-ECM showed an increase in stem cells in comparison to culturing on TCP (FIG. 17).

Figure 18:
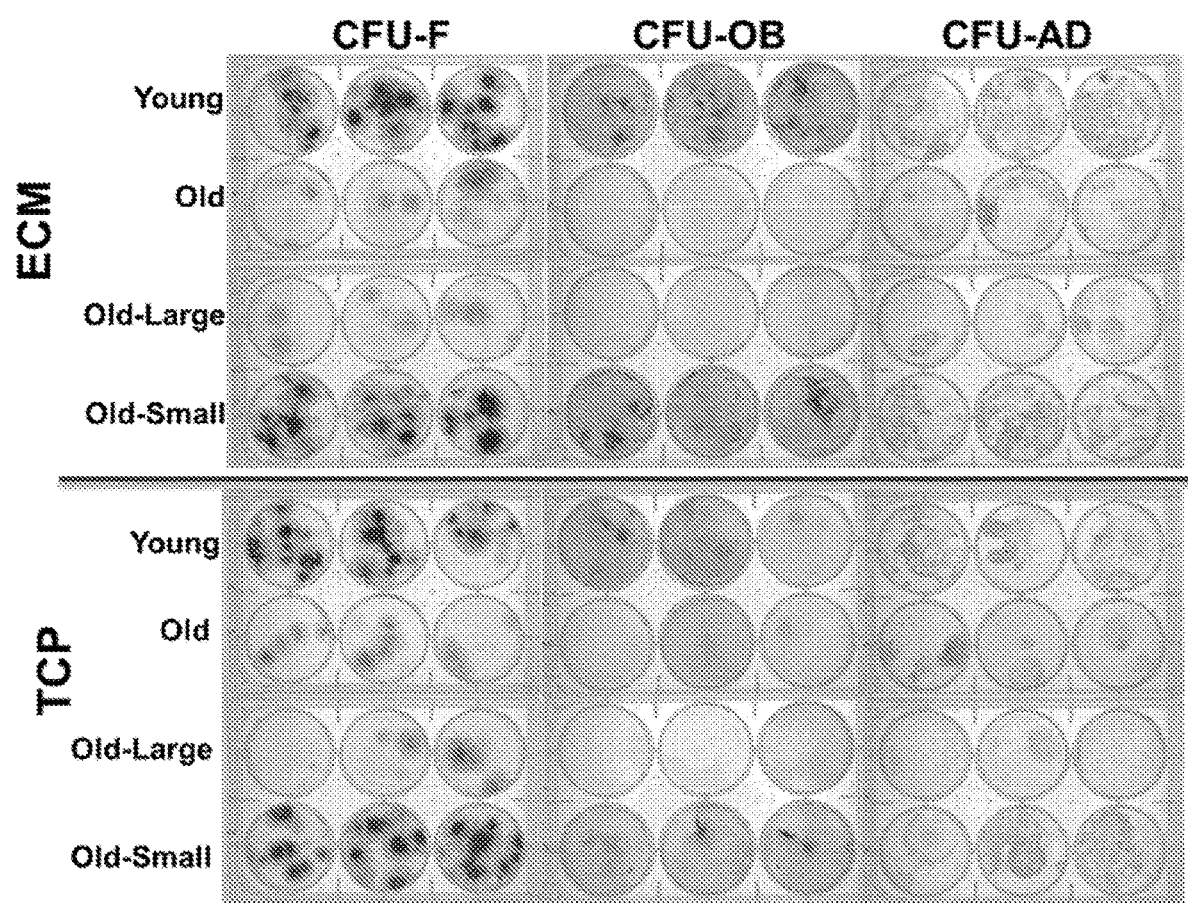
FIG. 18—CFUs from unsorted BM-MSCs from young donors and old donors, large size cells from old donors, and small size cells from old donors were grown on ECM and TCP and stained for markers of differentiation into fibroblast (CFU-F), osteoblast (CFU-OB), and adipocytes (CFU-AD). The CFUs of small cells from old donors showed similar differentiation ability to cells from young donors.

CFUs of BM-MSCs from young donors and small size, large size, and unsorted size BM-MSCs from elderly donors were also tested to determine their ability to differentiate as demonstrated by staining for markers of differentiation into fibroblast (CFU-F), osteoblast (CFU-OB), and adipocytes (CFU-AD). The CFUs of small cells from elderly donors showed similar differentiation ability to cells from young donors (FIG. 18).

Figures 19A, 19B:
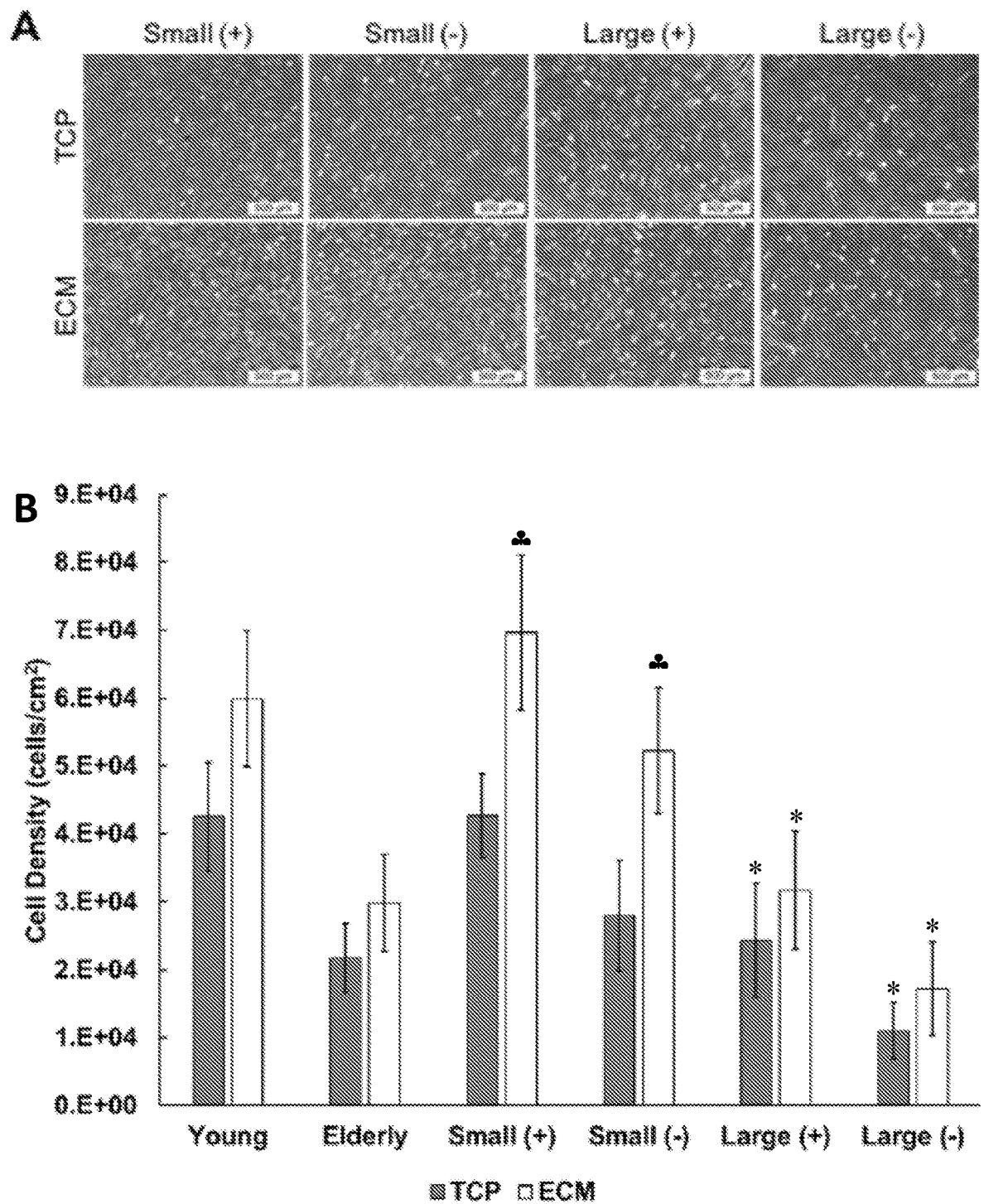
FIG. 19A-19F—ECM expansion enhances replication of small MSCs. (A) Small MSCs proliferate rapidly on ECM and become highly confluent after 6 days of culture. (B) Graph of cell density of unfractionated (young; elderly) and fractionated elderly BM-MSCs following 7 Days in culture on TCP vs. ECM derived from BM-MSCs from young donors (young ECM). Total cell proliferation for each population is shown as cell density after 7 days in culture and equal seeding density (3,000 cells/cm$^2$). Cell proliferation was determined quantitatively by counting the number of cells in the culture dishes after culturing the BM-MSC subpopulations for 7 days on TCP or young ECM. The populations tested included non-separated BM-MSC (Young and Elderly), large cells positive for the presence of SSEA-4 (Large +) or negative for SSEA-4 (Large −) and small cells positive for the presence of SSEA-4 (Small +) or negative for SSEA-4 (Small −). Small+ cells showed increased cell proliferation on both TCP and young ECM and showed a 4 fold increase of number of cells when compared to non-separated cells grown on TCP. The results suggest that young ECM increases proliferation rate of all of the subpopulations. Further small cell size also seems to increase proliferation rates. (C) Following expansion on TCP or ECM cells were seeded at clonal density for CFU assays. Small (+) MSCs produce larger, denser, and more numerous colonies in all 3 assays. (D-F) CFUs were quantified by multiplying the CFU frequency by the total number of cells. Fold change is reported on the graphs. *P<0.05, vs. young BM-MSCs on the same substrate. ♣P<0.05, vs. the same population of cells cultured on TCP.
Figure 22:
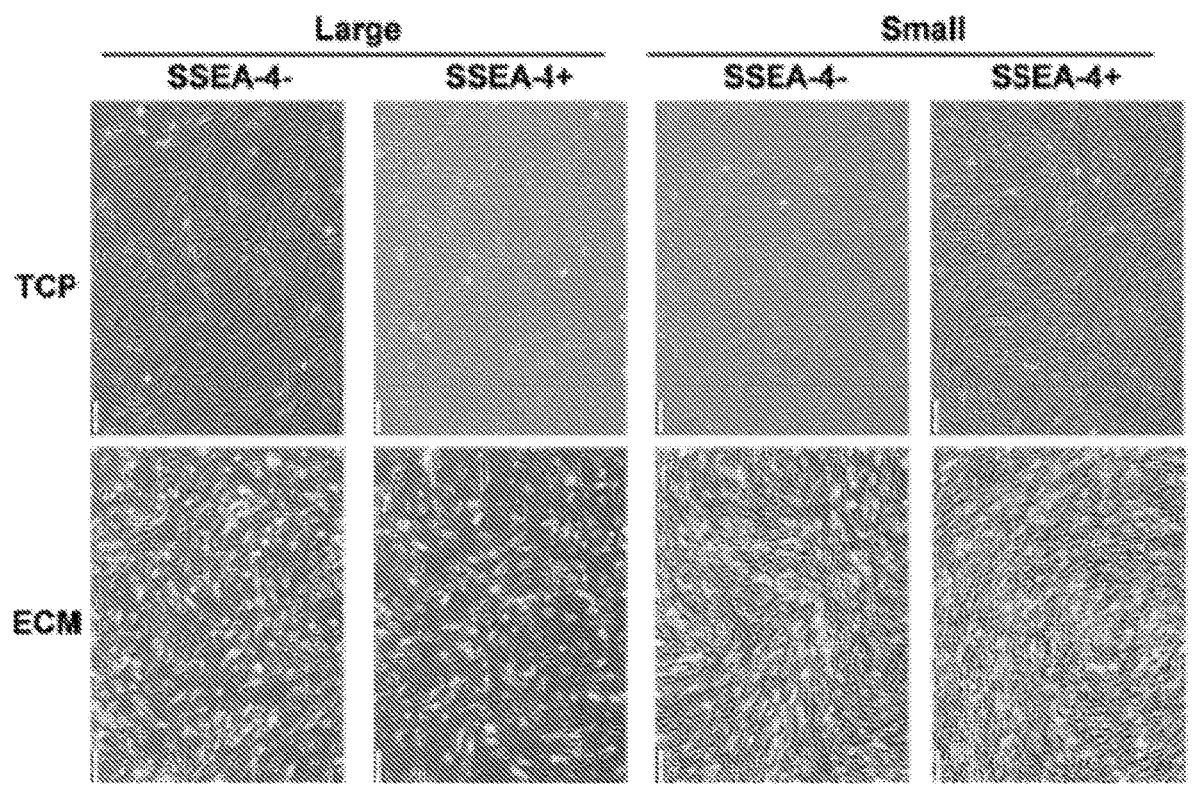
Figure 23:
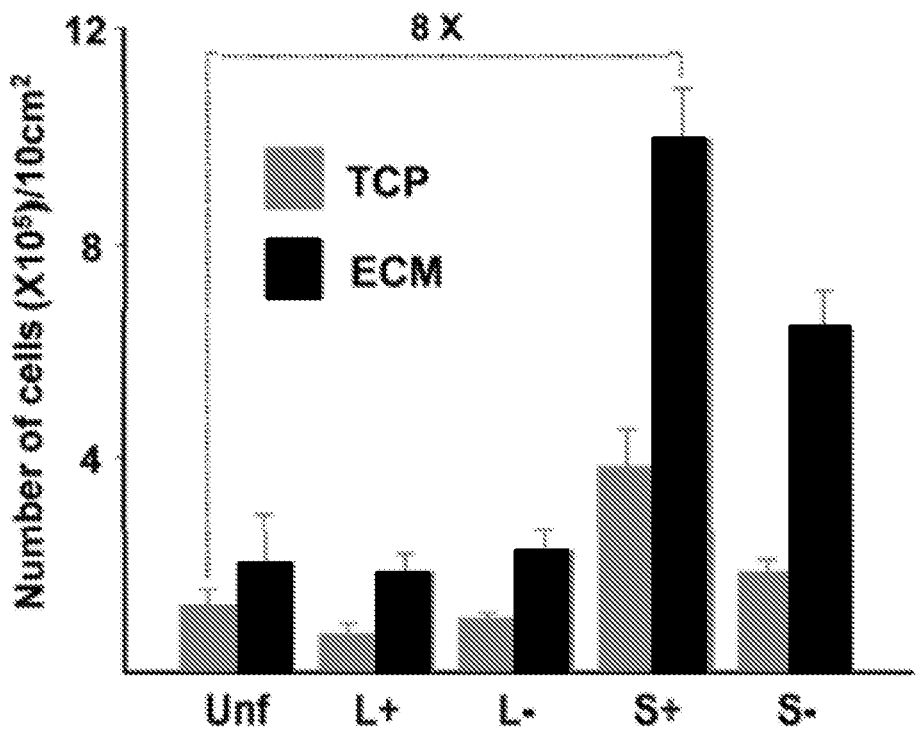
FIG. 23—Cell proliferation was determined quantitatively by counting the number of cells in the culture dishes after culturing the BM-MSC subpopulations for 7 days on TCP or young ECM. The populations tested included non-separated BM-MSC (Unf), large cells positive for the presence of SSEA-4 (L+) or negative for SSEA-4 (L−) and small cells positive for the presence of SSEA-4 (S+) or negative for SSEA-4 (S−). S+ cells showed increased cell proliferation on both TCP and young ECM and showed an 8-fold increase of number of cells when compared to non-separated cells grown on TCP. The results suggest that young ECM increases proliferation rate of all of the subpopulations. Further small cell size also seems to increase proliferation rates (S−).
Figure 24:
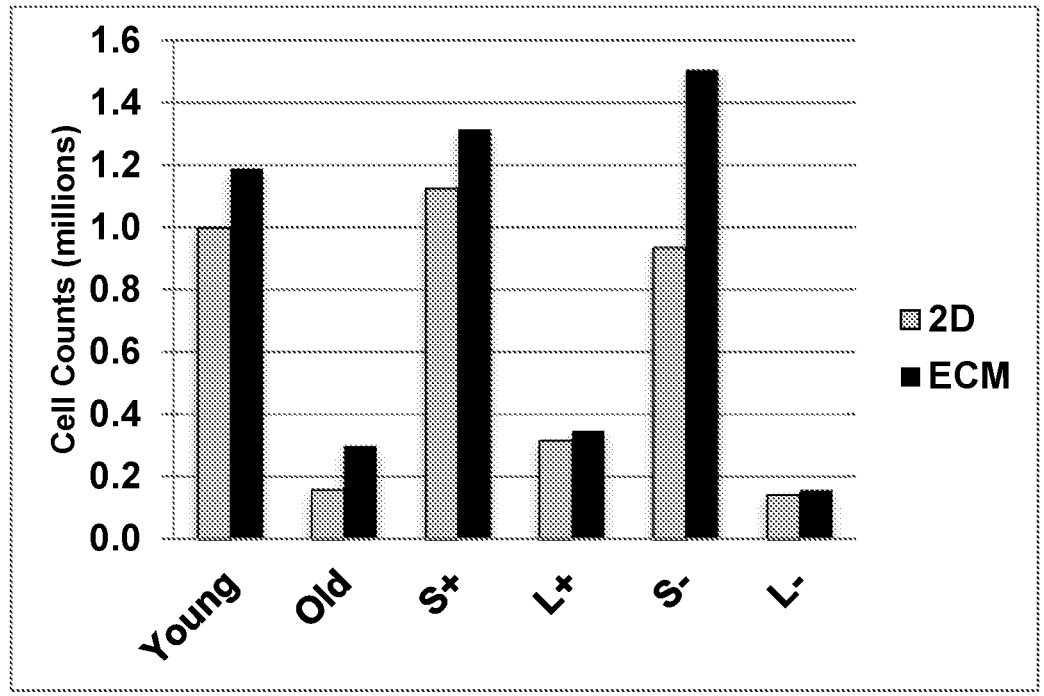
FIG. 24—Cell proliferation was determined quantitatively by counting the number of cells in the culture dishes after culturing young and old BM-MSCs (Young and Old, respectively) and old subpopulations of BM-MSCs (S+, L+, S−, and L−) on TCP (2D) (left column) or ECM (right column). S+ cells showed increased cell proliferation on both TCP and young ECM and S− cells also showed improved cell proliferation.
Figure 25:
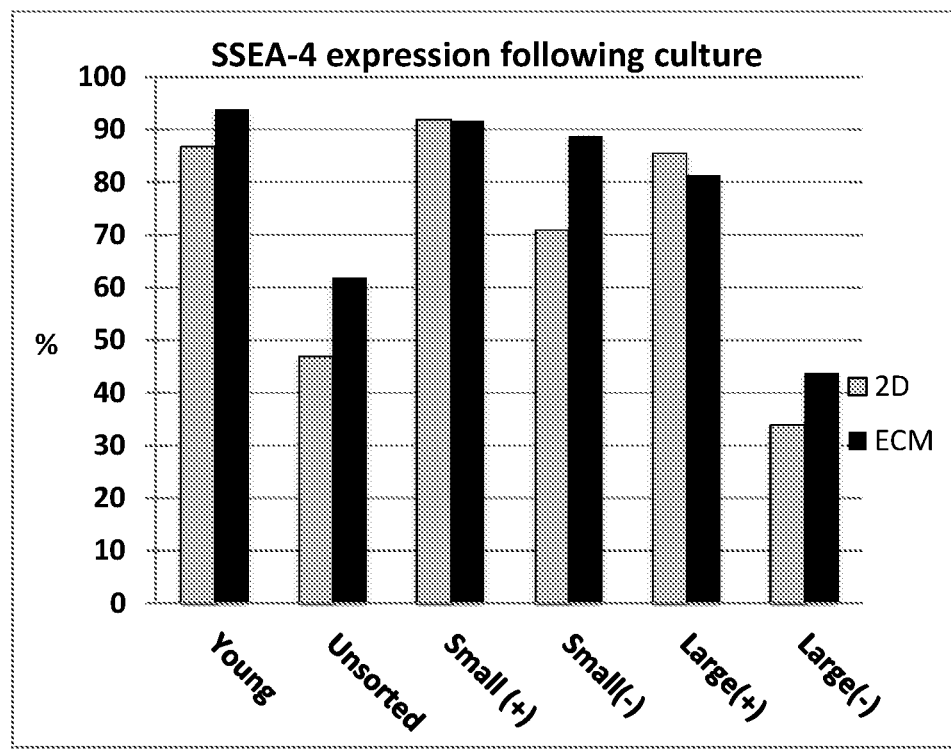
FIG. 25—Percentage of cells expressing SSEA-4 was determined following culture of young and old BM-MSCs (Young and Unsorted, respectively) and old subpopulations of BM-MSCs (Small(+), Small(−), Large(+), and Large(−)) on TCP (left column) or ECM (right column). Small(+) cells showed high expression of SSEA-4, and in most groups culture on ECM increased SSEA-4 expression.

Cell proliferation, colony forming capacity, and differentiation capacity were determined for BM-MSCs from elderly donors separated into the four sub-populations cultured on TCP and BM-ECM. For cells cultured for 7 days, small (+) BM-MSCs cultured on TCP and BM-ECM, exhibit remarkable recovery relative to unsorted elderly MSCs (FIG. 19A and FIG. 22). They appear similar in morphology to cells from a young donor, and are highly confluent after 7 days culture. Interestingly, small (−) BM-MSCs also appear substantially healthier than elderly BM-MSC populations and are capable of relatively rapid proliferation. Cells cultured on young ECM showed improvements in cell proliferation in comparison to cells cultured on TCP. Small cells also showed an increase in proliferation rates in comparison to large size BM-MSCs and non-separated BM-MSCs. Small + cells showed increased cell proliferation on both TCP and young ECM. For small cells, there was a significant improvement when cells were expanded on BM-ECM (FIG. 19B, FIG. 23, and FIG. 24). Small(+) cells cultured on BM-ECM actually proliferated more rapidly than young cells expanded on TCP or BM-ECM (FIG. 19B and FIG. 24). The results suggest that young ECM increases proliferation rate of all of the subpopulations and cells from young donors. Further small cell size also seems to increase proliferation rates.

Figure 19C:
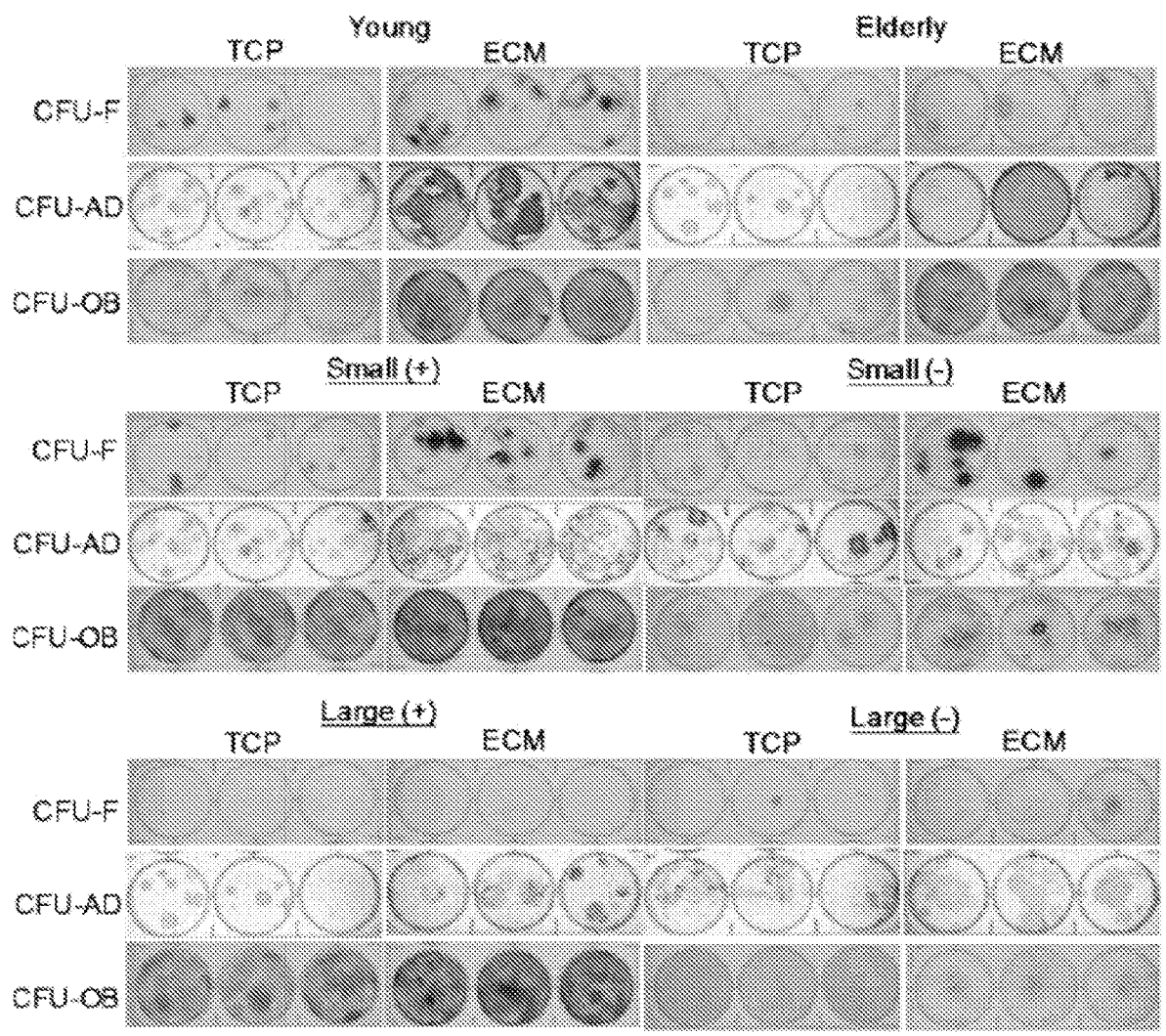
Figures 19D, 19E, 19F:
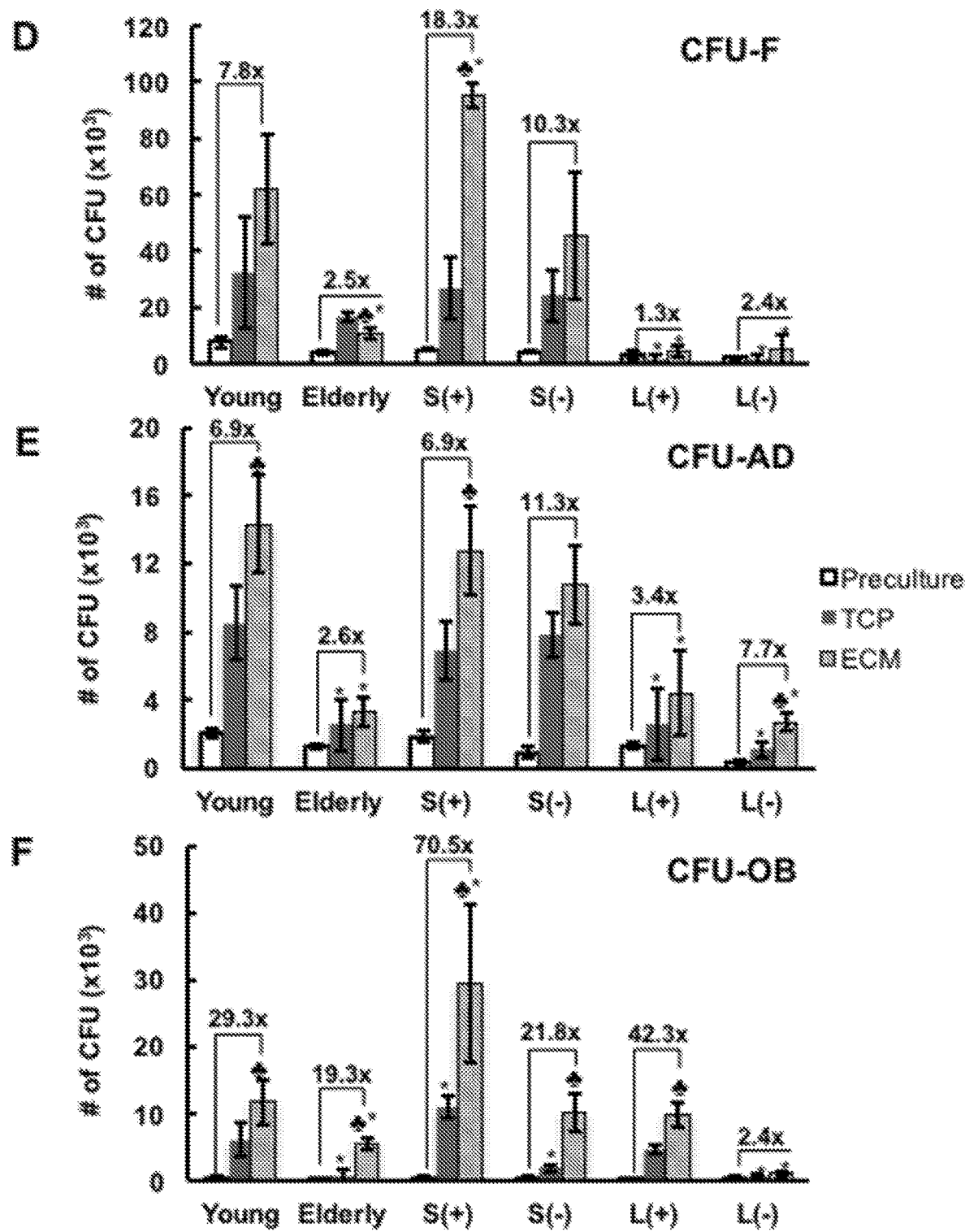

After 7 days culture, cells were detached and reseeded at clonal density for CFU-F, CFU-AD, and CFU-OB assays (FIG. 19C). The results of the CFU assays were consistent with the observed proliferation. Small cells expanded on ECM formed colonies that were larger, denser, and more numerous. The same is not true for either large cell populations, with the notable exception that large (+) cells display increased osteogenesis following culture on young ECM. It is also worth mentioning that the large (+) population does appear to have substantial osteogenic potential, generally. Not to be bound by theory, it is possible that this population is already committed to an osteogenic fate. In FIGS. 19D-F, results of the CFUs are quantified. Here, small positive cells are shown to consistently have a high fold change in the total number of CFU for all 3 assays following culture on ECM.

Figure 32:
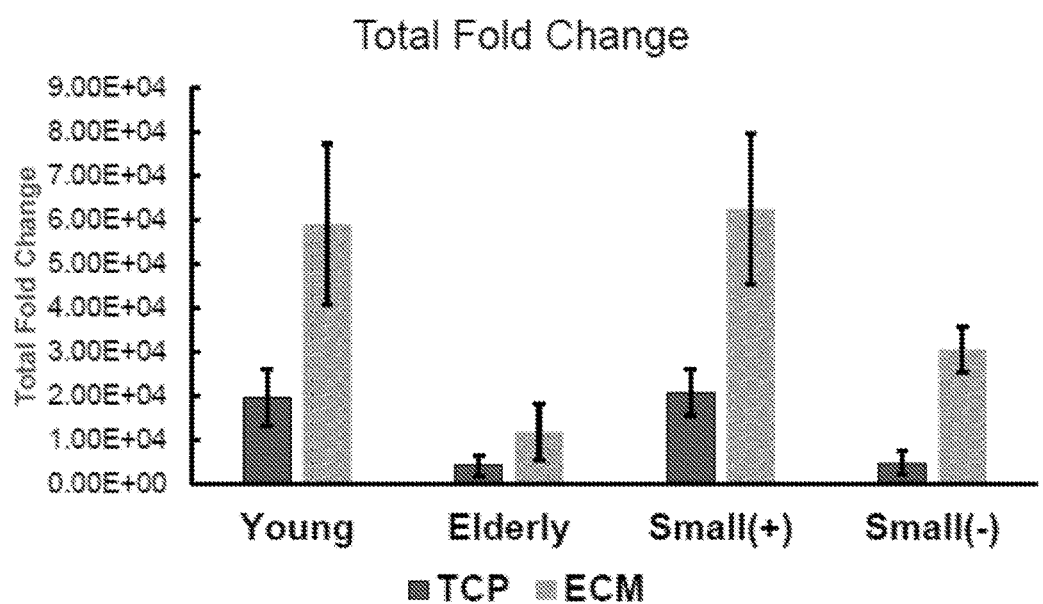
FIG. 32—Graph of total fold change of unfractionated (Young; Elderly) and fractionated Elderly BM-MSCs after 4 passages. The cells were passaged every 7 days in culture on TCP vs. ECM derived from BM-MSCs from young donors (young ECM) using a seeding density of 1500 cells/cm$^2$. The number of SSEA-4 positive cells after 4 passages of BM-MSCs from young and elderly BM-MSCs and elderly subpopulations of BM-MSCs (Small +, Small −) on TCP or young ECM increased dramatically. Serial passage on young ECM resulted in a fold change of roughly 6,000 when small+ cells were expanded on young ECM.

Also, the total fold change of unfractionated (Young; Elderly) and fractionated Elderly BM-MSCs was determined after 4 passages. The cells were passaged every 7 days in culture on TCP vs. ECM derived from BM-MSCs from young donors (young ECM). The seeding density 1500 cells/cm$^2$. The number of SSEA-4 positive cells after passages of BM-MSCs from young and elderly BM-MSCs and elderly subpopulations of BM-MSCs (Small +, Small –) on TCP or young ECM increased dramatically. Serial passage on young ECM resulted in a fold change of roughly 6,000 when small+ BM-MSCs were expanded on young ECM (FIG. 32).

Thus, the data suggests that a small subpopulation of less defective BM-MSCs (~10%) can be isolated from aging bone marrow cells of elderly people and their proliferative capacity can be remarkably improved by provision of ECM made by marrow stromal cells from young donors.

Example 7

Characterization of BM-MSCS Cultured on BM-ECM and TCP

Unsorted and fractionated BM-MSCs cultured on young BM-ECM and TCP were further characterized.

Figure 29:
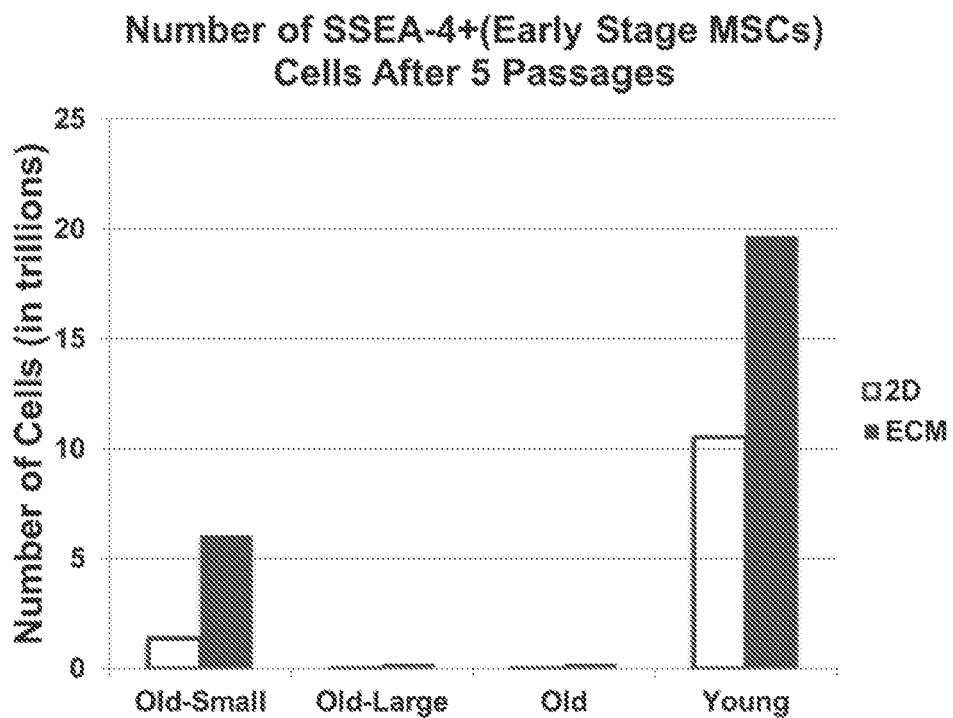
FIG. 29—The number of SSEA-4 positive cells after 5 passages of BM-MSCs from young donors and small size, large size, and unsorted size BM-MSCs from old donors was determined after culturing on ECM and Tissue Culture Plastic (2D). Culturing small cells from an older donor showed an increase in SSEA-4 positive cells after 5 passages in comparison to large and unsorted cells from an old donor. Further, culturing in ECM showed an increase in stem cells in comparison to culturing on 2D.

SSEA-4 is a marker of early-state MSCs. The number of SSEA-4 positive cells after 5 passages of BM-MSCs from young donors and small size, large size, and unsorted size BM-MSCs from old donors was determined after culturing on BM-ECM and tissue culture plastic (2D). Culturing small cells from an older donor showed an increase in SSEA-4 positive cells after 5 passages in comparison to large and unsorted cells from an old donor (FIG. 29). Further, culturing in BM-ECM showed an increase in stem cells in comparison to culturing on 2D.

Figure 26:
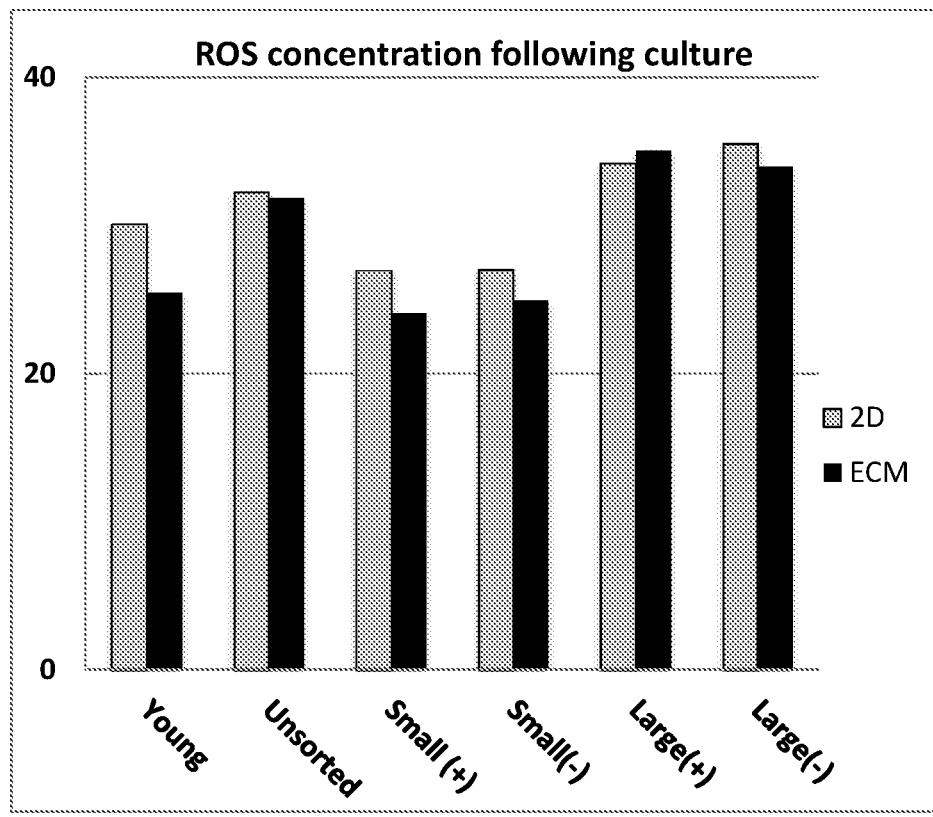
FIG. 26—ROS expression was determined following culture of young and old BM-MSCs (Young and Unsorted, respectively) and old subpopulations of BM-MSCs (Small (+), Small(−), Large(+), and Large(−)) on TCP (left column) or ECM (right column). Small(+) cells showed lower intracellular ROS than other groups, and culture on ECM further reduces mean intracellular ROS for most groups.
Figure 27:
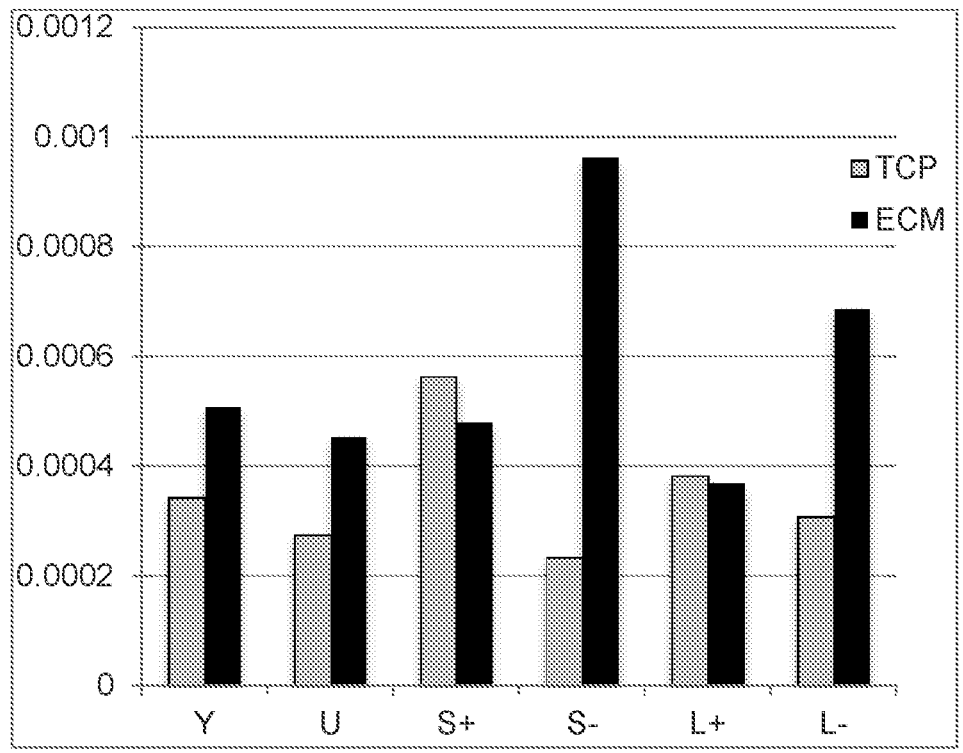
FIG. 27—ATP expression was determined following culture of young and old BM-MSCs (Y and U, respectively) and old subpopulations of BM-MSCs, Small(+), Small(−), Large(+), and Large(−) (S+, S−, L+, and L−, respectively), on TCP (left column) or ECM (right column). S+ cells cultured on tissue culture plastic (TCP) have significantly higher ATP concentration. ECM increased ATP content in most groups.
Figure 28:
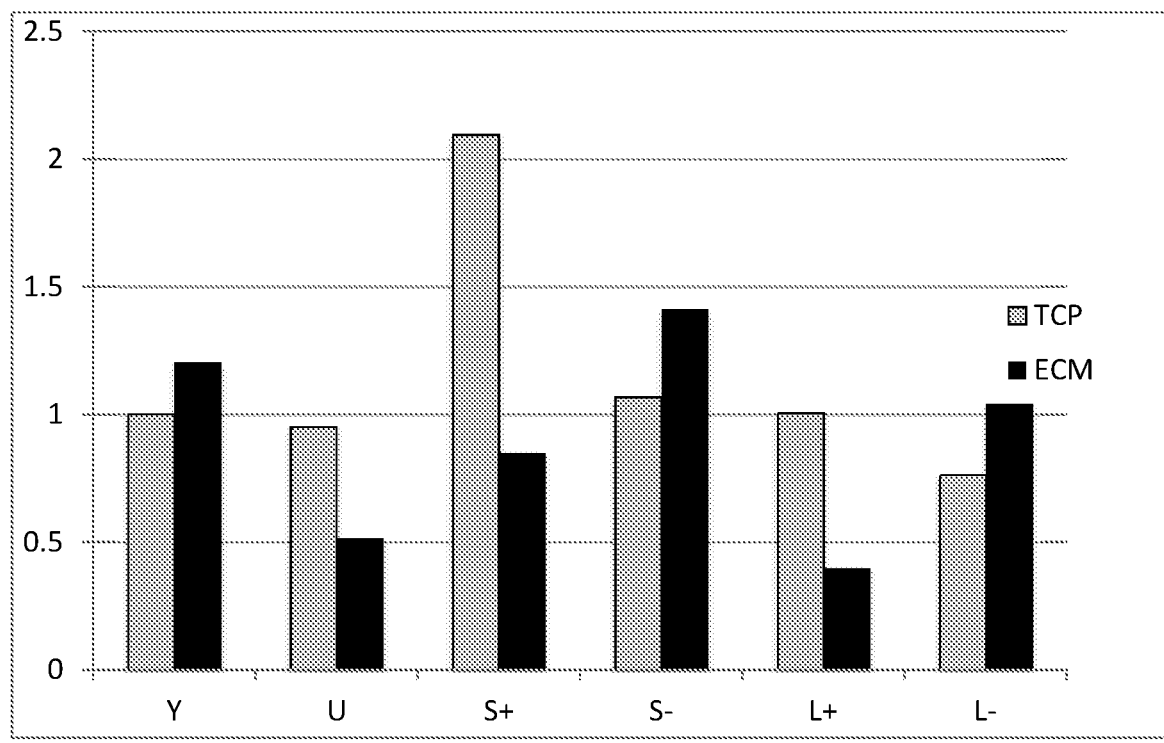
FIG. 28—Telomerase activity was determined following culture of young and old BM-MSCs (Y and U, respectively) and old subpopulations of BM-MSCs, Small(+), Small(−), Large(+), and Large(−) (S+, S−, L+, and L−, respectively), on TCP (left column) or ECM (right column). S+ cells cultured on tissue culture plastic (TCP) have significantly higher telomerase activity.
Figure 31:
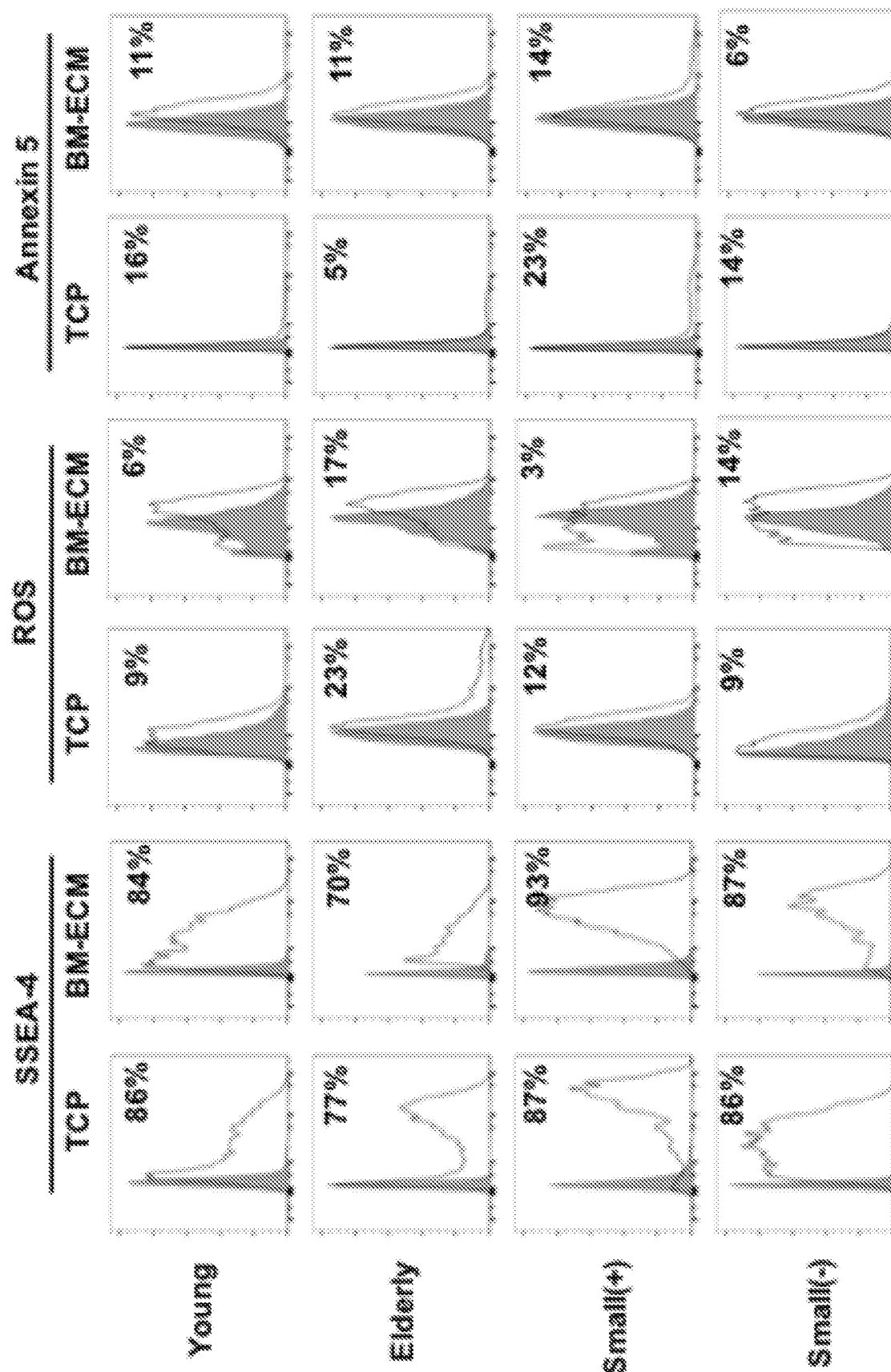
FIG. 31—Histograms of Flow Cytometry Analysis of SSEA-4, ROS, and Annexin-5 in unfractionated (Young; Elderly) and elderly fractionated BM-MSCs. Expression of SSEA-4, ROS, and annexin-5 following culture on TCP or ECM derived from BM-MSCs from young donors (young ECM). Expression was determined by flow cytometry following culture of young and elderly BM-MSCs and elderly subpopulations of BM-MSCs (Small +, Small −) on TCP or young ECM. Small + MSCs cultured on young ECM display increased SSEA-4, reduced ROS, and reduced annexin-5 expression relative to TCP. Expression was quantified by comparing fluorescent intensity of samples (black line), to negative controls (shaded region).

SSEA-4 expression, ROS concentration, ATP content per cell, and telomerase levels was also determined for the four subpopulations of BM-MSCs isolated from elderly donors (S+, S–, L+, L–) as well as unsorted BM-MSC cells from young and elderly donors cultured on TCP or ECM derived from BM-MSCs from young donors. It was found that Small(+) cells have high expression of SSEA-4, and in most groups culture on young ECM increased SSEA-4 expression. See FIGS. 25 and 31. Further, small BM-MSCs have lower intracellular ROS than other groups, and culture on young ECM further reduces mean intracellular ROS (FIGS. 26 and 31). Also, small (+) BM-MSCs cultured on TCP have significantly higher ATP concentration and culture on young ECM increases ATP concentration for most groups of cells (FIG. 27). In addition, small(+) cells have much higher telomerase activity (FIG. 28).

Small (+) and small (–) MSC populations were further compared and contrasted to unsorted young and elderly BM-MSCs when cultured on TCP or ECM derived from BM-ECM from young donors (young ECM). β-Gal expression results suggested small size sub-populations maintain low levels of senescence during culture. Specifically, small BM-MSCs isolated from elderly donors maintain low β-Gal expression during culture. Also, there was no significant difference in the β-gal levels of young vs small MSCs (FIG. 30A). This suggests this population is not transient, and can be maintained in culture. ATP levels were increased on average when BM-MSCs were culture on ECM resulted in an increase in average ATP levels relative to culture on TCP for all groups (FIG. 30B). This difference was statistically significant in 3 of the 4 groups tested. Also, small (+) BM-MSCs cultured on TCP have significantly higher ATP concentration (FIG. 30B).

Figure 30C:
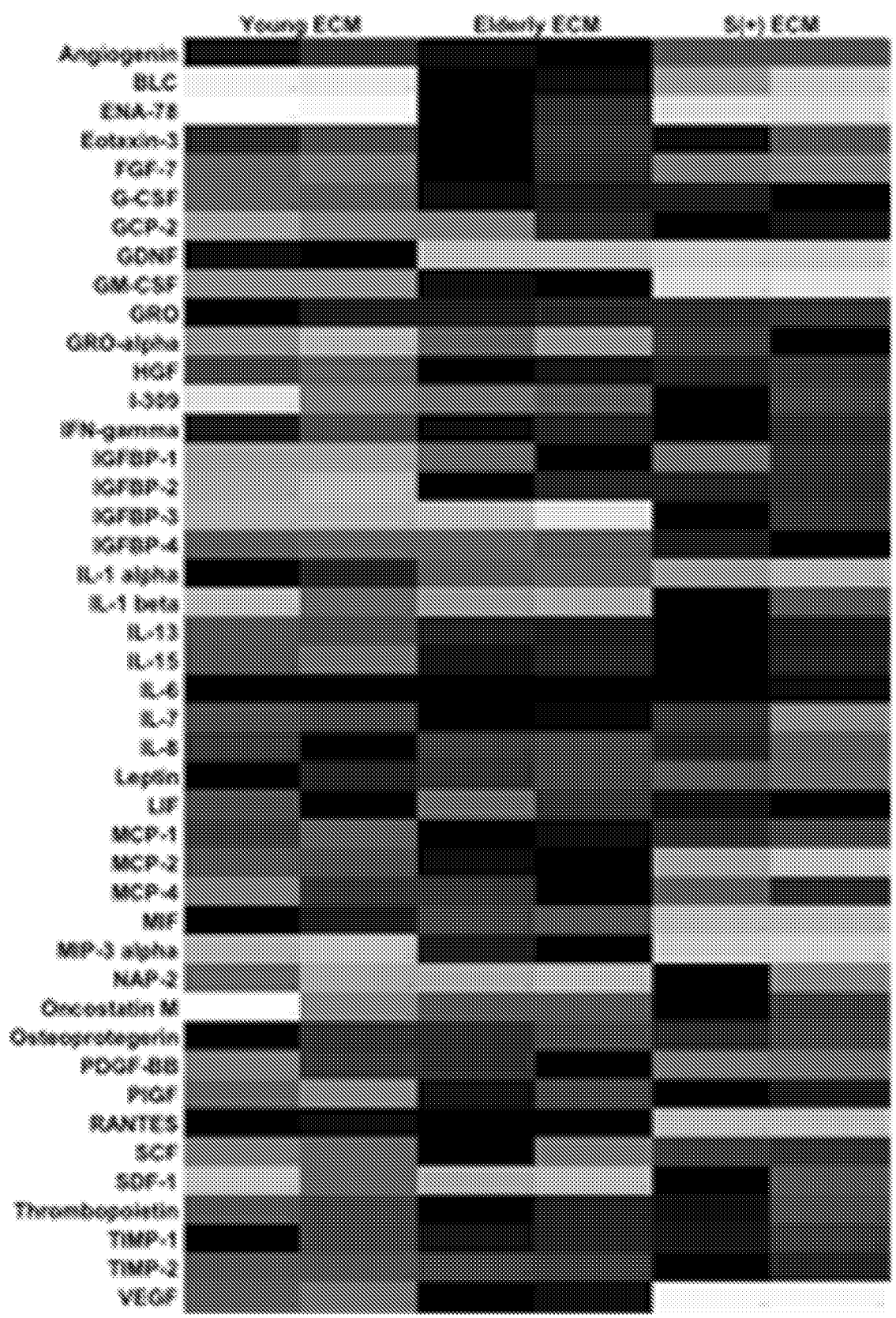

Cytokine profiles of young, elderly and small(+) BM-MSCs were compared (FIG. 30C). A similar trend emerged, with elderly BM-MSCs expressing much higher levels of SASP cytokines than young or small(+) BM-MSCs (p=0.0001 and 0.011, respectively), while the SASP profile of young and small(+) BM-MSCs were not significantly different (p=0.2756).

To determine if BM-ECM permits the expansion of large numbers of high quality MSCs, small BM-MSCs were immunophenotyped following expansion on TCP and ECM and compared to young and elderly MSCs (TABLE 2 and FIG. 31). Small(+) BM-MSCs cultured on ECM surpassed all other groups in SSEA-4 expression, while having minimal levels of intracellular reactive oxygen species (ROS). While all groups cultured on ECM had similar expression of Annexin-5, it is of note, that small(+) BM-MSCs expressed significantly lower levels on ECM relative to TCP. Together, flow cytometry shows a substantial reversal in age-related phenotypic changes in the small(+) BM-MSC group. Small (+) BM-MSCs cultured on ECM have higher SSEA-4 expression and lower ROS and annexin-5 relative to TCP culture. This demonstrates that small size BM-MSCs have a phenotype more similar to young cells, such as higher SSEA-4, lower annexin-5, and lower intracellular reactive oxygen species (ROS). These data also shows that a "youthful" sub-population of MSCs may be expanded on while maintaining a "youthful" phenotype.

TABLE 2

|  | SSEA-4 | | ROS | | Annexin 5 | |
| --- | --- | --- | --- | --- | --- | --- |
|  | TCP | BM-ECM | TCP | BM-ECM | TCP | BM-ECM |
| Young | 86% | 84% | 9% | 6% | 16% | 11% |
| Elderly | 77% | 70% | 23% | 17% | 5% | 11% |

TABLE 2-continued

|  | SSEA-4 | | ROS | | Annexin 5 | |
| --- | --- | --- | --- | --- | --- | --- |
|  | TCP | BM-ECM | TCP | BM-ECM | TCP | BM-ECM |
| Small (+) | 87% | 93% | 12% | 3% | 23% | 14% |
| Small (−) | 86% | 87% | 9% | 14% | 14% | 6% |

Example 8

Differentiation Capacity and Efficacy for Tissue Repair and Regeneration

Based on the data presented above, the inventors predict that the differentiation capacity and efficacy for tissue repair and regeneration will be increased in Small+ cells in comparison to other subpopulations of MSCs and in comparison to unsorted MSCs. It is further predicted that cells, and especially Small+ cells cultured on ECM will have a greater differentiation capacity and efficacy for tissue repair and regeneration than cells cultured on TCP.

Cell differentiation capacity of isolated MSCs can be determined by methods well known by one of skill in the art. It is expected that Small+ cells will show an increased cell differentiation capacity over other subpopulations of MSCs and in comparison to unsorted MSCs. Further it is expected that cells and especially Small+ cells cultured on young ECM will have a greater increase in cell differentiation capacity than Small+ cells cultured on TCP.

Tissue repair and regeneration of isolated-MSCs can be determined by methods well known by one of skill in the art. It is expected that Small+ cells will show an increased efficacy for tissue repair and regeneration over other subpopulations of MSCs and in comparison to unsorted MSCs. Further it is expected that cells and especially Small+ cells cultured on young ECM will have a greater increase in efficacy for tissue repair and regeneration than Small+ cells cultured on TCP.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Athanasiou, et al., *Biomaterials.* 17(2):93-102, 1996.
Bonab, et al., *BMC Cell Biol.* 7:14, 2006.
Campisi, et al., *Semin Cancer Biol.* 21(6):354-59, 2011.
Cancedda, et al., *Matrix Biol.* 22(1):81-91, 2003.
Chan, et al., *Biomaterials.* 33(2):464-72, 2012.
Chen, et al., *Tissue Eng.* 11(3-4):526-34, 2005.
Chen, et al., *J. Bone Miner. Res.* 22:1943-1956, 2007.
Chen, *Birth Defects Res C Embryo Today.* 90(1):45-54, 2010.
Cho, et al., *Blood.* 111(12):5553-61, 2008.
Coppé, et al., *PLoS Biol.* 6(12):2853-68, 2008.
Costa, et al., *Int J Biochem Cell Biol.* 44(12):2233-7, 2012.
Freund, et al., *Trends Mot Med.* 16(5):238-46, 2010.
Gang, et al., *Blood.* 109(4):1743-51, 2007.
Kagami, et al., *Oral Dis.* 14(1):15-24, 2008.
Kawanabe, et al., *Clin. Oral Investig.,* 19(2):363-71, 2015.
Lai, et al., *Stem Cells Dev.* 19:1095-1107, 2010.
Leal-Egana & Scheibel, *Biotechnol Appl Biochem.* 55(3):155-67, 2010.
Maria, et al., *Tissue Eng Part A.* 17(9-10):1229-38, 2011.
Nagaoka, et al., *Ann Biomed Eng.* 38(3):683-93, 2010.
Pipino, et al., *Stem Cells Dev.* 24(12):1415-28, 2015.
Sun, et al., *FASEB J.* 25(5):1474-85, 2011.
Wagner, et al., *PLoS ONE.* 3(5):e2213.
Zhou, et al., *Aging Cell.* 7(3):335-43, 2008.
U.S. Pat. No. 8,084,023, Chen et. al.
U.S. Pat. No. 8,388,947, Chen et. al.
U.S. Pat. No. 8,961,955, Chen et. al.
PCT Publication WO 2016/070057, Zamilpa et al.

What is claimed is:

1. A method of administering small size bone marrow-derived mesenchymal stem cells (BM-MSCs) to a subject, the method comprising:
    (a) sorting BM-MSCs harvested from a first donor by size and optionally SSEA-4 expression, wherein the small size BM-MSCs have a median diameter of less than 30 microns when measured in suspension,
    (b) isolating the small size BM-MSCs,
    (c) plating the small size BM-MSCs for culturing,
    (d) expanding the small size BM-MSCs in culture,
    (e) optionally storing the small size BM-MSCs from step (d),
    (f) administering the small size BM-MSCs from step (d) and/or (e) to the subject, wherein the subject is the same as the first donor, and wherein the subject has decreased quantity and/or quality of BM-MSCs, and/or is in need of stem cell therapy.

2. The method of claim 1, further comprising, prior to step (a), harvesting the BM-MSCs from the first donor.

3. The method of claim 1, wherein the small size BM-MSCs expressed SSEA-4 (SSEA-4 +) at the time of isolation.

4. The method of claim 1, wherein the subject is 50 years of age or older.

5. The method of claim 1, wherein the small BM-MSCs are cultured on TCP or on extracellular matrix (ECM) derived from a second set of BM-MSCs obtained from a second donor.

6. The method of claim 5, wherein the second donor is 25 years of age or younger.

7. The method of claim 1, wherein the subject has an age-related degenerative disease, and/or has a disease or condition that compromises the quantity and/or quality of BM-MSCs, and/or has or will receive treatments that compromise the quantity and/or quality of BM-MSCs.

8. A method of obtaining small size BM-MSCs suitable for administration to a subject, the method comprising:
    (a) sorting BM-MSCs harvested from a first donor by size and optionally SSEA-4 expression, wherein the BM-MSCs have a median diameter of less than 30 microns when measured in suspension,
    (b) isolating the small size BM-MSCs, (c) plating the small size BM-MSCs for culturing,
(d) expanding the small size BM-MSCs in culture, and
(e) optionally storing the small size BM-MSCs from step (d), wherein the subject has decreased quantity and/or quality of BM-MSCs, and/or is in need of stem cell therapy.

9. The method of claim 8, wherein the small size BM-MSCs expressed SSEA-4 (SSEA-4 +) at the time of isolation.

10. The method of claim 8, wherein the first donor is 50 years of age or older.

11. The method of claim 8, wherein the small BM-MSCs are cultured on TCP or on extracellular matrix (ECM) derived from a second set of BM-MSCs obtained from a second donor.

12. The method of claim 11, wherein the second donor is 25 years of age or younger.

13. The method of claim 8, wherein the first donor has an age-related degenerative disease, and/or has a disease or condition that compromises the quantity and/or quality of BM-MSCs, and/or has or will receive treatments that compromise the quantity and/or quality of BM-MSCs.

14. The method of claim 8, further comprising, prior to step (a), harvesting the BM-MSCs from the first donor.

* * * * *